United States Patent
Hoveyda et al.

(10) Patent No.: US 9,949,949 B2
(45) Date of Patent: *Apr. 24, 2018

(54) MACROCYCLIC GHRELIN RECEPTOR MODULATORS AND METHODS OF USING THE SAME

(71) Applicant: OCERA THERAPEUTICS, INC., Palo Alto, CA (US)

(72) Inventors: Hamid Hoveyda, Brussels (BE); Graeme Fraser, Bousval (BE); Kamel Benakli, Blue Bell, PA (US); Eric Marsault, Sherbrooke (CA); Mark L. Peterson, Sherbrooke (CA)

(73) Assignee: Ocera Therapeutics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/178,303

(22) Filed: Jun. 9, 2016

(65) Prior Publication Data

US 2017/0042858 A1 Feb. 16, 2017

Related U.S. Application Data

(62) Division of application No. 12/028,611, filed on Feb. 8, 2008, now Pat. No. 9,371,297.

(60) Provisional application No. 60/889,163, filed on Feb. 9, 2007.

(51) Int. Cl.
| | |
|---|---|
| C07K 5/12 | (2006.01) |
| A61K 31/395 | (2006.01) |
| C07D 273/00 | (2006.01) |
| C07C 271/16 | (2006.01) |
| C07C 215/42 | (2006.01) |
| C07C 215/54 | (2006.01) |
| C07D 413/06 | (2006.01) |
| C07D 498/04 | (2006.01) |
| C07D 498/16 | (2006.01) |

(52) U.S. Cl.
CPC .......... *A61K 31/395* (2013.01); *C07C 215/42* (2013.01); *C07C 215/54* (2013.01); *C07C 271/16* (2013.01); *C07D 273/00* (2013.01); *C07D 413/06* (2013.01); *C07D 498/04* (2013.01); *C07D 498/16* (2013.01); *C07C 2601/14* (2017.05)

(58) Field of Classification Search
None
See application file for complete search history.

(56) References Cited

U.S. PATENT DOCUMENTS

| | | | |
|---|---|---|---|
| 5,158,978 A | 10/1992 | Rubin | |
| 5,407,688 A | 4/1995 | Place | |
| 6,194,382 B1 | 2/2001 | Crain et al. | |
| 6,294,346 B1 | 9/2001 | Weiss et al. | |
| 6,638,540 B2 | 10/2003 | Mühlbauer | |
| 7,041,786 B2* | 5/2006 | Shailubhai | A61K 45/06 530/300 |
| 7,446,089 B2 | 11/2008 | Singh et al. | |
| 7,452,862 B2 | 11/2008 | Deslongchamps et al. | |
| 7,476,653 B2 | 1/2009 | Hoveyda et al. | |
| 7,491,695 B2 | 2/2009 | Fraser et al. | |
| 7,521,420 B2 | 4/2009 | Fraser et al. | |
| 7,550,431 B2 | 6/2009 | Deslongchamps et al. | |
| 8,088,733 B2 | 1/2012 | Fraser et al. | |
| 2002/0018767 A1 | 2/2002 | Lee et al. | |
| 2005/0054562 A1 | 3/2005 | Fraser et al. | |
| 2005/0137127 A1 | 6/2005 | Deslongchamps et al. | |
| 2006/0025566 A1 | 2/2006 | Hoveyda et al. | |
| 2007/0021331 A1 | 1/2007 | Fraser et al. | |
| 2009/0240027 A1 | 9/2009 | Marsault et al. | |

FOREIGN PATENT DOCUMENTS

| | | |
|---|---|---|
| FR | 2284321 | 4/1976 |
| JP | 56142272 A | 11/1981 |
| WO | WO 2004/111077 A1 | 12/2004 |
| WO | WO 2005/012331 A1 | 2/2005 |
| WO | WO 2006/009645 A1 | 1/2006 |
| WO | WO 2006/09674 A1 | 1/2006 |
| WO | WO 2006/046977 A1 | 5/2006 |

(Continued)

OTHER PUBLICATIONS

Riddle et al. "Emerging Therapies Mimicking the Effects of Amylin and Glucagon-Like Peptide 1", *Diabetes Care* 29(2):435-449 (2006).

Marsault et al. "Discovery of a New Class of Macrocyclic Antagonists to the Human Motilin Receptor", *J. Med. Chem*, 49:7190-7197 (2006).

Invitation to Pay Additional Fees and, Where Applicable, Protest Fee corresponding to International Application No. PCT/US2008/001754 dated Jul. 8, 2008.

Notification of Transmittal of the International Search Report and the Written Opinion of the International Searching Authority, or the Declaration corresponding to International Application No. PCT/US2008/001754 dated Sep. 19, 2008.

(Continued)

*Primary Examiner* — Jeanette Lieb
(74) *Attorney, Agent, or Firm* — Ward & Smith, P.A.

(57) ABSTRACT

The present invention provides novel conformationally-defined macrocyclic compounds that can function as selective modulators of the ghrelin receptor (growth hormone sceretagogue receptor, GHS-R1a and subtypes, isoforms and variants thereof). Methods of synthesizing the novel compounds are also described herein. These compounds are useful as agonists of the ghrelin receptor and as medicaments for treatment and prevention of a range of medical conditions including, but not limited to, metabolic and/or endocrine disorders, gastrointestinal disorders, cardiovascular disorders, obesity and obesity-associated disorders, central nervous system disorders, bone disorders, genetic disorders, hyperproliferative disorders and inflammatory disorders.

11 Claims, 8 Drawing Sheets

(56) References Cited

FOREIGN PATENT DOCUMENTS

WO    WO 2006/052608 A2    5/2006
WO    WO 2006/137974 A2    12/2006

OTHER PUBLICATIONS

First Examination Report corresponding to Eurasian Patent Application No. 200901077/28 dated Nov. 12, 2011.
Extended European Search Report corresponding to European Patent Application No. 12195556.1 dated Sep. 3, 2013.

* cited by examiner

A)

B)

A)

B)

A)

B)

A)

B)

A)

B)

A)

B)

MACROCYCLIC GHRELIN RECEPTOR MODULATORS AND METHODS OF USING THE SAME

RELATED APPLICATION INFORMATION

This application is a divisional of and claims priority to U.S. patent application Ser. No. 12/028,611, filed Feb. 8, 2008, which claims the benefit of U.S. Provisional Application Ser. No. 60/889,163, filed Feb. 9, 2007, the disclosures of each of which is incorporated herein by reference in its entirety.

FIELD OF THE INVENTION

The present invention relates to novel conformationally-defined macrocyclic compounds that bind to and/or are functional modulators of the ghrelin (growth hormone secretagogue) receptor including GHS-R1a and subtypes, isoforms and/or variants thereof. The present invention also relates to intermediates of these compounds, pharmaceutical compositions containing these compounds and methods of using the compounds. These novel macrocyclic compounds are useful as therapeutics for a range of disease indications. In particular, these compounds are useful for treatment and prevention of gastrointestinal disorders including, but not limited to, post-operative ileus, gastroparesis, including diabetic gastroparesis, opioid bowel dysfunction, chronic intestinal pseudo-obstruction, short bowel syndrome and functional gastrointestinal disorders. Additionally, the compounds have application, for the treatment and prevention of metabolic and/or endocrine disorders, cardiovascular disorders, obesity and obesity-associated disorders, central nervous system disorders, bone disorders, genetic disorders, hyperproliferative disorders and inflammatory disorders.

BACKGROUND OF THE INVENTION

The improved understanding of various physiological regulatory pathways facilitated through the research efforts in genomics and proteomics has begun to impact the discovery of novel pharmaceutical agents. In particular, the identification of key receptors and their endogenous ligands has created new opportunities for exploitation of these receptor/ligand pairs as therapeutic targets. For example, ghrelin is a recently characterized 28-amino acid peptide hormone isolated originally from the stomach of rats with the orthologue subsequently identified in humans. (Kojima, M.; Hosoda, H. et al. *Nature* 1999, 402, 656-660.) The existence of this peptide in a range of other species suggests a conserved and important role in normal body function. This peptide has been demonstrated to be the endogenous ligand for a previously orphan G protein-coupled receptor (GPCR), type 1 growth hormone secretatogue receptor (hGHS-R1a) (Howard, A. D.; Feighner, S. D.; et al. *Science* 1996, 273, 974-977) found predominantly in the brain (arcuate nucleus and ventromedial nucleus in the hypothalamus, hippocampus and substantia nigra) and pituitary. (U.S. Pat. No. 6,242,199; Intl. Pat. Appl. Nos. WO 97/21730 and WO 97/22004) hGHS-R1a has recently been reclassified as the ghrelin receptor (GHRN) in recognition of its endogenous ligand (Davenport, A. P.; et al. *Pharmacol. Rev,* 2005, 57, 541-546). The receptor has also been detected in other areas of the central nervous system (CNS) and in peripheral tissues, for instance adrenal and thyroid glands, heart, lung, kidney, and skeletal muscle. This receptor was identified and cloned prior to the isolation and characterization of the endogenous peptide ligand and is distinct from other receptors involved in the regulation of growth hormone (GH) secretion, in particular, the growth hormone-releasing hormone (GHRH) receptor.

A unique characteristic of both the rat and human peptides is the presence of the n-octanoyl (Oct) moiety on Ser$^3$. However, the des-acyl form predominates in circulation, with approximately 90% of the hormone in this form. This group is derived from a post-translational modification and appears relevant for bioactivity and possibly also for transport into the CNS. (Banks, W. A.; Tschöp, M.; Robinson, S. M.; Heiman, M. L. *J. Pharmacol. Exp. Ther.* 2002, 302, 822-827.) In a GH-releasing assay, the des-octanoyl form of the hormone was at least 100-fold less potent than the parent peptide, although it has been suggested that the des-acyl species may be responsible for some of the other biological effects associated with ghrelin. This des-acyl form has also been postulated to be primarily responsible for the cardiovascular and cell proliferation effects attributed to ghrelin, while the acylated form participates in maintenance of energy balance and growth hormone release, (Baldanzi, G.; Filighenddu, N.; Cutrupi, S.; et al. *J. Cell Biol.* 2002, 159, 1029-1037.) Similarly; des-Gln$^{14}$-ghrelin and its octanoylated derivative have been isolated as endogenous forms of the hormone arising from alternative splicing of the ghrelin gene, but both are found to be inactive in stimulating GH release in vivo. (Hosoda, H.; Kojima, M.; Matsuo, H.; Kangawa, K., *J. Biol. Chem.* 2000, 275, 21995-2120.) Other minor forms of ghrelin produced by post-translational processing have been observed in plasma, although no specific activity has been attributed to them. (Hosoda, H.; Kojima, M.; et al. *J. Biol. Chem.* 2003, 278, 64-70.)

Even prior to the isolation of this receptor and its endogenous peptide ligand, a significant amount of research was devoted to finding agents that can stimulate GH secretion. The proper regulation of human GH has significance not only for proper body growth, but also a range of other critical physiological effects. Since GH and other GH-stimulating peptides, such as GHRH and growth hormone releasing factor (GRF), as well as their derivatives and analogues, are administered via injection, to better take advantage of these positive effects, attention was focused on the development of orally active therapeutic agents that would increase GH secretion, termed GH secretagogues (GHS). Additionally, use of these oral agents was expected to more closely mimic the pulsatile physiological release of GH.

Beginning with the identification of the growth hormone-releasing peptides (GHRP) in the late 1970's (Bowers, C. Y. *Curr. Opin. Endocrinol. Diabetes* 2000, 7, 168-174; Camanni, F.; Ghigo, E.; Arvat, E. *Front. Neuroscl.* 1998, 19, 47-72; Locatelli, V.; Torsello, A., *Pharmacol. Res.* 1997, 36, 415-423), a host of agents have been studied for their potential to act as GHS. In addition to their stimulation of OH release and concomitant positive effects in that regard, GHS were projected to have utility in the treatment of a variety of other disorders, including wasting conditions (cachexia) as seen in HIV/AIDS patients and cancer-induced anorexia, musculoskeletal frailty in the elderly, and growth hormone deficient diseases. Many efforts over the past 25 years have yielded a number of potent, orally available GHS. (Rocha-Sousa, A.; Henriques-Coelho, T.; Leite_Moreira, A. F. *Exp. Opin. Ther. Patents* 2007, 17, 909-926; Isidro, M. L.; Cordido, F. *Comb. Chem. High Throughput Screen.* 2006, 9, 178-180; Smith, R. G.; Sun, Y. X.; Beatancourt, L.; Asnicar, M. *Best Pract. Res. Clin. Endocrinol. Metab.* 2004, 18, 333-347; Fehrentz, J.-A.; Martinez, J.;

Boeglin, D.; Guerlavais, V.; Deghenghi, R. *IDrugs* 2002, 5, 804-814; Svensson, *J. Exp. Opin. Ther. Patents* 2000, 10, 1071-1080; Nargund, R. P.; Patchett, A. A.; et al., *J. Med. Chem.* 1998, 41, 3103-3127; Ghigo, E; Arvat, E.; Camanni, F. *Ann. Med* 1998, 30, 159-168; Smith, R. O.; Van der Ploeg, L.H. T.; Howard, A. D.; Feighner, S. D.; et al. *Endocr. Rev.* 1997, 18, 621-645.) These include small peptides, such as hexarelin (Zentaris) and ipamorelin (Novo Nordisk), and adenosine analogues, as well as small molecules such as capromorelin (Pfizer), L-252,564 (Merck), MK-0677 (Merck), NN703 (tabimorelin, Novo Nordisk), G-7203 (Genentech), S-37435 (Kaken) and SM-130868 (Sumitomo), BMS-604992 (Bristol-Myers Squibb) and RC-1291 (anamorelin, Sapphire) designed to be orally active for the stimulation of growth hormone. However, clinical testing with such agents have rendered disappointing results due to, among other things, lack of efficacy over prolonged treatment or undesired side effects, including irreversible inhibition of cytochrome P450 enzymes (Zdravkovic M.; Olse, A. K.; Christiansen, T.; et al. *Eur. J. Clin. Pharmacol,* 2003, 58, 683-688.) Therefore, there remains a need for pharmacological agents that could effectively target the ghrelin receptor for therapeutic action.

Despite its involvement in GH modulation, ghrelin is primarily synthesized in the oxyntic gland of the stomach, although it is also produced in lesser amounts in other organs, including the kidney, pancreas and hypothalamus. (Kojima, M.; Hsoda, H.; Kangawa, K. *Horm. Res.* 2001, 56 (Suppl. 1), 93-97; Ariyasu, H.; Takaya, K.; Tagami, T.; et al. Stomach is a major source of circulating ghrelin, and feeding state determines plasma ghrelin-like immunorcactivity levels in humans. *J. Clin. Endocrinol. Metab.* 2001, 86, 4753-4758.) in addition to its role in stimulating GH release, the hormone has a variety of other endocrine and non-endocrine functions (Broglio, F.; Gottero, C.; Arvat, E.; Ghigo, E. *Horm. Res.* 2003, 59, 109-117) and has been shown to interact with a number of other physiological systems in maintaining proper energy balance, (Horvath, T. L.; Diano, S.; Sotonyi, P.; Heiman, M.; Tschöp, M. *Endocrinology* 2001, 142, 4163-4169; Casanueva, F. F.; Dieguez, C. *Rev. Endocrinol. Metab. Disord* 2002, 3, 325-338). In particular, ghrelin plays a role as an orexigenic signal in the control of feeding, in which it acts to counteract the effects of leptin. Indeed, it was the first gut peptide proven to have such orexigenic properties. (Kojima, M.; Kangawa, K. *Curr Opin. Pharmacology* 2002, 2, 665-668.) The hormone also is implicated in the hypothalamic regulation of the synthesis and secretion of a number of other neuropeptides involved in appetite and feeding behavior. Levels of ghrelin are elevated in response to fasting or extended food restriction. (Nakazato, M.; Murakami, N.; Date, Y.; Kojima, M.; et al. *Nature* 2001, 409, 194-198.) For example, subjects suffering with anorexia or bulimia exhibit elevated ghrelin levels. Circulating levels of the hormone have been found to rise before meals and fall after meals. In addition, diet-induced weight loss leads to increased ghrelin levels, although obese subjects who have gastric bypass surgery do not likewise experience such an increase. (Cummings, D. E.; Weigle, D. S.; Frayo, R. S.; et al. *N. Engl. J. Med.* 2002, 346, 1623-1630)

This intimate involvement of ghrelin in control of food intake and appetite has made it an attractive target for obesity research. (Spanswick, D.; Lee, K. *Exp. Opin. Emerging Drugs* 2003, 8, 217-237; Horvath, T. L.; Castañeda, T.; Tang-Christensen, M.; Pagotto, U.; Tschöp, M. H. *Cur. Pharm. Design* 2003, 9, 1383-1395; Crowley, V. E. F.; Yeo, G. S. H.; O-Rahilly, S. *Nat. Rev. Drug Disc.* 2002, 1, 276-286.) Indeed, few other natural substances have been demonstrated to be involved in the modulation of both GH secretion and food intake.

Similarly, ghrelin plays a role in the regulation of insulin release and glycemia and hence modulators of the ghrelin receptor have application to the treatment of diabetes and metabolic syndrome. (Yada, T.; Dezaki, K. Sone, H.; et al. *Curr. Diab. Rev.* 2008, 4, 18-23).

Also, as previously mentioned with respect to the GHS, ghrelin and ghrelin agonists have been demonstrated to have positive effects in wasting syndromes and cachexia. Clinical trials have been initiated to take advantage of these effects. (Strasser, F.; Lutz, T. A.; Maeder, M. T. *Br. J. Cancer* 2008, 98, 300-308. Garcia, J. M.; Polvino, W. J. *The Oncologist* 2007, 12, 594-600.)

An additional effect of ghrelin that has not been exploited to date for therapeutic purposes is in modulating gastric motility and gastric acid secretion. The pro-kinetic activity appears to be independent of the GH-secretory action and is likely mediated by the vagal-cholinergic muscarinic pathway. The dose levels required are equivalent to those necessary for the hormone's GH and appetite stimulation actions. It is noteworthy that, in contrast to its inactivity for ghrelin's other actions, the des-Gln$^{14}$ peptide demonstrated promotion of motility as well. (Chen, C.-Y.; Inui, A.; Asakawa, A.; Fujino, K.; Kato, I.; Chen, C.-C.; Ueno, N.; Fujimiya, M. *Gastroenterology* 2005, 129, 8-25; Chen, C.-Y.; Chao, Y.; Chang, F.-Y.; Chien, E. J.; Lee, S.-D.; Doong, M.-L. *Int. J. Mol. Med.* 2005, 16, 695-699; Trudel, L.; Bouin, M.; Tomasetto, C.; Eberling, P.; St-Pierre, S.; Bannon, P.; L'Heureux, M. C.; Poitras, P. *Peptides* 2003, 24, 531-534; Trudel, L.; Tomasetto, C.; Rio, M. C.; Bouin, M.; Plourde, V.; Eberling, P.; Poitras, P. *Am. J. Physiol.* 2002, 282, G948-G952; Peeters, T. L. *J. Physiol. Pharmacol,* 2003, 54(Supp. 4), 95-103.)

A growing amount of evidence has demonstrated ghrelin to be a regulator of inflammation and immune function. (Taub, D. D. Vitamins and Hormones 2007, 77, 325-346; Vixit, V. D.; Taub, D. D. *Exp. Gerontol.* 2005, 40, 900-910.) Ghrelin specifically inhibits the expression of pro-inflammatory cytokines such as IL-1β, IL-6 and TNF-α in human monocytes and T cells (Dixit, V. D.; Schaffer, E. M.; et al. *J. Clin. Invest,* 2004, 114, 57-66). Ghrelin exhibits novel anti-inflammatory actions in human endothelial cells through deactivation of the NF-κB pathway, (Li, W. G.; Gavrila, D.; Liu, X.; et al. *Circulation* 2004, 109, 2221-2226; Zhao, D.; Zhan, Y.; Zeng, H.; et al. *J. Cell. Biochem.* 2006, 97, 1317-1327.) Ghrelin exerts a protective effect on the gastric mucosa mediated in part through prostaglandins. (Konturek, P. C.; Brzozowski, T.; Pajdo, R.; et al. *J. Physiol. Pharmacol.* 2004, 55, 325-336.) Ghrelin levels are elevated in patients with IBD (Peracchi, M.; Bardella, M. T.; et al. *Gut* 2006, 55, 432-433; Karmiris, K.; Koutroubakis, I. E.; et al. *Inflamm. Bowel Dis.* 2006, 12, 100-105), colitis (Gonzalez-Rey, E.; Chorny, A.; Delgado, M. *Gastroenerology* 2006, 130, 1707-1720), peptic ulcer disease (Suzuki, H.; Masaoka, T.; Nomoto, Y.; et al. *Aliment. Pharmacol. Ther. Symp. Ser* 2006, 2, 120-126), duodenal ulcers (Fukuhara, S.; Suzuki, H.; Masaoka, T.; et al. *Am. J. Physiol.* 2004, 289, G138-G145) and postoperative intra-abdominal sepsis (Maruna, P.; Gürlich, R.; Frasko, R.; Rosicka, M. *Eur. Surg. Res.* 2005, 37, 354-359), but decreased in rheumatoid arthritis (Otero, M.; Nogueiras, R.; et al. *Rheumatol.* 2004, 43, 306-310). In rat models, ghrelin peptide protects against or improves ischemia-reperfusion injury (Konturek, P. C.; Brzozowski, T.; et al. *Eur. J. Pharmacol.* 2006, 536, 171-181), pancreatic and liver damage (Kasimay, O.; Iseri, S. O.; Barlas, A.; et al.

Hepatol. Res. 2006, 36, 11-19), acute pancreatitis (Dembinski, A.; Warzecha, Z.; et al. *J. Physiol. Pharmacol.* 2003, 54, 561-573), sepsis and septic shock (Wu, R.; Dong, W.; Cui, X.; et al. *Ann. Srg.* 2007, 245, 480-486; Chang, L.; Lu, J.-B.; et al. *Acta Pharmacol. Sin.* 2003, 24, 45-49), gastric damage caused by certain drugs (Iseri, S.; Sener, G.; et al. *J. Endocrinol.* 2005, 187, 399-406), stress-induced gastric damage (Brzozowski, T.; Konturek, P. C.; Kontutek, S. J.; et al. *Regul. Pept.* 2004, 120, 39-51), gastric damage caused by *H. pylori* (Isomoto, H.; Ueno, H.; et al. *Dig. Dis. Sci.* 2005, 50, 833-838) and inflammatory pain (Sibilia, V.; Lattuada, N.; et al. *Neuropharmacology* 2006, 51, 497-505). Ghrelin is, as well, associated with chronic kidney disease (Stenvinkel, P.; Pecoits-Filho, R.; Lindholm, B. *Adv. Renal Replacement Ther.* 2003, 10, 332-3450). Further, peptide agonists have proven efficacious in animal models, including GHRP-2 for arthritis in the rat (Granado, M.; Priego, T.; et al. *Am. J. Physiol.* 2005, 288, E486-E492; *Am. J. Physiol.* 2005, 289, E1007) and GHRP-6 for acute ischemia in dogs (Shen, Y.-T.; Lynch, J. J.; Hargreaves, R. J.; Gould, R. J. *J. Pharmacol. Exp. Ther.* 2003, 306, 815-820.) Ghrelin and ghrelin agonists hence can be applied to the treatment and prevention of inflammatory disorders. Interestingly, ghrelin antagonists have been described to be useful for the treatment of intestinal inflammation (U.S. Pat. Appl. Publ. 2007/0025991).

Ghrelin also has been implicated in various aspects of reproduction and neonatal development. (Arvat, E.; Gianotti, L.; Giordano, R.; et al. *Endocrine* 2001, 14, 35-43.) Also of significance are the cardiovascular effects of ghrelin, since the peptide is a powerful vasodilator. As such, ghrelin agonists have potential for the treatment of chronic heart failure. (Nagaya, N.; Kangawa, K. *Regul. Pept.* 2003, 114, 71-77; Nagaya, N.; Kangawa, K. *Curr. Opin. Pharmacol.* 2003, 3, 146-151; Bedendi, I.; Alloatti, G.; Marcantoni, A.; Malan, D.; Catapano, F.; Ghé, C.; et al. *Eur. J. Pharmacol* 2003, 476, 87-95; Isgaard, J.; Johansson, I. *J. Endocrinol. Invest.* 2005, 28, 838-842.) Intl. Pat. Appl. Publ. WO 2004/014412 describes the use of ghrelin agonists for the protection of cell death in myocardial cells and as a cardioprotectant treatment for conditions leading to heart failure.

Ghrelin has also been implicated in the regulation of bone metabolism. (van der Velde, M.; Delhanty, P.; et al. *Vitamins and Hormones* 2008, 77, 239-258). Ghrelin and its receptor, GHS-R1a, were identified in osteoblasts, and ghrelin promoted both proliferation and differentiation. Furthermore, ghrelin increased bone mineral density and directly affects bone formation in rats. (Fukushima, N.; Hanada, R.; Teranishi, H.; et al. *J. Bone Mineral Res.* 2005, 20, 790-798).

Additionally, ghrelin peptide has been demonstrated to possess potent inhibitory effects on angiogenesis in vitro and in vivo. (Baiguera, S.; Conconi, M. T.; Guidolin, D.; et al. *Int. J. Mol. Med.* 2004, 14, 849-854; Conconi, M. T.; Nico, B.; Guidolin, D.; et al. *Peptides* 2004, 25, 2179-2185.)

Further, evidence also has been obtained that ghrelin may have implications in anxiety and other CNS disorders as well as the improvement of memory. (Carlini, V. P., Monzon, M. E., Varas, M. M., Cragnolini, A. B., Schioth, H. B., Scimonelli, T. N., de Barioglio, S. R. *Biochem. Biophys. Res. Commun.* 2002, 299, 739-743; Diano, S.; Farr, S. A.; Benoit, S. C.; et al. *Nature Neurosci.* 2006, 9, 381-388; McNay, E. C. *Curr. Opin. Pharmacol.* 2007, 7, 628-632.) Lastly, ghrelin has also been demonstrated to have effects on the regulation of sleep. (Szentirmai, E.; Kapás, L.; Krueger, J. M. *Am. J. Physiol. Regul. Integr. Comp. Physiol.* 2007, 292, R575-R85; Szentirmai, E.; Hajdu, L; Obal, Jr. F.; Krueger, J. M. *Brain Res.* 2006, 1088, 131-140; Yannielli, P. C.; Molyneux, P. C.; Harrington, M. E.; Golombek, D. A. *J. Neurosci.* 2007, 2890-2895; Tolle, V.; Bassant, M.-H.; Zizzari, P. *Endocrinology* 2002, 143, 1353-1361.) However, the sleep-wake cycle in ghrelin knock-out mice has been reported to be normal, indicating that the regulatory situation might be more complex. (Szentirmai, E.; Kapás, L.; et al. *Am. J. Physiol. Regul. Integr. Comp. Physiol.* 2007, 293, R510-R517.) Ghrelin agonists have utility therefore as treatments for preventing or ameliorating conditions involving the CNS, including anxiety, stress, cognitive enhancement, and sleep regulation.

WO 2005/097174 and WO 2006/045314 discuss the use of GHS, ghrelin and other peptides or combinations thereof for the treatment of cachexia and chronic obstructive pulmonary disease, respectively. WO 2005/09726 reports on GHS for treatment of diseases caused by C-reactive protein. WO 2006/045319 describes the use of GHS in the treatment of renal and/or liver failure and complications thereof. More generally, WO 2005/097173 suggests the use of GHS for the treatment of ghrelin deficiency, including a wide array of therapeutic indications.

The myriad effects of ghrelin in humans have suggested the existence of subtypes for its receptor, although none have as yet been identified. (Torsello, A.; Locatelli, Y.; Melis, M. R.; Succu, S.; Spano, M. S.; Deghenghi, R.; Muller, E. E.; Argiolas, A.; Torsello, A.; Locatelli, V.; et al. *Neuroendocrinalogy* 2000, 72, 327-332.) However, a truncated, inactive form of GHS-R1a, termed GHS-R1b, was isolated and identified at the same time as the original characterization. Evidence is mounting that additional receptor subtypes could be present in different tissues to explain the diverse effects displayed by endogenous peptides and synthetic GHS. For instance, high affinity binding sites for ghrelin and des-acyl ghrelin have also been found in breast cancer cell lines, cardiomyocytes, and guinea pig heart that are involved in mediating the antiproliferative, cardioprotective and negative cardiac inotropic effects of the peptides. Similarly, specific GHS binding sites besides GHS-R1a and GHS-R1b have been found in prostate cancer cells. Further, ghrelin and des-acyl ghrelin exert different effects on cell proliferation in prostate carcinoma cell lines. (Cassoni, P.; Ghé, C.; Marrocco, T.; et al. E *Eur. J. Endocrinol.* 2004, 150, 173-184.) These various receptor subtypes may then be implicated independently in the wide array of biological activities displayed by the endogenous peptides and synthetic GHS. Indeed, recently, the existence of receptor subtypes was offered as an explanation for the promotion of fat accumulation by ghrelin, despite its potent stimulation of the lipolytic hormone, growth hormone. (Thompson, N. M.; Gill, D. A. S.; Davies, R.; Loveridge, N.; Houston, P. A.; Robinson, I. C. A. F.; Wells, T. *Endocrinology* 2004, 145, 234-242.) Further, this work suggested that the ratio of ghrelin and des-acyl ghrelin production could help regulate the balance between adipogenesis and lipolysis in response to nutritional status.

The successful creation of peptidic ghrelin analogues that separate the GH-modulating effects of ghrelin from the effects on weight gain and appetite provides strong evidence for the existence and physiological relevance of other receptor subtypes. (Halem, H. A.; Taylor, J. E.; Dong, J. Z.; Shen, Y.; Datta, R.; Abizaid, A.; Diano, S.; Horvath, T. L.; Culler, M. D. *Neuroendocrinol.* 2005, 81, 339-349; Halem, H. A.; Taylor, J. E.; Dong, J. Z.; Shen, Y.; Datta, R.; Abizaid, A.; Diano, S.; Horvath, T.; Zizzari, P.; Bluet-Pajot, M.-T.; Epelbaum, J.; Culler, M. D. *Eur. J. Endocrinol.* 2004, 151, S71-S75.) BIM-28163 functions as an antagonist at the GHS-R1a receptor and inhibits receptor activation by native ghrelin. However, this same molecule is a full agonist with respect to stimulating weight gain and food intake. Additionally, the existence of a still uncharacterized receptor subtype has been proposed based on binding studies in various tissues that showed differences between peptidic and non-peptidic GHS. (Ong, H.; Menicoll, N.; Escher, F.; Collu, R.; Deghenghi, R.; Locatelli, V.; Ghigo, E.; Muccioli, G.; Boghen, M.; Nilsson, M. *Endocrinology* 1998, 139, 432-435.) Differences between overall GHS-R expression and that of the GHS-R1a subtype in rat testis have been reported. (Barreiro, M. L.; Suominen, J. S.; Gaytan, F.; Pinilla, L.; Chopin, L. K.; Casanueva, F. F.; Dieguez, C.; Aguilar, E.; Toppari, J.; Tena-Sempere, M. *Biol. Reproduction* 2003, 68, 1631-1640.) A GHS-R subtype on cholinergic nerves is postulated as an explanation for the differential actions of ghrelin and a peptidic GHS on neural contractile response observed during binding studies at the motilin receptor. (Depoortere, I.; Thijs, T.; Thielemans, L.; Robberecht, P.; Peeters, T. L. *J. Pharmacol. Exp. Ther.* 2003, 305, 660-667.) Finally, WO 2006/009645 and WO 2006/009674 report the separation of the GI effects from the GH-release effects in animal models using macrocyclic ghrelin agonists, also suggesting that different subtypes are involved in these physiological effects.

The variety of activities associated with the ghrelin receptor could also be due to different agonists activating different signaling pathways as has been shown for ghrelin and adenosine, both of which interact as agonists at GHS-R1a. (Carreira, M. C.; Camina, J. P.; Smith, R. G.; Casanueva, F. F. *Neuroendocrinology* 2004, 79, 13-25.)

The functional activity of a GPCR has been shown to often require the formation of dimers or other multimeric complexes with itself or other proteins. (Prinster, S. C.; Hague, C.; Hall, R. A. *Pharmacol. Rev.* 2005, 57, 289-298; Park, P. S.; Filipek, S.; Wells, J. W.; Palczewski, K. *Biochemistry* 2004, 43, 15643-15656; Rios, C. D.; Jordan, B. A.; Gomes, I.; Devi, L. A. G-protein-coupled receptor dimerization: modulation of receptor function. *Pharmacol. Ther.* 2001, 92, 71-87; Devi, L. A. *Trends Pharmacol. Sci.* 2001, 22, 532-537.) Likewise, the activity of the ghrelin receptor might also be at least partially governed by such complexes. For example, certain reports indicate that interaction of GHS-R1a with GHRH (Cunha, S. R.; Mayo, K. E. *Endocrinology* 2002, 143, 4570-4582; Malagón, M. M.; Luque, R. M.; Ruiz-Guerrero, E.; Rodríguez-Pacheco, F.; García-Navarro, S.; Casanueva, F. F.; Gracia-Navarro, F.; Castaño, J. P. *Endocrinology* 2003, 144, 5372-5380) or between receptor subtypes (Chan, C. B.; Cheng, C. H. K. *Mol. Cell. Endocrinol.* 2004, 214, 81-95) may be involved in modulating the function of the receptor.

Further, the appetite regulating effects of ghrelin have been attributed to the constitutive activity of the receptor. (Holst, B. Schwartz, T. *J. Clin. Invest.* 2006, 116, 637-641; Hoist, B.; Schwartz, T. W. *Trends Pharmacol. Sci.* 2004, 25, 113-117; Holst, B.; Holliday, N. D.; Bach, A.; Elling, C. E.; Cox, H. M.; Schwartz. T. W. *J. Biol. Chem.* 2004, 279, 53806-53817; Hoist, B.; Cyganikiewicz, A.; Jensen, T. H.; Ankersen, M.; Schwartz, T. W. *Mol. Endocrinol.* 2003, 17, 2201-221.) The recent observation that humans possessing a mutation in the ghrelin receptor that impairs constitutive activity are of short stature suggests the importance of the constitutive activity to the normal in vivo function of this receptor. (Pantel, J.; Legendre. M. Cabrol, S.; et al. *J. Clin. Invest.* 2006, 116, 760-768.)

The vast majority of reported approaches to exploiting the ghrelin receptor for therapeutic purposes have focused on modulating metabolic functions. Similarly, the vast majority of literature on GHS focuses on conditions that can be treated via its GH promoting actions. Some embodiments of the invention described herein, in particular, take advantage of selective activation of the ghrelin receptor to provide an avenue for the treatment of diseases characterized by GI dysmotility. The improved GI motility observed with ghrelin demonstrates that ghrelin agonists may be useful in correcting conditions associated with reduced or restricted motility, (Murray, C. D. R.; Kamm, M. A.; Bloom, S. R.; Emmanuel, A. V. *Gastroenterology* 2003, 125, 1492-1502; Fujino, K.; Inui, A.; Asakawa, A.; Kihara, N.; Fujimura, M.; Fujimiya, M. *J. Physiol.* 2003, 550, 227-240; Edholm, T.; Levin, F.; Hellström, P. M.; Schmidt, P. T. *Regul. Pept.* 2004, 121, 25-30; Locatelli, V.; Bresciani, E.; Bulgarelli, I.; Rapetti, D.; Torsello, A.; Rindi, G.; Sibilia, V. Netti, C. *J. Endocrinol. Invest.* 2005, 28, 843-848; Peeters, T. L. *Gut* 2005, 54, 1638-1649; Fruhwald, S.; Holzer, P.; Metzler, H. *Wien. Klin. Wochenschr.* 2008, 120, 6-17.)

Included among these conditions is post-operative ileus. (POI, Luckey, A.; Livingston, E.; Taché, Y. *Arch. Surg.* 2003, 138, 206-214; Baig, M. K.; Wexner, S. D, *Dis. Colon Rectum* 2004, 47, 516-526; Greewood-Van Meerveld, B. *Exp. Opin. Emerging Drugs* 2007, 12, 619-627; Senagore, A. J. *Am. J. Health Syst. Pharm.* 2007, 64, S3-S7; Maron, D. J.; Fry, R. D. *Am. J. Ther.* 2008, 15, 59-65.) POI is defined as the impairment of GI motility that routinely occurs following abdominal, intestinal, gynecological and pelvic surgeries. In the U.S. alone, 2.1 million surgeries annually induce POI, accounting for an economic impact of over $1 billion. POI is considered a deleterious response to surgical manipulation with a variable duration that generally persists for 72 hours. It is characterized by pain, abdominal distention or bloating, nausea and vomiting, accumulation of gas and fluids in the bowel, and delayed passage of stool. Patients are neither able to tolerate oral feeding nor to have bowel movements until gut function returns. POI leads to numerous undesirable consequences, including increased patient morbidity, the costly prolongation of hospital stays and, further, is a major cause of hospital readmission. In addition, opiate drugs given as analgesics after surgery exacerbate this condition due to their well-recognized side effect of inhibiting bowel function.

Surgical manipulation of the stomach or intestine causes a disorganization of the gut-brain signaling pathways, impairing GI activity and triggering PO. Ghrelin acts locally in the stomach to stimulate and coordinate the firing of vagal afferent neurons and thereby modulate gut motility. Thus, ghrelin accelerates gastric emptying in humans (Peeters, T. L. *Curr. Opin. Pharmacol.* 2006, 6, 553-558; Tack, J.; Depoortere, I.; Bisschops, R.; Delporte, C.; Coulie, B.; Meulemans, A.; Janssens, J.; Peeters, T. *Gut* 2006, 55, 327-333; Inui, A., Asakawa, A.; Bowers, C. Y.; Mantovani, G.; Laviano, A.; Meguid, M. M.; Fujimiya, M. *FASEB J.* 2004, 18, 439-456; Peeters, T. L. *J. Physiol. Pharmacol.* 2003, 54(Supp. 4), 95-103.) and is a potent agent proven to treat POI in animal models. (Trudel, L.; Tomasetto, C.; Rio, M. C.; Bouin, M.; Plourde, V.; Eberling, P.; Poitras, P. *Am. J. Physiol.* 2002, 282, G948-G952; Trudel, L.; Bouin, M.; Tomasetto, C.; Eberling, P.; St-Pierre, S.; Bannon, P.; L'Heureux, M. C.; Poitras, P. *Peptides* 2003, 24, 531-534; De Winter, B. Y.; De Man, J. G.; Seerden, T. C.; Depoortere, I.; Herman, A. G.; Peeters, T. L.; Pelckmans, P. A. *Neurogastroenterol. Motil.* 2004, 16, 439-446.) Ghrelin agonists duplicate the effects of ghrelin, thus targeting directly the underlying cause of POI to accelerate normalization of gut function and enable more rapid discharge from the hospital. (Kitazawa, T.; De Smet, B.; Verbeke, K.; Depoortere, I.;

Peeters, T. L. *Gut* 2005, 54, 1078-1084; Poitras, P.; Polvino, W. J.; Rocheleau, B. *Peptides* 2005, 26, 1598-1601.) The reported anti-inflammatory actions of ghrelin may also play a role in ameliorating this condition. (Granado, M.; Priego, T.; Martin, A. I.; Villanua, M. A.; Lopez-Calderon, A. *Am. J. Physiol. Endocrinol. Metab.* 2005, 288, E486-E492; Iseri, S. O.; Sener, G.; Yuksel, M.; Contuk, G.; Cetinel, S.; Gedik, N.; Ycgen, B. C. *J. Endocrinol* 2005, 187, 399-406.)

Intravenous administration is often the preferred route of treatment for POI due to the impaired GI motility in these patients that impedes oral therapy. No agent is currently approved by the U.S. FDA specifically for the treatment of POI.

Another major motility disorder is gastroparesis, a particular problem for both type I and type II diabetics. (Camilleri, M. Advances in diabetic gastroparesis. *Rev. Gastroenterol Disord.* 2002, 2, 47-56; Abell, T. L.; Bernstein, R. K.; Cults, T. *Neurogastrenterol. Motil.* 2006, 18, 263-283; Camilleri, N. *New Eng. J. Med.* 2007, 356, 820-829.) Gastroparesis ("stomach paralysis") is a syndrome characterized by delayed gastric emptying in the absence of any mechanical obstruction. It is variably characterized by abdominal pain, nausea, vomiting, weight loss, anorexia, early satiety, malnutrition, dehydration, gastroesophageal reflux, cramping and bloating. This chronic condition can lead to frequent hospitalization, increased disability and decreased quality of life. (Wang, Y. R.; Fisher, R. S.; Parkman, H. P. *Am. J. Gastro.* 2007, 102, 1-10.) Severe, symptomatic gastroparesis is common in individuals suffering from diabetes, affecting from 5-10% of diabetics for a total patient population of 1 million in the U.S. alone. Neuropathy is a frequent, debilitating complication of diabetes. Visceral neuropathy results in GI dysfunction, especially involving the stomach, and leading to impaired gastric motility. Ghrelin promotes gastric emptying both by stimulating the vagus nerve and via direct prokinetic action at the gastric mucosa. Moreover, recent clinical studies indicate that intravenous administration of the natural ghrelin peptide is an effective acute therapy in diabetic gastroparesis patients. (Binn, M.; Albert, C.; Gougeon, A.; Maerki, H.; Coulie, B.; Lemoyne, M.; Rabasa Lhoret, R.; Tomasetto, C.; Poitras, P. *Peptides* 2006, 27, 1603-1606; Murray, C. D. R.; Martin, N. M.; Patterson, M.; Taylor, S.; Ghatei, M. A.; Kamm, M. A.; Johnston, C.; Bloom, S. R.; Emmanuel, A. V. *Gut* 2005, 54, 1693-1698; Tack, J.; Depoortere, I.; Bisschops, R.; Verbeke, K.; Janssens, J.; Peeters, T. *Aliment. Pharmacol. Ther.* 2005, 22, 847-853.)

A ghrelin agonist would therefore be highly effective in overcoming the fundamental motility barrier faced by gastroparesis patients and correcting this condition. As with POI, no accepted or efficacious therapy for diabetic gastroparesis is available and most current therapies aim to provide only symptomatic relief. Further, many of the therapeutics in development have a mechanism of action similar to earlier products that have failed in this indication. Surgical procedures may ameliorate the disease process, but offer no possibility of cure.

Post-surgical gastroparesis syndrome is a complication resulting from surgery characterized by delayed gastric emptying, postprandial nausea and vomiting, and abdominal pain. (Eckhauser, F. E., et al. *Am. Surg.* 1998, 64, 711-717; Tanaka, M. *Surg. Today* 2005, 35, 345-350.) These surgeries include gastrectomy, pancreato-duodenectomy, gastrojejunostomy in patients with pancreatic cancer and gastric surgery, as well as in patients with liver cirrhosis. (Doberneck, R. C.; Berndt, G. A. Arch. *Surg.* 1987, 122, 827-829; Bar-Natan, M.; Larson, G. M.; Stephens, G.; Massey, T. *Am. J. Surg.* 1996, 172, 24-28; Cohen, A. M.; Ottinger, L. W. *Ann. Surg.* 1976, 184, 689-696; Isobe, H.; Sakai, H.; Satoh, M.; Sakamoto, S.; Nawata, H. *Dig. Dis. Sci.* 1994, 39, 983-987.) The only reported pharmaceutical agents shown to be useful for this syndrome are cisapride and erythromycin. (Takeda, T.; Yoshida, J.; Tanaka, M.; Matsunaga, H.; Yamaguchi, K.; Chijiiwa, K. *Ann. Surg.* 1999, 229, 223-229; Heidenreich, A.; Wille, S.; Hofmann, R. J. *Urology* 2000, 163, 545.) However, cisapride was removed from the market due, at least in part, to the appearance of life-threatening cardiac arythmia side effects. Further, erythromycin is not a desirable treatment due to the antibiotic activity potentially giving rise to resistance should it be used for non-infective purposes.

Opioid-induced bowel dysfunction (OBD, Kurz, A.; Sessler, D. J. *Drugs* 2003, 63, 649-671.) is the term applied to the confluence of symptoms involving the reduced GI motility that results from treatment with opioid analgesics. Approximately 40-50% of patients taking opioids for pain control experience OBD. It is characterized by hard, dry stools, straining, incomplete evacuation, bloating, abdominal distension and increased gastric reflux. In addition to the obvious short-term distress, this condition leads to physical and psychological deterioration in patients undergoing long-term opioid treatment. Further, the dysfunction can be so severe as to become a dose-limiting adverse effect that actually prevents adequate pain control. As with POI, a ghrelin agonist can be expected to counteract the dysmotility resulting from opioid use.

Two less common syndromes may also be helped through the GI motility stimulation effects of ghrelin and ghrelin agonists. Short bowel syndrome is a condition that occurs after resection of a substantial portion of small intestine and is characterized by malnutrition. Patients are observed to have decreased ghrelin levels resulting from loss of the ghrelin-producing neuroendocrine cells of the intestine. It is possible the short bowel feeds back on the release of the hormone. (Krsek, M.; Rosicka. M.; Haluzik, M.; et al. *Endocr. Res.* 2002, 28, 27-33.) Chronic intestinal pseudo-obstruction is a syndrome defined by the presence of chronic intestinal dilation and dysmotility in the absence of mechanical obstruction or inflammation. Both genetic and acquired causes are known to result in this disorder, which affects high numbers of individuals worldwide annually. (Hirano, I.; Pandolfino, J. *Dig. Dis.* 2000, 18, 83-92.)

Other conditions and disorders that could be addressed through stimulation of the ghrelin receptor are: constipation such as associated with the hypomotility phase of irritable bowel syndrome (IBS), delayed gastric emptying associated with wasting conditions, gastroesophageal reflux disease (GERD), gastric ulcers (Sibilia, V.; Muccioli, G.; Deghenghi, R.; Pagani, F.; DeLuca, V.; Rapetti, D.; Locatelli, V.; Netti, C. *J. Neuroendocrinol.* 2006, 18, 122-128; Sibilia, V.; Rindi, G.; Pagani, F.; Rapetti, D.; Locatelli, V.; Torsello, A.; Campanini, N.; Degenghi, R.; Netti, C. *Endocrinology* 2003, 144, 353-359.) and Crohn's disease. Ghrelin and gbrelin agonists also have been described as treatments for nausea, emesis or symptoms thereof. (U.S. Pat. Appl. Pub. No. 2005/277677; Rudd, J. A.; Ngan, M. P.; Wai, M. K.; King, A. G.; Witherington, J.; Andrews, P. L. R.; Sanger, G. J. *Neurosci. Lett.* 2006, 392, 79-83.)

Additionally, GI dysmotility is a significant problem in other mammals as well. For example, the motility dysfunction termed ileus or colic is the number one cause of mortality among horses. Further, ileus is one of the most common complications of equine intestinal surgery, in other words, post-operative ileus. This condition may also have a non-surgical etiology. Some horses may be predisposed to ileus based upon the anatomy and functioning of their digestive tract. Virtually any horse is susceptible to colic with only minor differences based upon age, sex and breed. Additionally, ileus may affect other animals, for example canines. (Roussel, A. J., Jr.; Cohen, N. D.; Hooper, R. N.; Rakestraw, P. C. *J. Am Vet. Med. Assoc.* 2001, 219, 72-78; Van Hoogmoed, L. M.; Nieto, J. E.; Snyder, J. R.; Harmon, F. A. *Vet. Surg.* 2004, 33, 279-285.)

Drug-induced adverse reactions are a well-known complication of all types of pharmacotherapy. Gastrointestinal side effects are among the most common complication experienced with pharmaceuticals, appearing in 20-40% of all cases. (Lewis, J. H. *Am. J. Gastroenterol* 1986, 81, 819-834; Henry, D. A.; Ostapowicz, G.; Robertson, *J. Cin. Gastroenterol.* 1994, 8, 271-300.) Most seriously, an estimated 25% of drug-induced reactions in hospitalized patients involve the GI tract with potentially fatal outcomes in a small percentage of cases. (Stewart, R. B.; Cluff, L. E. *Am. J. Dig. Dis.* 1974, 19, 1-7.) Side effects can affect all portions of the GI tract. (Gore, R. M.; Levine, M. S.; Ghahremani, G. G. *Abdom. Imaging* 1999, 24, 9-16; Neitlich, J. D.; Burrell, M. I. *Abdom. Imaging* 1999, 24, 17-22; Neitlich, J. D.; Burrell, M. I. *Abdom. Imaging* 1999, 24, 23-38.) Such side effects can often only be addressed through reducing doses, thus often decreasing the efficacy of the medication. Additionally, patients often simply stop taking their medicines due to experiencing these side effects.

GI side effects are common in many established pharmaceutical classes, including anti-cholinergic agents (e.g. atropine, benzotropine, hyoscine, propantheline, scopolamine, trihexyphenidyl), tricyclic antidepressants (e.g. phenothiazines, amitriptyline, nortryptyline), monoamine uptake blocker antidepressants (e.g. desipramine, fluoxetine, citalopram, nomifensine), other psychoactive medications, cancer chemotherapy agents (e.g. vincristine), adrenergic agonists for hypertension, particularly β-agonists and $\alpha_2$-agonists, (e.g. isoproterenol, salbutamol, lidamidine, clonidine), dopaminergic agents (e.g. levodopa, bromocriptine, apomorphine), antimalarials (e.g. chloroquine, mepacrine), antispasmodic (e.g. pavatrine) and many other agents (e.g. zonisamide, pergolide, ibudilast, mexiletine, acarbose, sodium valproate, hexamethonium, alendronate).

In addition, many newer medications, although promising improved therapies for a range of diseases, are also subject to GI side effects. Among these are agonists of the glucagon-like peptide 1 (GLP-1), amylin and peptide YY (PYY) receptors that are very useful for treatment of diabetes and/or other metabolic disorders. Other pharmaceutical classes that exhibit GI side effects are proteasome inhibitors, a new chemotherapeutic, often as an adjunct therapy, for cancer, leukotriene receptor antagonists for asthma and other inflammatory diseases (e.g. pranlukast, Garcia, M.; Nakabayashi, T.; Mochiki, E.; Naga, N.; Pacheco, I.; Suzuki, T.; Kuwano, H. *Dig. Dis. Sci.* 2004, 49, 1228-1235), phosphodiesterase-5 (PDE-5) inhibitors (e.g. sildenafil: Dishy, V.; Pour, M. C.; Feldman, L. *Clin. Pharm. Ther.* 2004, 76, 281-286), and nicotinic acetylcholine receptors modulators (Mandl, P.; Kiss, J. P. *Brain Res. Bull.* 2007, 72, 194-200).

A number of new pharmaceutical treatments for metabolic disorders have been introduced or are in development. Unfortunately, many of these exhibit gastrointestinal (GI) side effects which can result in reduced efficacy, poor patient compliance and even removal of patients from medication.

For example, GLP-1 agonists such as exenatide are among the most effective new agents for treatment of diabetes. However, this mechanism of action also results in a significant reduction in gastric emptying. (Nauck, M. A.; Niedereichholz, U.; Ettler, R.; Holst, J. J.; Orskov, C.; Ritzel, R.; Schumiegel, W. H. *Am. J. Physiol.* 1997, 273, E981-E988; Tolessa, T.; Gutniak, M.; Holst, J. J.; Efendic, S.; Hellstrom, P. M. *J. Clin. Invest,* 1998, 102, 764-774; Little, T. J.; Pilichiewicz, A. N.; Russo, A.; Phillips, L.; Jones, K. L.; Nauck, M. A.; Wishart, J.; Horowitz, M.; Feinle-Bisset, C. J. *Clin. Endocrinol. Metab.* 2006, 91, 1916-1923; Barnett, A. *Exp. Opin. Pharmacother.* 2007, 8, 2593-2608.) Since delayed gastric emptying, or gastroparesis, is already a well-established problem for diabetic patients, this side effect exacerbates an already difficult situation.

Analogously, pramlintide has been introduced as an amylin agonist that is also useful for the treatment of diabetes. Unfortunately, inherent in its mechanism of action is reduced gastric emptying. (Young, A. *Adv. Pharmacol.* 2005, 52, 99-121.)

Peptide YY agonists likewise have potential utility for the treatment of metabolic disorders, but also reduce gastric emptying. (Chelikani, P. K.; Haver, A. C.; Reidelberger, R. D: *Am. J. Physiol.* 2004, 287, R1064-R1070.)

Similarly, proteasome inhibitors have been introduced as a useful therapy, either alone or in combination with other chemotherapeutic agents for treatment of a wide variety of hyperproliferative disorders, including many different types of cancers. However, one of these drugs, bortezomib, also results in delayed GI transit. (Perfetti, V.; Palladini, G.; Brunetti, L.; Sgarella, A.; Brugnatelli, S.; Gobbi P. O.; Corazza, G. R. *Eur. J. Gastroenterol. Hepatol.* 2007, 19, 599-601.)

Ghrelin agonists (as growth hormone secretagogues, GHS), but not those described in the present invention, have been employed in combination with a variety of other therapeutic agents, although not specifically to counteract drug-induced GI side effects. GHS in combination with selective estrogen receptor modulators (SERM) have been reported for treatment of muscoskeletal frailty (WO 99/65486, WO 99/65488, GB 2324726). EP 1149583 discusses the use of GHS with corticotrophin releasing factor (CRF) antagonists as medicaments for osteoporosis and cardiovascular diseases such as congestive heart failure. GHS have been described in combination with antidepressants for improvement in quality of life (WO 01/089570).

A number of combinations of pharmaceutical agents with GHS have been discussed for treating Alzheimer's, including with phosphodiesterase-4 inhibitors (WO 2004/087157), with β-amyloid modifying agents (WO 2004/110443) and p38 kinase inhibitors (WO 2005/058308). U.S. Pat. No. 6,657,063 reports combinations of GHS and $\beta_3$-adrenergic agonists for the treatment of type II diabetes. GHS have been used in combination with GH for cachexia, decreased appetite and to increase food intake (WO 2005/097173; WO 2005/097174). WO 2006/092106 describes the use of a representative GHS, GHRP-6, with epidermal growth factor (EGF) for autoimmune and CNS diseases.

Combinations of other agents have been described for a variety of GI disorders. These include acetylcholinesterase inhibitors with anti-cholinergics agents as a treatment for chronic intestinal pseudo-obstruction (US 2004/082644). WO 2006/005613 discloses dipeptidyl peptidase IV inhibitors, in combination with 5-$HT_3$ and 5-$HT_4$ modulators for GI disorders.

Reports of combinations of drugs specifically for GI motility disorders are known, including 5-$HT_3$ agonists with a second compound to treat diseases characterized by hypomotility (WO 2007/005780). 5-$HT_3$ antagonists and 5-$HT_4$ agonists with a second agent are described in WO 01/041748 and US 2004/092511.

Proton pump inhibitors (PPI) have been reported in combination with prokinetic agents (WO 2005/065664) and with GI motility agents (WO 2004/105795). PPI also have been reported in combination with compounds which modify gastrointestinal motility as an approach to the treatment of gastroesophageal reflux disease (GERD, U.S. Pat. Appl. Publ. No. 2006/0241134). Norcisapride, a prokinetic agent, has been used in combination with PPI and $H_2$-antagonists, such as berberine, (WO 00/051583; WO 00/051584).

There remains, however, a need for additional combinations, such as the pharmaceutical compositions of the present invention, which can address the drug-induced GI side effects from certain drugs as outlined previously.

Importantly, for most of the above conditions, no specific, approved therapeutics exist and most therapies simply address symptomatic relief. However, specific modulation of the ghrelin receptor provides an opportunity to directly target the site of pathophysiological disturbance to better treat the underlying condition and improve clinical outcome. Further, macrocyclic ghrelin agonists have been shown not to stimulate concurrent GH secretion in animal models. (Venkova, K.; Fraser, G.; Hoveyda, H. R.; Greenwood-Van Meerveld, B. *Dig. Dis. Sci.* 2007, 52, 2241-2248.) This separation of the gastrointestinal and GH effects has not previously been reported for any modulators of the ghrelin receptor. However, as already mentioned, the existence of analogues that separate the appetite control and OH modulatory effects associated with ghrelin has been recently reported (Halem, H. A.; Taylor, J. E.; Dong, J. Z.; et al. *Eur. J. Endocrinol.* 2004, 151, S71-S75).

WO 01/00830 discusses short gastrointestinal peptides (SGIP) that secrete growth hormone and also promote GI motility, but these were not shown to be due to action at the ghrelin receptor. Similarly, WO 2007/041278 describes peptide analogues of ghrelin that stimulate GI motility. U.S. Pat. Nos. 6,548,501 and 6,852,722 discuss specific non-peptidic GHS compounds useful for stimulation of GI motility. Similarly, WO 2006/010629, WO 2006/020930 and WO 2006/023608 describe ghrelin agonists (growth hormone secretagogues) for use in GI disorders. Moreover, other endogenous factors are known to stimulate secretion of GH, but do not promote GI motility. Indeed, many actually inhibit this physiological function. Specific receptor agonists such as the compounds of the present invention have much better potential to be selective and effective therapeutic agents.

Intl. Pat. Appl. WO 2006/009645 and WO 2006/009674 describe the use of macrocyclic compounds as ghrelin modulators for use in the treatment of GI disorders. The activity of one of these compounds in a rat model of POI has been reported. (Venkova, K.; Fraser, G.; Hoveyda, H. R.; Greenwood-Van Meerveld, B. *Dig. Dis. Sci.* 2007, 52, 2241-2248.) These macrocyclic compounds are structurally distinct from other compounds that have been found to interact at the ghrelin receptor as agonists. For example, significant work was devoted to the development of potent and selective GHS with a number of small molecule derivatives now being known as has been recently summarized, (Carpino, P. *Exp. Opin. Ther. Patents* 2002, 12, 1599-1618.) Specific GHS are described in the following: Intl. Pat. Appl. Publ. Nos. WO 89/07110; WO 89/07111; WO 92/07578; WO 93/04081; WO 94/11012; WO 94/13696; WO 94/19367; WO 95/11029; WO 95/13069; WO 95/14666; WO 95/17422; WO 95/17423; WO 95/34311; WO 96/02530; WO 96/15148; WO 96/22996; WO 96/22997; WO 96/24580; WO 96/24587; WO 96/32943; WO 96/33189; WO 96/35713; WO 96/38471; WO 97/00894; WO 97/06803; WO 97/07117; WO 97/09060; WO 97111697; WO 97/15191; WO 97/15573; WO 97/21730; WO 97/22004; WO 97/22367; WO 97/22620; WO 97/23508; WO 97/24369; WO 97/34604; WO 97/36873; WO 97/38709; WO 97/40023; WO 97/40071; WO 97/41878; WO 97/41879; WO 97/43278; WO 97/44042; WO 97/46252; WO 98/03473; WO 98/10653; WO 98/18815; WO 98/22124; WO 98/46569; WO 98/51687; WO 98/58947; WO 98/58948; WO 98/58949; WO 98/58950; WO 99/08697; WO 99/08699; WO 99/09991; WO 99/36431; WO 99/39730; WO 99/45029; WO 99/58501; WO 99/64456; WO 99/65486, WO 99/65488; WO 00/01726; WO 00/10975; WO 00/48623; WO 00/54729; WO 01/47558; WO 01/92292; WO 01/96300; WO 01/97831; WO 2004/021984; WO 2005/039625; WO 2005/046682; WO 2005/070884; WO 2006/044359; U.S. Pat. Nos. 3,239,345; 4,036,979; 4,411,890; 5,492,916; 5,494,919; 5,559,128; 5,663,171; 5,721,250; 5,721,251; 5,723,616; 5,726,319; 5,767,124; 5,798,337; 5,830,433; 5,919,777; 6,034,216; 6,548,501; 6,559,150; 6,576,686; 6,639,076; 6,686,359; 6,828,331; 6,861,409; 6,919,315; 7,034,050 and U.S. Pat. Appl. Nos. 2002/0168343; 2003/100494; 2003/130284; 2003/186844; 2005/187237; 2005/233981.

Despite this immense body of work, cyclic compounds have rarely been found to act at the ghrelin receptor. When they have, antagonist activity has been more prevalent. For example, the 14-amino acid compound, vapreotide, an SRIH14 agonist and somatostatin mimetic, was demonstrated to be a ghrelin antagonist. (Deghenghi R, Papotti M. Ghigo E. et al. *Endocrine* 2001, 14, 29-33.) The binding and antagonist activities of analogues of cortistatin, a cyclic neuropeptide known to bind nonselectively to somatostatin receptors, to the growth hormone secretagogue receptor have been reported (Intl. Pat. Appl. WO 03/004518). (Deghenghi R, Broglio F, Papotti M, et al. *Endocrine* 2003, 22, 13-18; Sibilia, V.; Muccioli, G.; Deghenghi, R.; Pagani, F.; DeLuca, V.; Rapetti, D.; Locatelli, V.; Netti, C. *J. Neuroendocrinol.* 2006, 18, 122-128.) In particular, one of these analogues, EP-01492 (cortistatin-8) has been advanced into preclinical studies for the treatment of obesity as a ghrelin antagonist, although a recent study casts doubts on its effectiveness. (Prodam, F.; Benso, A.; Gramaglia, E. Neuropeptides 2008, 42, 89-93.) These compounds exhibit an $IC_{50}$, of 24-33 nM. In addition, these cyclic compounds and their derivatives, plus their use with metal binding agents have been described for their ability to be useful for radiodiagnostic or radiotherapeutic use in the treatment of tumors and acromegaly.

Cyclic and linear analogues of growth hormone 177-191 have been studied as treatments for obesity (WO 99/12969), with one particular compound, AOD9604, having entered the clinic for this indication. A compound already studied that is most similar to the molecules of the present invention is the GHS, G-1203 ($EC_{50}$=0.43 nM), the cyclic peptide analogue of the growth hormone releasing peptide, GHRP-2. (Elias, K. A.; Ingle, G. S.; Burnier, J. P.; Hammonds, G.; McDowell, R. S.; Rawson, T. E.; Somers, T. C.; Stanley, M. S.; Cronin, M. J. *Endocrinol.* 1995, 136, 5694-5699.) However, simplification of this cyclic derivative led to still potent, linear compounds, whereas, for compounds of the invention, linear analogues have been found to be devoid of ghrelin receptor activity.

The macrocyclic compounds of the invention have been shown to possess ghrelin modulating activity, and in particular embodiments, as agonists. Macrocyclic peptidomimetics have been previously described as modulators of the ghrelin receptor and their uses for the treatment of a variety of GI and metabolic disorders summarized (Intl. Pat. Appl. Publ. Nos. WO 2006/009645; 2006/009674; WO 2006/046977; 2006/137974 U.S. Pat. Appl. Publ. Nos. 2006/025566; 2007/0021331; U.S. patent application Ser. No. 11/774,185) One of these compounds has entered the clinic. (Lasseter, K. C.; Shaughnessy, L.; Cummings, D.; et al. *J. Clin. Pharmacol.* 2008, 48, 193-202).

Although binding potency and target affinity are factors in drug discovery and development, also important for development of viable pharmaceutical agents are optimization of pharmacokinetic (PK) and pharmacodynamic (PD) parameters. A focus area for research in the pharmaceutical industry has been to better understand the underlying factors which determine the suitability of molecules in this manner, often colloquially termed its "drug-likeness" (Lipinski, C. A.; Lombardo, F.; Dominy, B. W.; Feeney, P. J. *Adv. Drug Delivery Rev.* 1997, 23, 3-25; Muegge, I. *Med. Res. Rev.* 2003, 23, 302-321; Veber. D. F.; Johnson, S. R.; Cheng, H.-Y.; Smith, B. R.; Ward, K. W.; Kopple, K. D. *J. Med. Chem.* 2002, 45, 2615-2623.) For example, molecular weight, log P, membrane permeability, the number of hydrogen bond donors and acceptors, total polar surface area (TPSA), and the number of rotatable bonds have all been correlated with compounds that have been successful in drug development. Additionally, experimental measurements of plasma protein binding, interaction with cytochrome P450 enzymes, and pharmacokinetic parameters are employed in the pharmaceutical industry to select and advance new drug candidates.

However, these parameters have not been widely explored or reported within the macrocyclic structural class. This lack of information creates challenges in drug development for such molecules. The macrocyclic compounds of the present invention have been found to possess desirable pharmacological characteristics, while maintaining sufficient binding affinity and selectivity for the ghrelin receptor, as illustrated in the Examples presented herein. These combined characteristics make the compounds of the present invention generally more suitable than previously reported macrocycles for development as pharmaceutical agents, particularly for use as orally administered agents or for chronic uses.

SUMMARY OF THE INVENTION

The present invention provides novel conformationally-defined macrocyclic compounds. These compounds can function as modulators, in particular agonists, of the ghrelin (growth hormone secretagogue) receptor (GHS-R1a).

According to aspects of the present invention, the present invention relates to a compound according to formula I:

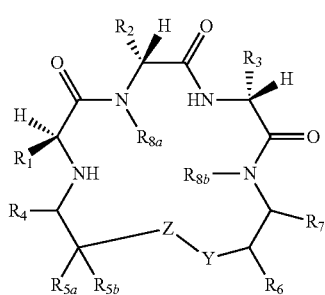

(I)

and pharmaceutically acceptable salts thereof
wherein:
$R_1$ is selected from the group consisting of cycloalkyl, substituted cycloalkyl, lower alkyl and substituted tower alkyl;
$R_2$ is selected from the group consisting of lower alkyl and substituted lower alkyl;
$R_3$ is selected from the group consisting of alkyl, alkyl substituted with hydroxy or carboxy, and alkyl substituted with aryl;
$R_4$, $R_{5a}$, $R_{5b}$, $R_6$, and $R_7$ are independently selected from the group consisting of hydrogen and lower alkyl;
$R_{8a}$ and $R_{8b}$ are independently selected from the group consisting of hydrogen and lower alkyl;

Y is $CR_{9a}R_{9b}$; wherein $R_{9a}$ and $R_{9b}$ are independently selected from the group consisting of hydrogen and lower alkyl;
Z is selected from:

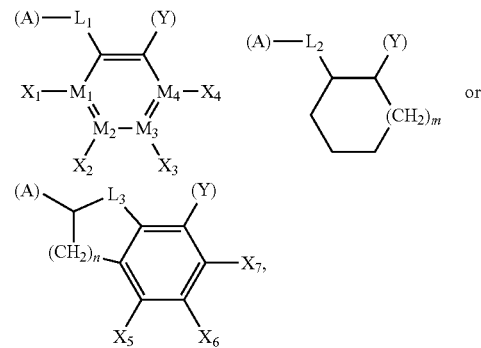

wherein (A) and (Y) indicate the bonds of Z to $CR_{5a}R_{5b}$ and Y of formula I, respectively;
$L_1$, $L_2$ and $L_3$ are independently selected from the group consisting of O, and $CR_{10a}R_{10b}$; wherein $R_{10a}$ and $R_{10b}$ are independently selected from the group consisting of hydrogen and lower alkyl;
$M_1$, $M_2$, $M_3$ and $M_4$ are independently selected from the group consisting of C and N, with the proviso that, at most, one of $M_1$, $M_2$, $M_3$ and $M_4$ is nitrogen;
$X_1$, $X_2$, $X_3$, $X_4$, $X_5$, $X_6$ and $X_7$ are independently selected from the group consisting of hydrogen, halogen, trifluoromethyl, hydroxy, alkoxy and lower alkyl;
m is 0 or 1; and n is 1 or 2.

Aspects of the present invention also provide a compound of formula II:

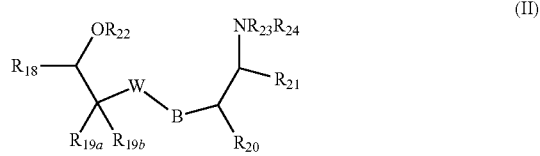

(II)

or an optical isomer, enantiomer or diastereomer thereof wherein:
$R_{18}$, $R_{19a}$, $R_{19b}$, $R_{20}$, and $R_{21}$ are independently selected from the group consisting of hydrogen, lower alkyl and substituted lower alkyl;
$R_{22}$ is selected from the group consisting of hydrogen, alkyl, acyl, sulfonyl and a standard protecting group for a hydroxy functional group;
$R_{23}$ is selected from the group consisting of hydrogen, alkyl, acyl, carboxyalkyl, carboxyaryl, sulfonyl and a standard protecting group for an amine functional group;
$R_{24}$ is selected from the group consisting of hydrogen and alkyl;
B is $CR_{25a}R_{25b}$; wherein $R_{25a}$ and $R_{25b}$ are independently selected from the group consisting of hydrogen and lower alkyl;
W is selected from the group consisting of:

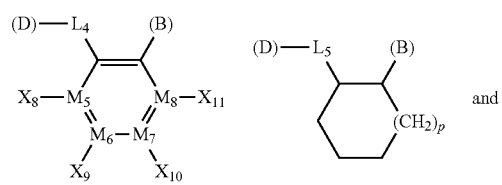

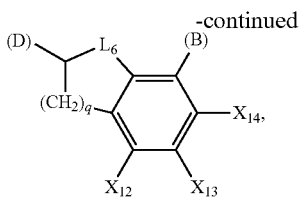

-continued wherein (D) and (B) indicate the bonds of W to $CR_{19a}R_{19b}$ and B of formula II, respectively;

$L_4$, $L_5$ and $L_6$ are independently selected from the group consisting of O, and $CR_{26a}R_{26b}$; wherein $R_{26a}$ and $R_{26b}$ are independently selected from the group consisting of hydrogen and lower alkyl;

$M_5$, $M_6$, $M_7$ and $M_8$ are independently selected from the group consisting of C and N, with the proviso that, at most, one of $M_5$, $M_6$, $M_7$ and $M_8$ is nitrogen;

$X_8$, $X_9$, $X_{10}$, $X_{11}$, $X_{12}$, $X_{13}$ and $X_{14}$ are independently selected from the group consisting of hydrogen, halogen, trifluoromethyl, hydroxy, alkoxy and lower alkyl;

p is 0 or 1; and q is 1 or 2.

Further aspects of the present invention provide a macrocyclic compound including (a) a building block structure; and (b) a compound of formula IT, or a derivative thereof and methods of using a compound of formula II to synthesize a compound of formula I.

Aspects of the present invention further provide pharmaceutical compositions including a compound of formula I or II and a pharmaceutically acceptable carrier, excipient or diluent. In some embodiments, the pharmaceutical compositions include a ghrelin receptor agonist and at least one of a GLP-1 receptor agonist, an amylin receptor agonist, a peptide YY (PYY) receptor agonist and a proteasome inhibitor along with a pharmaceutically acceptable carrier, excipient or diluent.

Aspects of the present invention provide methods of treating a gastrointestinal disorder, a metabolic or endocrine disorder, a cardiovascular disorder, a central nervous system disorder, an inflammatory disorder, a bone disorder or a hyperproliferative disorder, including administering to a subject in need thereof an effective amount of a compound of formula I.

Additional aspects of the present invention provide kits comprising one or more containers containing pharmaceutical dosage units comprising an effective amount of one or more compounds of the present invention packaged with optional instructions for the use thereof.

Aspects of the present invention further provide methods of stimulating gastrointestinal motility, modulating GHS-R1a receptor activity in a mammal and/or treating a gastrointestinal disorder comprising administering to a subject in need thereof an effective amount of a modulator that modulates a mammalian GHS-R1a receptor. In still other embodiments, the modulator is a compound of formula I.

Additional aspects of the present invention provide methods of diagnosing tumors and/or acromegaly, comprising administering compounds of the present invention and a radiolabeled metal binding agent and detecting the binding of the composition to a biological target, and treating tumors and/or acromegaly comprising administering a therapeutically effective amount of a composition comprising a compound of the present invention.

Other aspects of the present invention provide administering compounds of the present invention, such as those of formula I, to treat a subject suffering from reduced or dysfunctional gastrointestinal motility caused by a particular agent(s) such as a medicament, pharmaceutical or pharmaceutical composition. In some embodiments, the particular agent(s) have been employed to treat the subject for a metabolic, hyperproliferative or other disorder. Additionally, the compounds of the present invention may be used to prevent reduced or dysfunctional gastrointestinal motility that may be caused by a particular agent(s).

Further aspects of the present invention relate to methods of making the compounds of formula I or II.

Aspects of the present invention further relate to methods of preventing and/or treating disorders described herein, in particular, gastrointestinal disorders, including post-operative ileus, gastroparesis, such as diabetic and post-surgical gastroparesis, opioid-induced bowel dysfunction, chronic intestinal pseudo-obstruction, short bowel syndrome, emesis such as caused by cancer chemotherapy, constipation such as associated with the hypomotility phase of irritable bowel syndrome (IBS), delayed gastric emptying associated with wasting conditions, gastroesophageal reflux disease (GERD), gastric ulcers. Crohn's disease, gastrointestinal disorders characterized by dysmotility and other diseases and disorders of the gastrointestinal tract.

In particular embodiments, the gastrointestinal disorder is postoperative ileus, gastroparesis, opioid-induced bowel dysfunction, chronic intestinal pseudo-obstruction, acute colonic pseudo-obstruction (Ogilvie's syndrome), short bowel syndrome, emesis, constipation-predominant irritable bowel syndrome (IBS), chronic constipation, cancer-associated dyspepsia syndrome, delayed gastric emptying, gastrointestinal dysfunction or delayed gastric emptying in patients with Parkinson's disease, gastrointestinal dysfunction or delayed gastric emptying in myotonic muscular dystrophy, gastrointestinal dysfunction or delayed gastric emptying in patients with scerloderma, gastroesophageal reflux disease (GERD), gastric ulcers, or Crohn's disease.

The present invention also relates to compounds of formula I and/or II used for the preparation of a medicament for prevention and/or treatment of the disorders described herein.

The foregoing and other aspects of the present invention are explained in greater detail in the specification set forth below.

DETAILED DESCRIPTION

Figure 1:
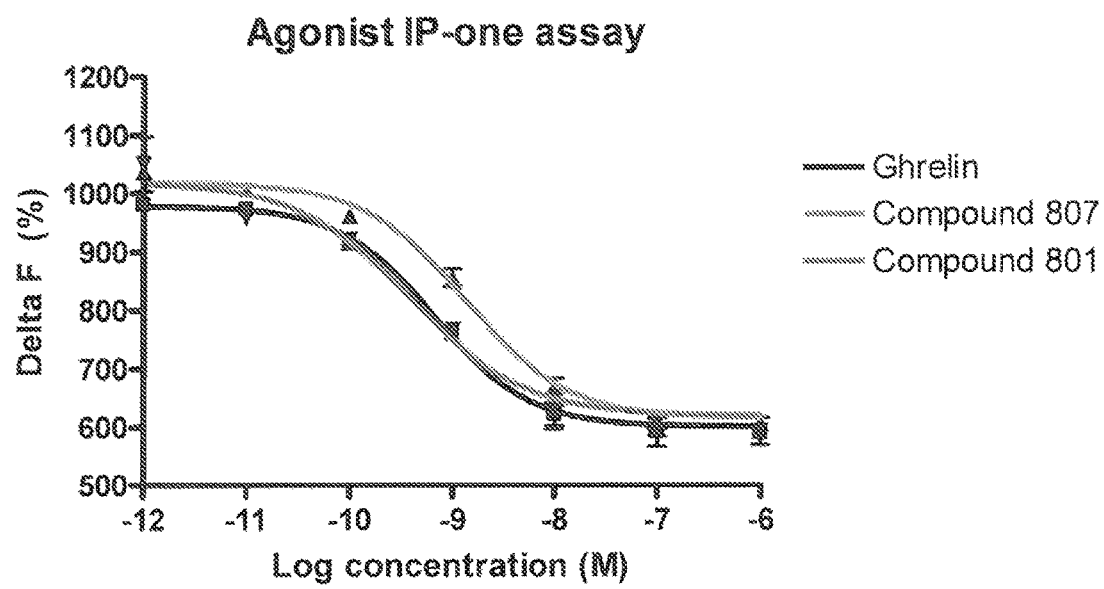
FIG. 1 shows a concentration-response graph for activation of the ghrelin receptor mediated signaling pathway with an exemplary compound of the present invention.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Additionally, as used herein, the term "and/or" includes any and all combinations of one or more of the associated listed items and may be abbreviated as "/".

Unless otherwise defined, all technical and scientific terms used herein have the same meaning as commonly understood by one of ordinary skill in the art to which this invention belongs.

All publications, U.S. patent applications, U.S. patents and other references cited herein are incorporated by reference in their entireties.

The term "alkyl" refers to straight or branched chain saturated or partially unsaturated hydrocarbon groups having from 1 to 20 carbon atoms, in some instances 1 to 8 carbon atoms. The term "lower alkyl" refers to alkyl groups containing 1 to 6 carbon atoms. Examples of alkyl groups include, but are not limited to, methyl, ethyl, isopropyl, tert-butyl, 3-hexenyl, and 2-butynyl. By "unsaturated" is meant the presence of 1, 2 or 3 double or triple bonds, or a combination of the two. Such alkyl groups may also be optionally substituted as described below.

When a subscript is used with reference to an alkyl or other hydrocarbon group defined herein, the subscript refers to the number of carbon atoms that the group may contain. For example, $C_2$-$C_4$ alkyl indicates an alkyl group with 2, 3 or 4 carbon atoms.

The term "cycloalkyl" refers to saturated or partially unsaturated cyclic hydrocarbon groups having from 3 to 15 carbon atoms in the ring, in some instances 3 to 7, and to alkyl groups containing said cyclic hydrocarbon groups. Examples of cycloalkyl groups include, but are not limited to, cyclopropyl, cyclopropylmethyl, cyclopentyl, 2-(cyclohexyl)ethyl, cycloheptyl, and cyclohexenyl. Cycloalkyl as defined herein also includes groups with multiple carbon rings, each of which may be saturated or partially unsaturated, for example decalinyl, [2.2.1]-bicycloheptanyl or adamantanyl. All such cycloalkyl groups may also be optionally substituted as described below.

The term "aromatic" refers to an unsaturated cyclic hydrocarbon group having a conjugated pi electron system that contains 4n+2 electrons where n is an integer greater than or equal to 1. Aromatic molecules are typically stable and are depicted as a planar ring of atoms with resonance structures that consist of alternating double and single bonds, for example benzene or naphthalene.

The term "aryl" refers to an aromatic group in a single or fused carbocyclic ring system having from 6 to 15 ring atoms, in some instances 6 to 10, and to alkyl groups containing said aromatic groups. Examples of aryl groups include, but are not limited to, phenyl, 1-naphthyl, 2-naphthyl and benzyl. Aryl as defined herein also includes groups with multiple aryl rings which may be fused, as in naphthyl and anthracenyl, or unfused, as in biphenyl and terphenyl. Aryl also refers to bicyclic or tricyclic carbon rings, where one of the rings is aromatic and the others of which may be saturated, partially unsaturated or aromatic, for example, indanyl or tetrahydronaphthyl (tetralinyl). All such aryl groups may also be optionally substituted as described below.

The term "heterocycle" or "heterocyclic" refers to saturated or partially unsaturated monocyclic, bicyclic or tricyclic groups having from 3 to 15 atoms, in some instances 3 to 7, with at least one heteroatom in at least one of the rings, said heteroatom being selected from O, S or N. Each ring of the heterocyclic group can contain one or two O atoms, one or two S atoms, one to four N atoms, provided that the total number of heteroatoms in each ring is four or less and each ring contains at least one carbon atom. The fused rings completing the bicyclic or tricyclic heterocyclic groups may contain only carbon atoms and may be saturated or partially unsaturated. The N and S atoms may optionally be oxidized and the N atoms may optionally be quaternized. Heterocyclic also refers to alkyl groups containing said monocyclic, bicyclic or tricyclic heterocyclic groups. Examples of heterocyclic rings include, but are not limited to, 2- or 3-piperidinyl, 2- or 3-piperazinyl, 2- or 3-morpholinyl. All such heterocyclic groups may also be optionally substituted as described below The term "heteroaryl" refers to an aromatic group in a single or fused ring system having from 5 to 15 ring atoms, in some instances 5 to 10, which have at least one heteroatom in at least one of the rings, said heteroatom being selected from O, S or N. Each ring of the heteroaryl group can contain one or two O atoms, one or two S atoms, one to four N atoms, provided that the total number of heteroatoms in each ring is four or less and each ring contains at least one carbon atom. The fused rings completing the bicyclic or tricyclic groups may contain only carbon atoms and may be saturated, partially unsaturated or aromatic. In structures where the lone pair of electrons of a nitrogen atom is not involved in completing the aromatic pi electron system, the N atoms may optionally be quaternized or oxidized to the N-oxide. Heteroaryl also refers to alkyl groups containing said cyclic groups. Examples of monocyclic heteroaryl groups include, but are not limited to pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, benzopyranyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to carbazolyl, benzindolyl, phenanthrollinyl, acridinyl, phenanthridinyl, and xanthenyl. All such heteroaryl groups may also be optionally substituted as described below.

The term "hydroxy" refers to the group —OH.

The term "alkoxy" refers to the group —OR$_a$, wherein R$_a$ is alkyl, cycloalkyl or heterocyclic. Examples include, but are not limited to methoxy, ethoxy, tert-butoxy, cyclohexyloxy and tetrahydropyranyloxy.

The term "aryloxy" refers to the group —OR$_b$ wherein R$_b$ is aryl or heteroaryl. Examples include, but are not limited to phenoxy, benzyloxy and 2-naphthyloxy.

The term "acyl" refers to the group —C(=O)—R$_c$ wherein R$_c$ is alkyl, cycloalkyl, heterocyclic, aryl or heteroaryl. Examples include, but are not limited to, acetyl, benzoyl and furoyl.

The term "amino acyl" indicates an acyl group that is derived from an amino acid.

The term "amino" refers to an —NR$_d$R$_e$ group wherein R$_d$ and R$_e$ are independently selected from the group consisting of hydrogen, alkyl, cycloalkyl, heterocyclic, aryl and heteroaryl. Alternatively, R$_d$ and R$_e$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "amido" refers to the group —C(=O)—NR$_f$R$_g$ wherein R$_f$ and R$_g$ are independently selected from the group consisting of hydrogen, alkyl, cycloalkyl, heterocyclic, aryl and heteroaryl. Alternatively, R$_f$ and R$_g$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "amidino" refers to the group —C(=NR$_h$)NR$_i$R$_j$ wherein R$_h$ is selected from the group consisting of hydrogen, alkyl, cycloalkyl, heterocyclic, aryl and heteroaryl; and R$_i$ and R$_j$ are independently selected from the group consisting of hydrogen, alkyl, cycloalkyl, heterocyclic, aryl and heteroaryl. Alternatively, R$_i$ and R$_j$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "carboxy" refers to the group —CO$_2$H.

The term "carboxyalkyl" refers to the group —CO$_2$R$_k$, wherein R$_k$ is alkyl, cycloalkyl or heterocyclic.

The term "carboxyaryl" refers to the group —CO$_2$R$_m$, wherein R$_m$ is aryl or heteroaryl.

The term "cyano" refers to the group —CN.

The term "formyl" refers to the group —C(=O)H, also denoted —CHO.

The term "halo," "halogen" or "halide" refers to fluoro, fluorine or fluoride, chloro, chlorine or chloride, bromo, bromine or bromide, and iodo, iodine or iodide, respectively.

The term "oxo" refers to the bivalent group =O, which is substituted in place of two hydrogen atoms on the same carbon to form a carbonyl group.

The term "mercapto" refers to the group —SR$_n$ wherein R$_n$ is hydrogen, alkyl, cycloalkyl, heterocyclic, aryl or heteroaryl.

The term "nitro" refers to the group —NO$_2$.

The term "trifluoromethyl" refers to the group —CF$_3$.

The term "sulfinyl" refers to the group —S(=O)R$_p$, wherein R$_p$ is alkyl, cycloalkyl, heterocyclic, aryl or heteroaryl.

The term "sulfonyl" refers to the group —S(=O)$_2$—R$_{q1}$ wherein R$_{q1}$ is alkyl, cycloalkyl, heterocyclic, aryl or heteroaryl.

The term "aminosulfonyl" refers to the group —NR$_{q2}$—S(=O)$_2$—R$_{q3}$ wherein R$_{q2}$ is hydrogen, alkyl, cycloalkyl, heterocyclic, aryl or heteroaryl; and R$_{q3}$ is alkyl, cycloalkyl, heterocyclic, aryl or heteroaryl.

The term "sulfonamido" refers to the group —S(=O)$_2$—NR$_r$R$_s$ wherein R$_r$ and R$_s$ are independently selected from the group consisting of hydrogen, alkyl, cycloalkyl, heterocyclic, aryl or heteroaryl. Alternatively, R$_r$ and R$_s$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "carbamoyl" refers to a group of the formula —N(R$_t$)—C(=O)—OR$_u$ wherein R$_t$ is selected from hydrogen, alkyl, cycloalkyl, heterocyclic, aryl or heteroaryl; and R$_u$ is selected from alkyl, cycloalkyl, heterocyclic, aryl or heteroaryl.

The term "guanidino" refers to a group of the formula —N(R$_v$)—C(=NR$_w$)—NR$_x$R$_y$, wherein R$_v$, R$_w$, R$_x$ and R$_y$ are independently selected from hydrogen, alkyl, cycloalkyl, heterocyclic, aryl or heteroaryl. Alternatively, R$_x$ and R$_y$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "ureido" refers to a group of the formula —N(R$_z$)—C(=O)—NR$_{aa}$R$_{bb}$ wherein R$_z$, R$_{aa}$ and R$_{bb}$ are independently selected from hydrogen, alkyl, cycloalkyl, heterocyclic, aryl or heteroaryl. Alternatively, R$_{aa}$ and R$_{bb}$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

The term "substituted" when used with the terms alkyl, cycloalkyl, heterocyclic, aryl and heteroaryl refers to an alkyl, cycloalkyl, heterocyclic, aryl or heteroaryl group having one or more of the hydrogen atoms of the group replaced by substituents independently selected from unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, halo, oxo, mercapto, sulfinyl, sulfonyl, sulfonamido, amidino, carbamoyl, guanidino, ureido and groups of the formulas —$NR_{cc}C(=O)R_{dd}$, —$NR_{ee}C(=NR_{ff})R_{gg}$, —$OC(=O)NR_{hh}R_{ii}$, —$OC(=O)R_{jj}$, —$OC(=O)OR_{kk}$, —$NR_{mm}SO_2R_{nn}$, or —$NR_{pp}SO_2NR_{qq}R_{rr}$ wherein $R_{cc}$, $R_{dd}$, $R_{ee}$, $R_{ff}$, $R_{gg}$, $R_{hh}$, $R_{ii}$, $R_{jj}$, $R_{mm}$, $R_{pp}$, $R_{qq}$ and $R_{rr}$ are independently selected from hydrogen, unsubstituted alkyl, unsubstituted cycloalkyl, unsubstituted heterocyclic, unsubstituted aryl or unsubstituted heteroaryl; and wherein $R_{kk}$ and $R_{nn}$ are independently selected from unsubstituted alkyl, unsubstituted cycloalkyl, unsubstituted heterocyclic, unsubstituted aryl or unsubstituted heteroaryl. Alternatively, $R_{gg}$ and $R_{hh}$, $R_{jj}$ and $R_{kk}$ or $R_{pp}$ and $R_{qq}$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N. In addition, the term "substituted" for aryl and heteroaryl groups includes as an option having one of the hydrogen atoms of the group replaced by cyano, nitro or trifluoromethyl.

A substitution is made provided that any atom's normal valency is not exceeded and that the substitution results in a stable compound. Generally, when a substituted form of a group is present, such substituted group is preferably not further substituted or, if substituted, the substituent comprises only a limited number of substituted groups, in some instances 1, 2, 3 or 4 such substituents.

When any variable occurs more than one time in any constituent or in any formula herein, its definition on each occurrence is independent of its definition at every other occurrence. Also, combinations of substituents and/or variables are permissible only if such combinations result in stable compounds.

A "stable compound" or "stable structure" refers to a compound that is sufficiently robust to survive isolation to a useful degree of purity and formulation into an efficacious therapeutic agent.

The term "amino acid" refers to the common natural (genetically encoded) or synthetic amino acids and common derivatives thereof, known to those skilled in the art. When applied to amino acids, "standard" or "proteinogenic" refers to the genetically encoded 20 amino acids in their natural configuration. Similarly, when applied to amino acids, "unnatural" or "unusual" refers to the wide selection of non-natural, rare or synthetic amino acids such as those described by Hunt, S. in *Chemistry and Biochemistry of the Amino Acids*, Barrett, G. C., Ed., Chapman and Hall: New York, 1985.

The term "residue" with reference to an amino acid or amino acid derivative refers to a group of the formula:

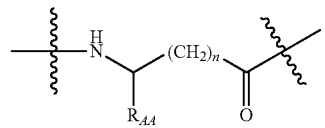

wherein $R_{AA}$ is an amino acid side chain, and n=0, 1 or 2 in this instance.

The term "fragment" with respect to a dipeptide, tripeptide or higher order peptide derivative indicates a group that contains two, three or more, respectively, amino acid residues.

The term "amino acid side chain" refers to any side chain from a standard or unnatural amino acid, and is denoted $R_{AA}$. For example, the side chain of alanine is methyl, the side chain of valine is isopropyl and the side chain of tryptophan is 3-indolylmethyl.

The term "agonist" refers to a compound that duplicates at least some of the effect of the endogenous ligand of a protein, receptor, enzyme or the like.

The term "antagonist" refers to a compound that inhibits at least some of the effect of the endogenous ligand of a protein, receptor, enzyme or the like.

The term "growth hormone secretagogue" (GHS) refers to any exogenously administered compound or agent that directly or indirectly stimulates or increases the endogenous release of growth hormone, growth hormone-releasing hormone, or somatostatin in an animal, in particular, a human. A GHS may be peptidic or non-peptidic in nature, in some instances, with an agent that can be administered orally. In some instances, the agent can induce a pulsatile response.

The term "modulator" refers to a compound that imparts an effect on a biological or chemical process or mechanism. For example, a modulator may increase, facilitate, upregulate, activate, inhibit, decrease, block, prevent, delay, desensitize, deactivate, down regulate, or the like, a biological or chemical process or mechanism. Accordingly, a modulator can be an "agonist" or an "antagonist." Exemplary biological processes or mechanisms affected by a modulator include, but are not limited to, receptor binding and hormone release or secretion. Exemplary chemical processes or mechanisms affected by a modulator include, but are not limited to, catalysis and hydrolysis.

The term "variant" when applied to a receptor is meant to include dimers, trimers, tetramers, pentamers and other biological complexes containing multiple components. These components can be the same or different.

The term "peptide" refers to a chemical compound comprised of two or more amino acids covalently bonded together.

The term "peptidomimetic" refers to a chemical compound designed to mimic a peptide, but which contains structural differences through the addition or replacement of one of more functional groups of the peptide in order to modulate its activity or other properties, such as solubility, metabolic stability, oral bioavailability, lipophilicity, permeability, etc. This can include replacement of the peptide bond, side chain modifications, truncations, additions of functional groups, etc. When the chemical structure is not derived from the peptide, but mimics its activity, it is often referred to as a "non-peptide peptidomimetic."

The term "peptide bond" refers to the amide [—C(=O)—NH—] functionality with which individual amino acids are typically covalently bonded to each other in a peptide.

The term "protecting group" refers to any chemical compound that may be used to prevent a potentially reactive functional group, such as an amine, a hydroxyl or a carboxyl, on a molecule from undergoing a chemical reaction while chemical change occurs elsewhere in the molecule. A number of such protecting groups are known to those skilled in the art and examples can be found in "Protective Groups in Organic Synthesis," Theodora W. Greene and Peter G. Wuts, editors, John Wiley & Sons, New York, 3$^{rd}$ edition, 1999 [ISBN 0471160199]. Examples of amino protecting groups include, but are not limited to, phthalimido, trichloroacetyl, benzyloxycarbonyl, tert-butoxycarbonyl, and adamantyloxycarbonyl. In some embodiments, amino protecting groups are carbamate amino protecting groups, which are defined as an amino protecting group that when bound to an amino group forms a carbamate. In other embodiments, amino carbamate protecting groups are allyloxycarbonyl (Alloc), benzyloxycarbonyl (Cbz), 9-fluorenylmethoxycarbonyl (Fmoc), tert-butoxycarbonyl (Boc) and α,α-dimethyl-3,5-dimethoxybenzyloxycarbonyl (Ddz). For a recent discussion of newer nitrogen protecting groups: Theodoridis, G. Tetrahedron 2000, 56, 2339-2358. Examples of hydroxyl protecting groups include, but are not limited to, acetyl, tert-butyldimethylsilyl (TBDMS), trityl (Trt), tert-butyl, and tetrahydropyranyl (THP). Examples of carboxyl protecting groups include, but are not limited to methyl ester, tert-butyl ester, benzyl ester, trimethylsilylethyl ester, and 2,2,2-trichloroethyl ester.

The term "solid phase chemistry" refers to the conduct of chemical reactions where one component of the reaction is covalently bonded to a polymeric material (solid support as defined below). Reaction methods for performing chemistry on solid phase have become more widely known and established outside the traditional fields of peptide and oligonucleotide chemistry.

The term "solid support," "solid phase" or "resin" refers to a mechanically and chemically stable polymeric matrix utilized to conduct solid phase chemistry. This is denoted by "Resin," "P-" or the following symbol:

Examples of appropriate polymer materials include, but are not limited to, polystyrene, polyethylene, polyethylene glycol, polyethylene glycol grafted or covalently bonded to polystyrene (also termed PEG-polystyrene, TentaGel™, Rapp, W.; Zhang, L.; Bayer, E. In *Innovations and Perspectives in Solid Phase Synthesis. Peptides, Polypeptides and Oligonucleotides*; Epton, R., Ed.; SPCC Ltd.: Birmingham, UK; p 205), polyacrylate (CLEAR™), polyacrylamide, polyurethane, PEGA [polyethyleneglycol poly(N,N-dimethylacrylamide) co-polymer, Meldal, M. *Tetrahedron Lett.* 1992, 33, 3077-3080], cellulose, etc. These materials can optionally contain additional chemical agents to form cross-linked bonds to mechanically stabilize the structure, for example polystyrene cross-linked with divinylbenezene (DVB, usually 0.1-5%, preferably 0.5-2%). This solid support can include as non-limiting examples aminomethyl polystyrene, hydroxymethyl polystyrene, benzhydrylamine polystyrene (BHA), methylbenzhydrylamine (MBHA) polystyrene, and other polymeric backbones containing free chemical functional groups, most typically, —NH$_2$ or —OH, for further derivatization or reaction. The term is also meant to include "Ultraresins" with a high proportion ("loading") of these functional groups such as those prepared from polyethyleneimines and cross-linking molecules (Barth, M.; Rademann, J. *J. Comb. Chem.* 2004, 6, 340-349). At the conclusion of the synthesis, resins are typically discarded, although they have been shown to be able to be reused such as in Frechet, J. M. J.; Haque, K. E. *Tetrahedron Lett.* 1975, 16, 3055.

In general, the materials used as resins are insoluble polymers, but certain polymers have differential solubility depending on solvent and can also be employed for solid phase chemistry. For example, polyethylene glycol can be utilized in this manner since it is soluble in many organic solvents in which chemical reactions can be conducted, but it is insoluble in others, such as diethyl ether. Hence, reactions can be conducted homogeneously in solution, then the product on the polymer precipitated through the addition of diethyl ether and processed as a solid. This has been termed. "liquid-phase" chemistry.

The term "linker" when used in reference to solid phase chemistry refers to a chemical group that is bonded covalently to a solid support and is attached between the support and the substrate typically in order to permit the release (cleavage) of the substrate from the solid support. However, it can also be used to impart stability to the bond to the solid support or merely as a spacer element. Many solid supports are available commercially with linkers already attached.

Abbreviations used for amino acids and designation of peptides follow the rules of the IUPAC-IUB Commission of Biochemical Nomenclature in *J. Biol. Chem.* 1972, 247, 977-983. This document has been updated: *Biochem. J.*, 1984, 219, 345-373; *Eur. J. Biochem.*, 1984, 138, 9-37; 1985, 152, 1; *Internat. J. Pept. Prot. Res.*, 1984, 24, following p 84; *J. Biol. Chem.*, 1985, 260, 14-42; *Pure Appl, Chem.*, 1984, 56, 595-624; *Amino Acids and Peptides*, 1985, 16, 387-410; and in *Biochemical Nomenclature and Related Documents*, 2nd edition, Portland Press, 1992, pp 39-67. Extensions to the rules were published in the JCBN/NC-IUB Newsletter 1985, 1986, 1989; see *Biochemical Nomenclature and Related Documents*, 2nd edition, Portland Press, 1992, pp 68-69.

The term "effective amount" or "effective" is intended to designate a dose that causes a relief of symptoms of a disease or disorder as noted through clinical testing and evaluation, patient observation, and/or the like, and/or a dose that causes a detectable change in biological or chemical activity. The detectable changes may be detected and/or further quantified by one skilled in the art for the relevant mechanism or process. As is generally understood in the art, the dosage will vary depending on the administration routes, symptoms and body weight of the patient but also depending upon the compound being administered.

Administration of two or more compounds "in combination" means that the two compounds are administered closely enough in time that the presence of one alters the biological effects of the other. The two compounds can be administered simultaneously (concurrently) or sequentially. Simultaneous administration can be carried out by mixing the compounds prior to administration, or by administering the compounds at the same point in time but at different anatomic sites or using different routes of administration. The phrases "concurrent administration", "administration in combination", "simultaneous administration" or "administered simultaneously" as used herein, means that the compounds are administered at the same point in time or immediately following one another. In the latter case, the two compounds are administered at times sufficiently close that the results observed are indistinguishable from those achieved when the compounds are administered at the same point in time.

Moreover, the compounds of the present invention can be administered in combination with another compound, such as a particular agent(s), in a manner that contemplates administering the compounds of the present invention prior to initiating therapy with the particular agent(s) in order to prevent and/or treat the effects of the particular agent(s).

The term "pharmaceutically active metabolite" is intended to mean a pharmacologically active product produced through metabolism in the body of a specified compound.

The term "solvate" is intended to mean a pharmaceutically acceptable solvate form of a specified compound that retains the biological effectiveness of such compound. Examples of solvates, without limitation, include compounds of the invention in combination with water, isopropanol, ethanol, methanol, DMSO, ethyl acetate, acetic acid, or ethanolamine.

1. Compounds

Novel macrocyclic compounds of the present invention include macrocyclic compounds comprising a building block structure including a tether component that undergoes cyclization to form the macrocyclic compound. The building block structure can comprise amino acids (standard and unnatural), hydroxy acids, hydrazino acids, aza-amino acids, specialized moieties such as those that play a role in the introduction of peptide surrogates and isosteres, and a tether component as described herein.

The present invention includes isolated compounds. An isolated compound refers to a compound that, in some embodiments, comprises at least 10%, at least 25%, at least 50% or at least 70% of the compounds of a mixture. In some embodiments, the compound, pharmaceutically acceptable salt thereof or pharmaceutical composition containing the compound exhibits a statistically significant binding and/or antagonist activity when tested in biological assays at the human ghrelin receptor.

In the case of compounds, salts, or solvates that are solids, it is understood by those skilled in the art that the inventive compounds, salts, and solvates may exist in different crystal or polymorphic forms, all of which are intended to be within the scope of the present invention and specified formulas.

The compounds disclosed herein may have asymmetric centers. The inventive compounds may exist as single stereoisomers, racemates, and/or mixtures of enantiomers and/or diastereomers. All such single stereoisomers, racemates, and mixtures thereof are intended to be within the scope of the present invention. In particular embodiments, however, the inventive compounds are used in optically pure form. The terms "S" and "R" configuration as used herein are as defined by the IUPAC 1974 Recommendations for Section E, Fundamentals of Stereochemistry (*Pure Appl. Chem.* 1976, 45, 13-30).

Unless otherwise depicted to be a specific orientation, the present invention accounts for all stereoisomeric forms. The compounds may be prepared as a single stereoisomer or a mixture of stereoisomers. The non-racemic forms may be obtained by either synthesis or resolution. The compounds may, for example, be resolved into the component enantiomers by standard techniques, for example formation of diastereomeric pairs via salt formation. The compounds also may be resolved by covalently bonding to a chiral moiety. The diastereomers can then be resolved by chromatographic separation and/or crystallographic separation. In the case of a chiral auxiliary moiety, it can then be removed. As an alternative, the compounds can be resolved through the use of chiral chromatography. Enzymatic methods of resolution could also be used in certain cases.

As generally understood by those skilled in the art, an "optically pure" compound is one that contains only a single enantiomer. As used herein, the term "optically active" is intended to mean a compound comprising at least a sufficient excess of one enantiomer over the other such that the mixture rotates plane polarized light. Optically active compounds have the ability to rotate the plane of polarized light. The excess of one enantiomer over another is typically expressed as enantiomeric excess (e.e.). In describing an optically active compound, the prefixes D and L or R and S are used to denote the absolute configuration of the molecule about its chiral center(s). The prefixes "d" and "l" or (+) and (−) are used to denote the optical rotation of the compound (i.e., the direction in which a plane of polarized light is rotated by the optically active compound). The "l" or (−) prefix indicates that the compound is levorotatory (i.e., rotates the plane of polarized light to the left or counterclockwise) while the "d" or (+) prefix means that the compound is dextrorotatory (i.e., rotates the plane of polarized light to the right or clockwise). The sign of optical rotation, (−) and (+), is not related to the absolute configuration of the molecule, R and S.

A compound of the invention having the desired pharmacological properties will be optically active and, can be comprised of at least 90% (80% e.e.), at least 95% (90% e.e.), at least 97.5% (95% e.e.) or at least 99% (98% e.e.) of a single isomer.

Likewise, many geometric isomers of double bonds and the like can also be present in the compounds disclosed herein, and all such stable isomers are included within the present invention unless otherwise specified. Also included in the invention are tautomers and rotamers of the compounds.

The use of the following symbols at the right refers to substitution of one or more hydrogen atoms of the indicated ring with the defined substituent R.

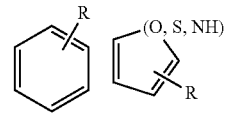

The use of the following symbol indicates a single bond or an optional double bond: ≈, Embodiments of the present invention further provide intermediate compounds formed through the synthetic methods described herein to provide the compounds of formula I and/or II. The intermediate compounds may possess utility as a therapeutic agent for the range of indications described herein and/or a reagent for further synthesis methods and reactions.

2. Synthetic Methods

The compounds of the present invention can be synthesized using traditional solution synthesis techniques or solid phase chemistry methods. In either, the construction involves four phases: first, synthesis of the building blocks comprising recognition elements for the biological target receptor, plus one tether moiety, primarily for control and definition of conformation. These building blocks are assembled together, typically in a sequential fashion, in a second phase employing standard chemical transformations.

The precursors from the assembly are then cyclized in the third stage to provide the macrocyclic structures. Finally, the post-cyclization processing fourth stage involving removal of protecting groups and optional purification provides the desired final compounds. Synthetic methods for this general type of macrocyclic structure are described in Intl, Pat. Appls. WO 01/25257, WO 2004/111077, WO 2005/012331 and WO 2005/012332, including purification procedures described in WO 2004/111077 and WO 2005/012331. See also U.S. patent application Ser. Nos. 11/149,512 and 11/149,731.

In some embodiments of the present invention, the macrocyclic compounds may be synthesized using solid phase chemistry on a soluble or insoluble polymer matrix as previously defined. For solid phase chemistry, a preliminary stage involving the attachment of the first building block, also termed "loading," to the resin must be performed. The resin utilized for the present invention preferentially has attached to it a linker moiety, L. These linkers are attached to an appropriate free chemical functionality, usually an alcohol or amine, although others are also possible, on the base resin through standard reaction methods known in the art, such as any of the large number of reaction conditions developed for the formation of ester or amide bonds. Some linker moieties for the present invention are designed to allow for simultaneous cleavage from the resin with formation of the macrocycle in a process generally termed "cyclization-release." (van Maarseveen, J. H. Solid phase synthesis of heterocycles by cyclization/cleavage methodologies. *Comb. Chem. High Throughput Screen.* 1998, 1, 185-214; Ian W. James, Linkers for solid phase organic synthesis. *Tetrahedron* 1999, 55, 4855-4946; Eggenweiler, H.-M. Linkers for solid-phase synthesis of small molecules: coupling and cleavage techniques. *Drug Discovery Today* 1998, 3, 552-560; Backes, B. J.; Ellman, J. A. Solid support linker strategies. *Curr. Opin. Chem. Biol.* 1997, 1, 86-93. Of particular utility in this regard for compounds of the invention is the 3-thiopropionic acid linker. (Hojo, H.; Aimoto, S. *Bull. Chem. Soc. Jpn.* 1991, 64, 111-117; Zhang, L.; Tam, J. *J. Am. Chem. Soc.* 1999, 121, 3311-3320.)

Such a process provides material of higher purity as only cyclic products are released from the solid support and no contamination with the linear precursor occurs as would happen in solution phase. After sequential assembly of all the building blocks and tether into the linear precursor using known or standard reaction chemistry, base-mediated intramolecular attack on the carbonyl attached to this linker by an appropriate nucleophilic functionality that is part of the tether building block results in formation of the amide or ester bond that completes the cyclic structure as shown (Scheme 1). An analogous methodology adapted to solution phase can also be applied as would likely be preferable for larger scale applications.

Scheme 1. Cyclization-release Strategy

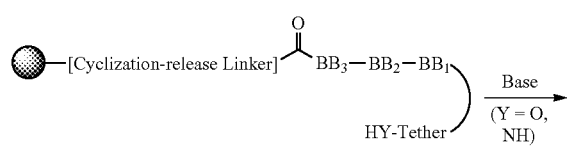

-continued

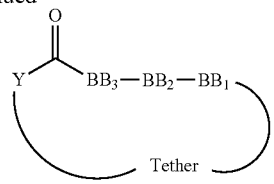

Although this description accurately represents the pathway for one of the methods of the present invention, the thioester strategy, another method of the present invention, that of ring-closing metathesis (RCM), proceeds through a modified route where the tether component is actually assembled during the cyclization step. However, in the RCM methodology as well, assembly of the building blocks proceeds sequentially, followed by cyclization (and release from the resin if solid phase). An additional post-cyclization processing step is required to remove particular byproducts of the RCM reaction, but the remaining subsequent processing is done in the same manner as for the thioester or analogous base-mediated cyclization strategy.

Moreover, it will be understood that steps including the methods provided herein may be performed independently or at least two steps may be combined. Additionally, steps including the methods provided herein, when performed independently or combined, may be performed at the same temperature or at different temperatures without departing from the teachings of the present invention.

Novel macrocyclic compounds of the present invention include those formed by a novel process including cyclization of a building block structure to form a macrocyclic compound comprising a tether component described herein. Accordingly, the present invention provides methods of manufacturing the compounds of the present invention comprising (a) assembling building block structures, (b) chemically transforming the building block structures, (c) cyclizing the building block structures including a tether component, (d) removing protecting groups from the building block structures, and (e) optionally purifying the product obtained from step (d). In some embodiments, assembly of the building block structures may be sequential. In further embodiments, the synthesis methods are carried out using traditional solution synthesis techniques or solid phase chemistry techniques.

A. Amino Acids

Amino acids, Boc- and Fmoc-protected amino acids and side chain protected derivatives, including those of N-methyl and unnatural amino acids, were obtained from commercial suppliers [for example Advanced ChemTech (Louisville, Ky., USA), Astatech (Bristol, Pa., USA), Bachem (Bubendorf, Switzerland), ChemImpex (Wood Dale, Ill., USA), Novabiochem (subsidiary of Merck KGaA, Darmstadt, Germany), PepTech (Burlington, Mass., USA), Synthetech (Albany, Oreg., USA)] or synthesized through standard methodologies known to those in the art. Ddz-amino acids were either obtained commercially from Orpegen (Heidelberg, Germany) or Advanced ChemTech (Louisville, Ky., USA) or synthesized using standard methods utilizing Ddz-OPh or Ddz-$N_3$. (Birr, C.; Lochinger, W.; Stahnke, G.; Lang, P. *Justus Liebigs Ann. Chem.* 1972, 763, 162-172.) Bts-amino acids were synthesized by known methods. (Vedejs, E.; Lin, S.; Klapara, A.; Wang, J. *J. Am. Chem. Soc.* 1996, 118, 9796-9797. Also WO 01/25257, WO 2004/111077) N-Alkyl amino acids, in particular N-methyl amino acids, are commercially available from multiple vendors (Bachem, Novabiochem, Advanced ChemTech, ChemImpex). In addition, N-alkyl amino acid derivatives were accessed via literature methods. (Hansen. D. W., Jr.; Pilipauskas, D. *J. Org. Chem.* 1985, 50, 945-950.)

B. Tethers

Tethers were obtained from the methods previously described in Intl. Pat. Appl. WO 01/25257, WO 2004/111077, WO 2005/012331, and PCT/US2007/017905. See also U.S. patent application Ser. Nos. 11/149,512 and 11/149,731. The preparation of additional tethers is provided in the Examples.

The following are tether intermediates utilized in the synthesis of compounds of the present invention:

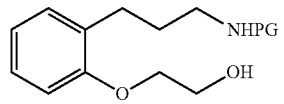

T9

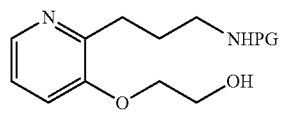

T11

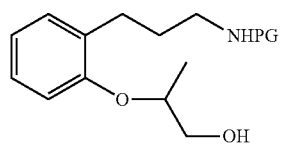

T33a [(R)-isomer]
T33b [(S)-isomer]

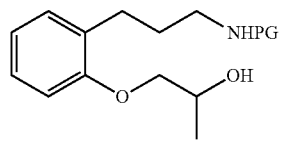

T38a [(R)-isomer]
T38b [(S)-isomer]

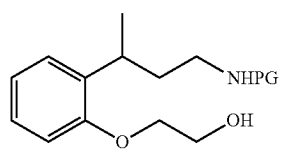

T39a [(R)-isomer]
T39b [(S)-isomer]

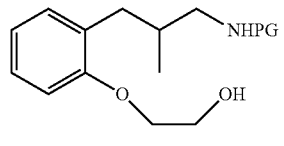

T40a [(R)-isomer]
T40b [(S)-isomer]

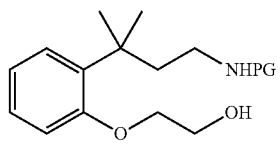

T58

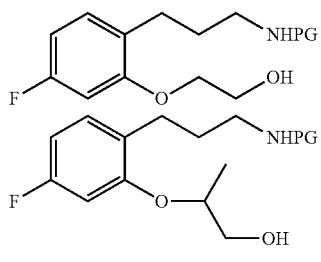

T69

T75a [(R)-isomer]
T75b [(S)-isomer]

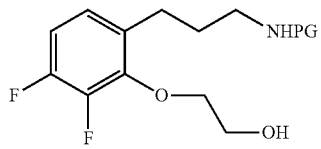

T85

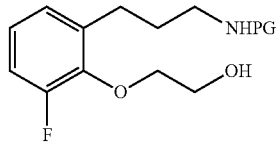

T86

T87

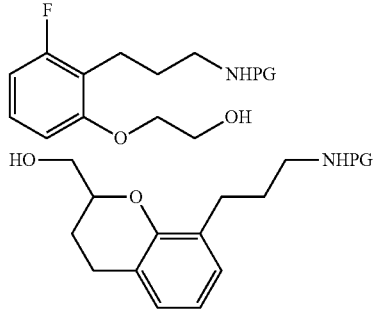

T100a [(R)-isomer]
T100b [(S)-isomer]

T101a [(2R,9R)-isomer]
T101b [(2S,9S)-isomer]
T101c [2R,9S)-isomer]
T101d [2S,9R)-isomer]

T102a [(2R,9R)-isomer]
T102b [(2S,9S)-isomer]

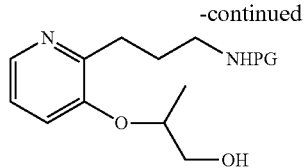
T103a [(R)-isomer]
T103b [(S)-isomer]
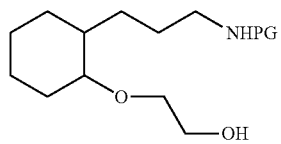
T104
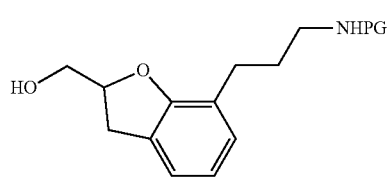
T105a [(R)-isomer]
T105b [(S)-isomer]
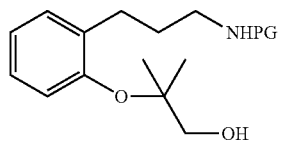
T108
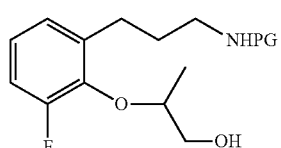
T109a [(R)-isomer]
T109b [(S)-isomer]
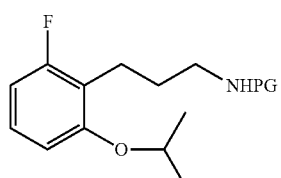
T110a [(R)-isomer]
T110b [(S)-isomer]
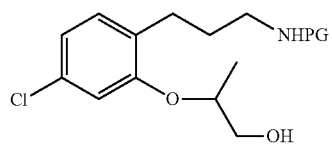
T111a [(R)-isomer]
T111b [(S)-isomer]
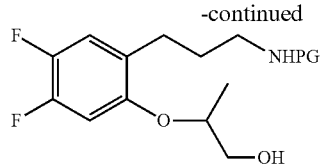
T112a [(R)-isomer]
T112b [(S)-isomer]
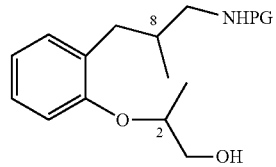
T114a [(2R,8R)-isomer]
T114b [(2S,8S)-isomer]
T114c [(2R,8S)-isomer]
T114d [(2S,8R)-isomer]
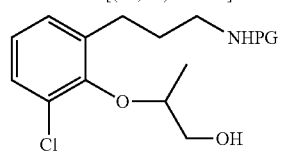
T115a [(R)-isomer]
T115b [(S)-isomer]
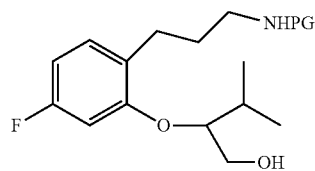
T116a [(R)-isomer]
T116b [(S)-isomer]
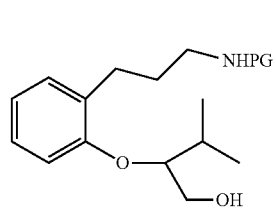
T117a [(R)-isomer]
T117b [(S)-isomer]
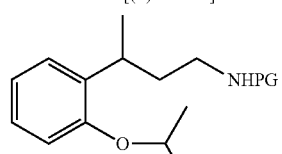
T118a [(2R,7R)-isomer]
T118b [(2S,7S)-isomer]
T118c [(2R,7S)-isomer]
T118d [(2S,7R)-isomer]
T119
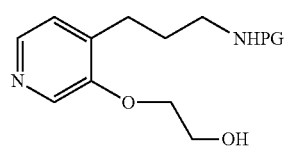

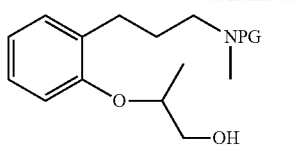

T122a [(R)-isomer]
T122b [(S)-isomer]

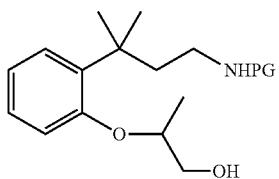

T123a [(R)-isomer]
T123b [(S)-isomer]

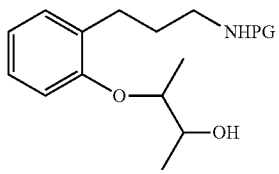

T124a [(1R,2R)-isomer]
T124b [(1S,2S)-isomer]
T124c [(1R,2S)-isomer]
T124d [(1S,2R)-isomer]

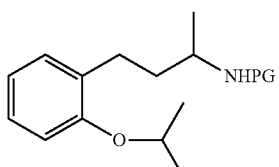

T125a [(R)-isomer]
T125b [(S)-isomer]

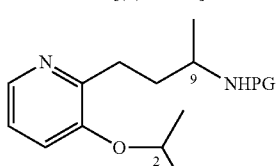

T126a [(2R,9R)-isomer]
T126b [(2S,9S)-isomer]
T126c [(2R,9S)-isomer]
T126d [(2S,9R)-isomer]

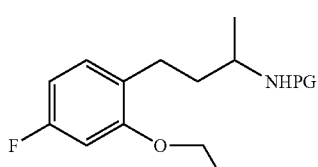

T129a [(R)-isomer]
T129b [(S)-isomer]

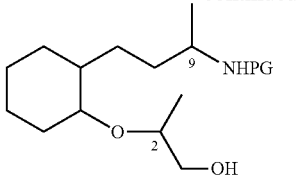

T130a [(2R,9R)-isomer]
T130b [(2S,9S)-isomer]
T130c [(2R,9S)-isomer]
T130d [(2S,9R)-isomer]

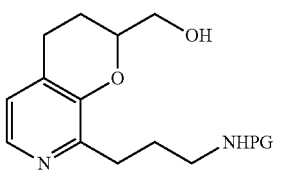

T131a [(R)-isomer]
T131b [(S)-isomer]

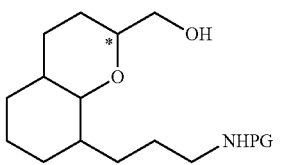

T132a [(R*)-isomer]
T132b [(S*)-isomer]

T133

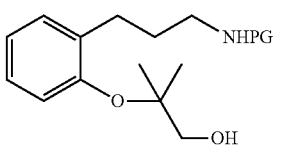
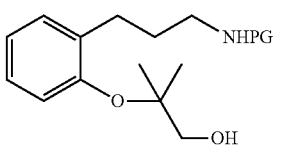

C. Solid and Solution Phase Techniques

Specific solid phase techniques for the synthesis of the macrocyclic compounds of the invention have been described in WO 01/25257, WO 2004/111077, WO 2005/012331 and WO 2005/012332. Solution phase synthesis routes, including methods amenable to larger scale manufacture, were described in U.S. Patent Appl. Publ. Nos. 2006/025566 and US 2007/0021331.

In certain cases, however, the lability of protecting groups precluded the use of the standard basic medium for cyclization in the thioester strategy discussed above. In these cases, either of two acidic methods was employed to provide macrocyclization under acid conditions, One method utilized HOAc, while the other method employed HOAt (Scheme 2).

After executing the deprotection of the Ddz or Boc group on the tether, the resin was washed sequentially with DCM (2×), DCM-MeOH (1:1, 2×), DCM (2×), and DIPEA-DCM (3:7, 1×). The resin was dried under vacuum for 10 min, then added immediately to a solution of 1HOAc in degassed DMF (5% v/v). The reaction mixture was agitated at 50-70° C. O/N. The resin was filtered, washed with THF, and the combined filtrate and washes evaporated under reduced pressure (water aspirator, then oil pump) to afford the macrocycle.

Scheme 2: Alternative Cyclization Methodologies

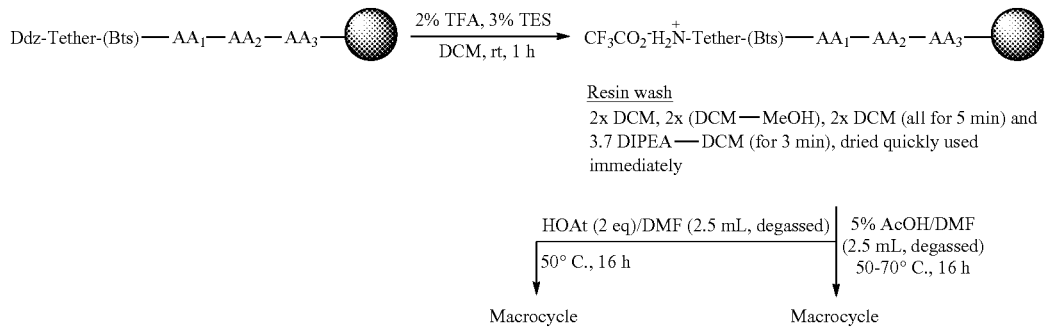

The table following provides information on the building blocks used for the synthesis of representative compounds of the present invention using the standard methods. These are directly applicable to solid phase synthesis. For solution phase syntheses, modified protection strategies from that illustrated are typically employed to permit the use of a convergent approach. Additional synthetic details for the solution phase construction of representative macrocyclic compounds of the invention are presented in the Examples.

Synthesis of Representative Compounds of the Invention

| Compound | $AA_1$ | $AA_2$ | $AA_3$ | Tether |
|---|---|---|---|---|
| 801 | Bts-Chg | Boc-(D)NMeAla | Boc-(D)Leu | Boc-T100a |
| 802 | Bts-Cpg | Boc-(D)NMeAla | Boc-(D)Leu | Boc-T100a |
| 803 | Bts-Cpg | Ddz-(D)NMeAla | Ddz-(D)Tyr(But) | Ddz-T100a |
| 807 | Bts-Cpg | Boc-(D)NMeAla | Boc-(D)Leu | Boc-T101c |
| 808 | Bts-Cpg | Ddz-(D)NMeAla | Ddz-(D)Tyr(But) | Ddz-T101c |
| 809 | Bts-Cpg | Ddz-(D)NMeAla | Ddz-(D)Tyr(But) | Ddz-T69 |
| 810 | Bts-Cpg | Boc-(D)NMeAla | Boc-(D)Leu | Boc-T69 |
| 813 | Bts-Cpg | Boc-(D)NMeAla | Boc-(D)Leu | Boc-T86 |
| 816 | Bts-Cpg | Boc-(D)NMeAla | Boc-(D)Leu | Boc-T85 |
| 818 | Bts-Cpg | Ddz-(D)NMeAla | Ddz-(D)Tyr(But) | Ddz-T85 |
| 819 | Bts-Cpg | Boc-(D)NMeAla | Boc-(D)Leu | Boc-T124a |
| 820 | Bts-Cpg | Ddz-(D)NMeAla | Ddz-(D)Tyr(But) | Ddz-T124a |
| 822 | Bts-Cpg | Boc-(D)NMeAla | Boc-(D)Leu | Boc-T129b |
| 825 | Bts-Cpg | Boc-(D)NMeAla | Boc-(D)Leu | Boc-T102 |
| 826 | Bts-Cpg | Boc-(D)NMeAla | Boc-(D)Tyr | Boc-T102 |
| 828 | Bts-Chg | Boc-(D)NMeAla | Boc-(D)Leu | Boc-T102a |
| 829 | Bts-Chg | Ddz-(D)NMeAla | Ddz-(D)Tyr(But) | Ddz-T102a |
| 831 | Bts-Cpg | Boc-(D)NMeAla | Boc-(D)Cha | Boc-T102 |
| 832 | Bts-Cpg | Boc-(D)NMeAla | Boc-(D)Tyr(3F) | Boc-T102 |
| 833 | Bts-Cpg | Boc-(D)NMeAla | Boc-(D)tBuAla | Boc-T102 |
| 851 | Bts-Cpg | Boc-(D)NMeAla | Boc-(D)Phe | Boc-T33a |
| 853 | Bts-Nva | Boc-(D)NMeAla | Boc-(D)Phe(4-F) | Boc-T33a |
| 854 | Bts-Cpg | Boc-(D)NMeAla | Boc-(D)Phe(4-F) | Boc-T75a |
| 855 | Bts-Ile | Boc-(D)NMeAla | Boc-(D)Phe(4-F) | Boc-T33a |
| 856 | Bts-Ile | Boc-(D)NMeAla | Boc-(D)Phe(4-F) | Boc-T75a |
| 857 | Bts-Val | Boc-(D)NMeAla | Boc-(D)Phe(4-F) | Boc-T33a |
| 858 | Bts-Nva | Boc-(D)NMeAla | Boc-(D)Phe | Boc-T33a |
| 859 | Bts-Nva | Boc-(D)NMeAla | Boc-(D)Phe | Boc-T33b |
| 860 | Bts-Cpg | Boc-(D)NMeAla | Boc-(D)Phe(4-Me) | Boc-T9 |
| 862 | Bts-Cpg | Boc-(D)NMeAla | Boc-(D)Phe(4-Cl) | Boc-T33a |
| 863 | Bts-Nva | Boc-(D)NMeAla | Boc-(D)Phe(4-Cl) | Boc-T33a |
| 864 | Bts-Cpg | Boc-(D)NMeAla | Boc-(D)Phe(4-Cl) | Boc-T69 |
| 865 | Bts-Cpg | Boc-(D)NMeAla | Boc-(D)Phe | Boc-T69 |
| 866 | Bts-Nva | Boc-(D)NMeAla | Boc-(D)Tyr(OMe) | Boc-T33a |
| 867 | Bts-Cpg | Boc-(D)NMeAla | Boc-(D)Tyr(OMe) | Boc-T33a |
| 869 | Bts-Val | Boc-(D)NMeAla | Boc-(D)Phe(4-F) | Boc-T9 |
| 870 | Bts-Val | Boc-(D)NMeAla | Boc-(D)Phe | Boc-T33b |
| 871 | Bts-Val | Boc-(D)NMeAla | Boc-(D)Phe | Boc-T33a |
| 872 | Bts-Cpg | Boc-(D)NMeAla | Boc-(D)Phe(2-Cl) | Boc-T9 |
| 873 | Bts-Cpg | Boc-(D)NMeAla | Boc-(D)Phe(3-Cl) | Boc-T9 |
| 874 | Bts-Cpg | Boc-(D)NMeAla | Boc-(D)Phe | Boc-T100 |
| 876 | Bts-Cpg | Boc-(D)NMeAla | Boc-(D)Phe | Boc-T75a |
| 877 | Bts-Cpg | Boc-(D)NMeAla | Boc-(D)Phe(4-Cl) | Boc-T75a |
| 878 | Bts-Ile | Boc-(D)NMeAla | Boc-(D)Phe(4-Cl) | Boc-T33a |
| 923 | Bts-Ile | Boc-(D)NMeAla | Boc-(D)Phe | T133 via RCM |
| 934 | Bts-Ile | Ddz-(D)NMeSer(But) | Boc-(D)Phe | Boc-T9 |
| 935 | Bts-Cpg | Boc-(D)NMeAla | Boc-(D)Phe(4-F) | Boc-T109a |
| 936 | Bts-Cpg | Boc-(D)NMeAla | Boc-(D)Phe(4-Cl) | Boc-T109a |
| 937 | Bts-Cpg | Boc-(D)NMeAla | Boc-(D)Phe(4-F) | Boc-T110a |
| 938 | Bts-Cpg | Boc-(D)NMeAla | Boc-(D)Phe(4-Cl) | Boc-T110a |

-continued

| Compound | AA₁ | AA₂ | AA₃ | Tether |
|---|---|---|---|---|
| 939 | Bts-Ile | Ddz-(D)NMeSer(But) | Boc-(D)Phe | Boc-T33a |
| 944 | Bts-Cpg | Boc-(D)NMeAla | Boc-(D)Phe(4-F) | Boc-T110a |
| 945 | Bts-Cpg | Boc-(D)NMeAla | Boc-(D)Phe(4-Cl) | Boc-T110a |
| 946 | Bts-Cpg | Boc-(D)NMeAla | Boc-(D)Phe(4-F) | Boc-T100 |
| 947 | Bts-Cpg | Boc-(D)NMeAla | Boc-(D)Phe(4-Cl) | Boc-T100 |
| 950 | Bts-Cpg | Boc-(D)NMeAla | Boc-(D)Phe(4-F) | Boc-T112a |
| 951 | Bts-Cpg | Boc-(D)NMeAla | Boc-(D)Phe(4-Cl) | Boc-T112a |
| 954 | Bts-Ile | Boc-(D)NMe(β-F)Ala | Boc-(D)Phe | Boc-T9 |
| 965 | Bts-Cpg | Boc-(D)NMeAla | Boc-(D)Phe | Boc-T116a |
| 966 | Bts-Cpg | Boc-(D)NMeAla | Boc-(D)Phe(4-Cl) | Boc-T116a |
| 968 | Bts-Cpg | Boc-(D)NMeAla | Boc-(D)Leu | Boc-T33a |
| 969 | Bts-Ile | Boc-(D)NMeAla | Boc-(D)Leu | Boc-T33a |
| 972 | Bts-Cpg | Boc-(D)NMeAla | Boc-(D)2Pal | Boc-T33a |
| 973 | Bts-Cpg | Boc-(D)NMeAla | Boc-(D)3Pal | Boc-T109a |
| 974 | Bts-Ile | Boc-(D)NMeAla | Boc-(D)3Pal | Boc-T109a |
| 975 | Bts-Cpg | Boc-(D)NMeAla | Boc-(D)3Pal | Boc-T33a |
| 976 | Bts-Ile | Boc-(D)NMeAla | Boc-(D)3Pal | Boc-T33a |
| 977 | Bts-Cpg | Boc-(D)NMeAla | Boc-(D)4Pal | Boc-T33a |
| 978 | Bts-Ile | Boc-(D)NMeAla | Boc-(D)4Pal | Boc-T33a |
| 979 | Bts-Cpg | Boc-(D)NMeAla | Boc-(D)Leu | Boc-T109a |
| 981 | Bts-Ile | Boc-(D)NMeAla | Boc-(D)Leu | Boc-T109a |
| 982 | Bts-Chg | Boc-(D)NMeAla | Boc-(D)Phe(4-F) | Boc-T33a |
| 986 | Bts-Cpg | Boc-(D)NMeAla | Boc-(D)Leu | Boc-T11 |
| 987 | Bts-Ile | Boc-(D)NMeAla | Boc-(D)Leu | Boc-T11 |
| 988 | Bts-Cpg | Ddz-(D)NMeAla | Ddz-(D)Tyr(But) | Ddz-T11 |
| 989 | Bts-Cpg | Ddz-(D)NMeAla | Ddz-(D)Tyr(But) | Ddz-T33a |
| 991 | Bts-Cpg | Ddz-(D)NMeAla | Ddz-(D)Tyr(But) | Ddz-T109a |
| 992 | Bts-Ile | Ddz-(D)NMeAla | Ddz-(D)Tyr(But) | Ddz-T11 |
| 993 | Bts-Ile | Ddz-(D)NMeAla | Ddz-(D)Tyr(But) | Ddz-T33a |
| 994 | Bts-Ile | Ddz-(D)NMeAla | Ddz-(D)Tyr(But) | Ddz-T109a |
| 995 | Bts-Cpg | Boc-(D)NMeAla | Boc-(D)2-Thi | Boc-T11 |
| 996 | Bts-Ile | Boc-(D)NMeAla | Boc-(D)2-Thi | Boc-T11 |
| 997 | Bts-Thr(OMe) | Boc-(D)NMeAla | Boc-(D)Phe(4-F) | Boc-T11 |
| 998 | Bts-Thr(OMe) | Boc-(D)NMeAla | Boc-(D)Phe(4-F) | Boc-T33a |
| 999 | Bts-Cpg | Boc-(D)NMeAla | Boc-(D)Leu | Boc-T103a |
| 1000 | Bts-Ile | Boc-(D)NMeAla | Boc-(D)Leu | Boc-T103a |
| 1003 | Bts-Cpg | Boc-(D)NMeAla | Boc-(D)Phe(4-F) | Boc-T108 |
| 1005 | Bts-Cpg | Boc-(D)NMeAla | Boc-(D)Phe(4-F) | Boc-T114a |
| 1006 | Bts-Cpg | Boc-(D)NMeAla | Boc-(D)Leu | Boc-T115a |
| 1007 | Bts-Cpg | Boc-(D)NMeAla | Boc-(D)Phe(4-F) | Boc-T115a |
| 1008 | Bts-Cpg | Boc-(D)NMeAla | Boc-(D)Cpa | Boc-T33a |
| 1009 | Bts-Cpg | Boc-(D)NMeAla | Boc-(D)Phe(4-F) | Boc-T100a |
| 1010 | Bts-Cpg | Boc-(D)NMeAla | Boc-(D)Phe(4-F) | Boc-T101a |
| 1011 | Bts-Cpg | Boc-(D)NMeAla | Boc-(D)Phe(4-F) | Boc-T101c |
| 1014 | Bts-Cpg | Boc-(D)NMeAla | Boc-(D)Tle | Boc-T33a |
| 1015 | Bts-Cpg | Boc-(D)NMeAla | Boc-(D)Leu | Boc-T100b |
| 1016 | Bts-Cpg | Boc-(D)NMeAla | Boc-(D)Phe(4-F) | Boc-T100b |
| 1017 | Bts-Cpg | Boc-(D)NMeAla | Boc-(D)Phe(4-F) | Boc-T118a/c |
| 1018 | Bts-Cpg | Boc-(D)NMeAla | Boc-(D)(β-RMe)Phe(4-F) | Boc-T33a |
| 1019 | Bts-Cpg | Boc-(D)NMeAla | Boc-(D)Leu | Boc-T105 |
| 1020 | Bts-Cpg | Boc-(D)NMeAla | Boc-(D)Phe(4-F) | Boc-T105 |
| 1021 | Bts-Cpg | Boc-(D)NMeAla | Boc-(D)Leu | Boc-T119 |
| 1022 | Bts-Ile | Boc-(D)NMeAla | Boc-(D)Leu | Boc-T119 |
| 1023 | Bts-Cpg | Ddz-(D)NMeAla | Ddz-(D)Tyr(But) | Ddz-T103a |
| 1024 | Bts-Cpg | Ddz-(D)NMeAla | Ddz-(D)Tyr(But) | Ddz-T100b |
| 1025 | Bts-Cpg | Ddz-(D)NMeAla | Ddz-(D)Tyr(But) | Ddz-T105 |
| 1026 | Bts-Ile | Ddz-(D)NMeAla | Ddz-(D)Tyr(But) | Ddz-T103a |
| 1027 | Bts-Cpg | Boc-(D)NMeAla | Boc-(D)Phe(4-F) | Boc-T103a |
| 1028 | Bts-Cpg | Boc-(D)NMeAla | Boc-(D)Phe | Boc-T103a |
| 1029 | Bts-Ile | Boc-(D)NMeAla | Boc-(D)Phe(4-F) | Boc-T103a |
| 1030 | Bts-Ile | Boc-(D)NMeAla | Boc-(D)Phe | Boc-T103a |
| 1031 | Bts-Cpg | Boc-(D)NMeAla | Boc-(D)Phe | Boc-T119 |
| 1032 | Bts-Thr(OMe) | Boc-(D)NMeAla | Boc-(D)Phe(4-F) | Boc-T103a |
| 1033 | Bts-Cpg | Boc-(D)NMeAla | Boc-(D)Phe(4-F) | Boc-T114c |
| 1034 | Bts-Cpg | Boc-(D)NMeAla | Boc-(β-SMe)(D)Phe(4F) | Boc-T33a |
| 1035 | Bts-Cpg | Boc-(D)NMeAla | Boc-(β-diMe)(D)Phe(4F) | Boc-T33a |
| 1036 | Bts-Cpg | Boc-(D)NMeAla | Boc-(D)Asp | Boc-T33a |
| 1038 | Bts-Cpg | Boc-(D)NMeAla | Boc-(D)Phe(4-CF₃) | Boc-T33a |
| 1039 | Bts-Cpg | Boc-(D)NMeAla | Boc-(D)Phe(2,4diCl) | Boc-T33a |
| 1040 | Bts-Cpg | Boc-(D)NMeAla | Boc-(D)Phe(3,4diF) | Boc-T33a |
| 1041 | Bts-Cpg | Boc-(D)NMeAla | Boc-(D)Phe(3,4,5-triF) | Boc-T33a |
| 1042 | Bts-Cpg | Boc-(D)NMeAla | Boc-(D)Phe(pentaF) | Boc-T33a |
| 1043 | Bts-Cpg | Boc-(D)NMeAla | Boc-(D)(tBuAla) | Boc-T33a |
| 1044 | Bts-Cpg | Boc-(D)NMeAla | Boc-(D)Tle | Boc-T109a |
| 1045 | Bts-Cpg | Boc-(D)NMeAla | Boc-(D)Cha | Boc-T33a |
| 1046 | Bts-Cpg | Boc-(D)NMeAla | Boc-(D)Chg | Boc-T33a |
| 1047 | Bts-Cpg | Boc-(D)NMeAla | Boc-(DL)(cyclopentyl)Ala | Boc-T33a |

-continued

| Compound | AA₁ | AA₂ | AA₃ | Tether |
|---|---|---|---|---|
| 1048 | Bts-Cpg | Boc-(D)NMeAla | Boc-(D)Cpg | Boc-T33a |
| 1049 | Bts-Cpg | Boc-(D)NMeAla | Boc-(DL)Tyr(3-F) | Boc-T33a |
| 1050 | Bts-Cpg | Ddz-(D)NMeAla | Ddz-(D)Thr(But) | Ddz-T33a |
| 1052 | Bts-Cpg | Boc-(D)NMeAla | Boc-(D)Phe(4-F) | Boc-T102 |
| 1053 | Bts-Cpg | Boc-(D)NMeAla | Boc-(D)Tyr(3,5diBr) | Boc-T33a |
| 1058 | Bts-Cpg | Boc-(D)NMeAla | Boc-(2R,3R)(b-OH)Leu | Boc-T33a |
| 1061 | Bts-Chg | Boc-(D)NMeAla | Boc-(D)Leu | Boc-T103a |
| 1062 | Bts-Chg | Boc-(D)NMeAla | Boc-(D)Tyr | Boc-T103a |
| 1065 | Bts-Cpg | Boc-(D)NMeAla | Boc-(DL)Tyr(3-F,OAc) | Boc-T33a |
| 1066 | Bts-Cpg | Boc-(D)NMeAla | Boc-(D)Tyr(3,5diBr,OAc) | Boc-T33a |
| 1068 | Bts-Cpg | Boc-(D)NMeAla | Boc-(β-SMe)(D)Tyr | Boc-T33a |
| 1069 | Bts-Cpg | Ddz-(D)NMeAla | Ddz-(D)Tyr(But) | Ddz-T122a |
| 1071 | Bts-Cpg | Boc-(D)NMeAla | Boc-(D)Phe(4F) | Boc-T123a |
| 1072 | Bts-Cpg | Ddz-(D)NMeAla | Ddz-(D)Tyr(But) | Ddz-T124d |
| 1074 | Bts-Cpg | Ddz-(D)NMeAla | Ddz-(D)Tyr(But) | Ddz-T131a |
| 1075 | Bts-Cpg | Ddz-(D)NMeAla | Ddz-(D)Tyr(But) | Ddz-T131a |
| 1076 | Bts-Cpg | Boc-(D)NMeAla | Boc-(β-SMe)(D)Tyr | Boc-T131a |
| 1078 | Bts-Cpg | Boc-(D)NMeAla | Boc-(DL)Tyr(3F) | Boc-T11 |
| 1079 | Bts-Cpg | Boc-(D)NMeAla | Boc-(D)mTyr | Boc-T103a |
| 1080 | Bts-Cpg | Boc-(D)NMeAla | Boc-(β-SMe)(D)Tyr | Boc-T11 |
| 1081 | Bts-Cpg | Boc-(D)NMeAla | Boc-(β-RMe)(D)Tyr | Boc-T103a |
| 1082 | Bts-Cpg | Boc-(D)NMeAla | Boc-(β-SMe)(D)Tyr | Boc-T103a |
| 1083 | Bts-Cpg | Ddz-(D)NMeAla | Ddz-(D)Tyr(But) | Ddz-T125b |
| 1084 | Bts-Cpg | Boc-(D)NMeAla | Boc-(D)Leu | Boc-T125b |
| 1085 | Bts-Cpg | Ddz-(D)NMeAla | Ddz-(D)Tyr(But) | Ddz-T125a |
| 1086 | Bts-Cpg | Boc-(D)NMeAla | Boc-(D)Leu | Boc-T125a |
| 1087 | Bts-Cpg | Ddz-(D)NMeAla | Ddz-(D)Tyr(But) | Ddz-T126c |
| 1088 | Bts-Cpg | Boc-(D)NMeAla | Boc-(D)Leu | Boc-T126c |
| 1089 | Bts-Cpg | Ddz-(D)NMeAla | Ddz-(D)Tyr(But) | Ddz-T126a |
| 1090 | Bts-Cpg | Boc-(D)NMeAla | Boc-(D)Asp(OMe) | Boc-T33a |
| 1098 | Bts-Cpg | Boc-(D)NMeAla | Boc-(β-SMe)(D)Tyr | Boc-T126c |
| 1099 | Bts-Chg | Boc-(D)NMeAla | Boc-(D)Leu | Boc-T33a |
| 1100 | Bts-Cpg | Boc-(D)NMeAla | Boc-(D)Phe(4F) | Boc-T85 |
| 1101 | Bts-Cpg | Boc-(D)NMeAla | Boc-(DL)oTyr | Boc-T33a |
| 1103 | Bts-Cpg | Boc-(D)NMeAla | Boc-(D)Phg(4OH) | Boc-T33a |
| 1104 | Bts-Cpg | Boc-(D)NMeAla | Boc-(D)Tyr(3F) | Boc-T33a |
| 1105 | Bts-Chg | Ddz-(D)NMeAla | Ddz-(D)Tyr(But) | Ddz-T100a |
| 1106 | Bts-Cpg | Boc-(D)NMeAla | Boc-(D)Leu | Boc-T104 |
| 1107 | Bts-Cpg | Boc-(D)NMeAla | Boc-(D)Leu | Boc-T130c |
| 1108 | Bts-Chg | Ddz-(D)NMeAla | Ddz-(D)Tyr(But) | Ddz-T33a |
| 1109 | Bts-Cpg | Boc-(D)NMeAla | Boc-(D)Phe(4F) | Boc-T87 |
| 1110 | Bts-Cpg | Ddz-(D)NMeAla | Ddz-(D)Tyr(But) | Ddz-T87 |
| 1111 | Bts-Cpg | Boc-(D)NMeAla | Boc-(D)Leu | Boc-T87 |
| 1112 | Bts-Chg | Boc-(D)NMeAla | Boc-(D)Leu | Boc-T69 |
| 1113 | Bts-Chg | Ddz-(D)NMeAla | Ddz-(D)Tyr(But) | Ddz-T69 |
| 1114 | Bts-Cpg | Boc-(D)NMeAla | Boc-(DL)CyclopentylAla | Boc-T102 |
| 1115 | Bts-Cpg | Boc-(D)NMeAla | Boc-(DL)oTyr | Boc-T102 |
| 1116 | Bts-Cpg | Boc-(D)NMeAla | Boc-(D)Leu | Boc-T132a |
| 1118 | Bts-Cpg | Ddz-(D)NMeAla | Ddz-(D)Tyr(But) | Ddz-T104 |
| 1119 | Bts-Cpg | Boc-(D)NMeAla | Boc-(β-SMe)(D)Tyr | Boc-T101c |

The table below presents analytical data for representative compounds of the present invention.

Analytical Data for Representative Compounds of the Invention

| Compound No. | Molecular Formula | MW Calc (g/mol) | MS [(M + H)+] Found |
|---|---|---|---|
| 801 | C31H48N4O4 | 540.7 | 541 |
| 802 | C28H42N4O4 | 498.7 | 499 |
| 803 | C31H40N4O5 | 548.7 | 549 |
| 807 | C28H44N4O4 | 500.7 | 501 |
| 808 | C31H42N4O5 | 550.7 | 551 |
| 809 | C29H37N4O5F | 540.6 | 541 |
| 810 | C26H39N4O4F | 490.6 | 491 |
| 813 | C26H39N4O4F | 490.6 | 491 |
| 816 | C26H38N4O4F2 | 508.6 | 509 |
| 818 | C29H36N4O5F2 | 558.6 | 559 |
| 819 | C28H44N4O4 | 500.7 | 501 |
| 820 | C31H42N4O5 | 550.7 | 551 |
| 822 | C27H41N4O4F | 504.6 | 505 |
| 825 | C27H41N4O4 | 492.7 | 493 |
| 826 | C30H46N4O5 | 542.7 | 543 |
| 828 | C30H54N4O4 | 534.8 | 535 |
| 829 | C33H52N4O5 | 584.8 | 585 |
| 831 | C30H52N4O4 | 532.8 | 533 |
| 832 | C30H45N4O5F | 560.7 | 561 |
| 833 | C28H50N4O4 | 506.7 | 507 |
| 851 | C30H40N4O4 | 520.7 | 521 |
| 853 | C30H41N4O4F | 540.7 | 541 |
| 854 | C30H38N4O4F2 | 556.6 | 557 |
| 855 | C31H43N4O4F | 554.7 | 555 |
| 856 | C31H42N4O4F2 | 572.7 | 573 |
| 857 | C30H41N4O4F | 540.7 | 541 |
| 858 | C30H42N4O4 | 522.7 | 523 |
| 859 | C30H42N4O4 | 522.7 | 523 |
| 860 | C30H40N4O4 | 520.7 | 521 |
| 862 | C30H39N4O4Cl | 555.1 | 555 |
| 863 | C30H41N4O4Cl | 557.1 | 557 |
| 864 | C29H36N4O4FCl | 559.1 | 559 |
| 865 | C29H37N4O4F | 524.6 | 525 |

-continued

| Compound No. | Molecular Formula | MW Calc (g/mol) | MS [(M + H)+] Found |
|---|---|---|---|
| 866 | C31H44N4O5 | 552.7 | 553 |
| 867 | C31H42N4O5 | 550.7 | 551 |
| 869 | C29H39N4O4Cl | 543.1 | 543 |
| 870 | C30H42N4O4 | 522.7 | 523 |
| 871 | C30H42N4O4 | 522.7 | 523 |
| 872 | C29H37N4O4Cl | 541.1 | 541 |
| 873 | C29H37N4O4Cl | 541.1 | 541 |
| 874 | C31H40N4O4 | 532.7 | 533 |
| 876 | C30H39N4O4F | 538.7 | 539 |
| 877 | C30H38N4O4FCl | 573.1 | 573 |
| 878 | C31H43N4O4Cl | 571.2 | 571 |
| 923 | C32H46N4O4 | 550.7 | 551 |
| 934 | C30H42N4O5 | 538.7 | 539 |
| 935 | C30H38N4O4F2 | 556.6 | 557 |
| 936 | C30H38N4O4FCl | 573.1 | 573 |
| 937 | C30H38N4O4F2 | 556.6 | 557 |
| 938 | C30H38N4O4FCl | 573.1 | 573 |
| 939 | C31H44N4O5 | 552.7 | 553 |
| 944 | C30H38N4O4FCl | 573.1 | 573 |
| 945 | C30H38N4O4Cl2 | 589.6 | 589 |
| 946 | C31H39N4O4F | 550.7 | 551 |
| 947 | C31H39N4O4Cl | 567.1 | 567 |
| 950 | C30H37N4O4F3 | 574.6 | 575 |
| 951 | C30H37N4O4F2Cl | 591.1 | 591 |
| 954 | C30H41N4O4F | 540.7 | 541 |
| 965 | C32H43N4O4F | 566.7 | 567 |
| 966 | C32H42N4O4FCl | 601.2 | 601 |
| 968 | C27H42N4O4 | 486.6 | 487 |
| 969 | C28H46N4O4 | 502.7 | 503 |
| 972 | C29H39N5O4 | 521.7 | 522 |
| 973 | C29H38N5O4F | 539.6 | 540 |
| 974 | C30H42N5O4F | 555.7 | 556 |
| 975 | C29H39N5O4 | 521.7 | 522 |
| 976 | C30H43N5O4 | 537.7 | 538 |
| 977 | C29H39N5O4 | 521.7 | 522 |
| 978 | C30H43N5O4 | 537.7 | 538 |
| 979 | C27H41N4O4F | 504.6 | 505 |
| 981 | C28H45N4O4F | 520.7 | 521 |
| 982 | C33H45N4O4F | 580.7 | 581 |
| 986 | C25H39N5O4 | 473.6 | 474 |
| 987 | C26H43N5O4 | 489.7 | 490 |
| 988 | C28H37N5O5 | 523.6 | 524 |
| 989 | C30H40N5O5 | 536.7 | 537 |
| 991 | C30H39N5O5F | 554.7 | 555 |
| 992 | C29H41N5O5 | 539.7 | 540 |
| 993 | C31H44N4O5 | 552.7 | 553 |
| 994 | C31H43N4O5F | 570.7 | 571 |
| 995 | C26H35N5O4S | 513.7 | 514 |
| 996 | C27H39N5O4S | 529.7 | 530 |
| 997 | C30H41N4O5F | 556.7 | 557 |
| 998 | C28H38N5O5F | 543.6 | 544 |
| 999 | C26H41N5O4 | 487.6 | 488 |
| 1000 | C27H45N5O4 | 503.7 | 504 |
| 1003 | C31H41N4O4F | 552.7 | 553 |
| 1005 | C31H41N4O4F | 552.7 | 553 |
| 1006 | C27H41N4O4Cl | 521.1 | 521 |
| 1007 | C30H38N4O4FCl | 573.1 | 573 |
| 1008 | C27H39N4O4F | 502.6 | 503 |
| 1009 | C31H39N4O4F | 550.7 | 551 |
| 1010 | C31H41N4O4F | 552.7 | 553 |
| 1011 | C31H41N4O4F | 552.7 | 553 |
| 1014 | C27H42N4O4 | 486.6 | 487 |
| 1015 | C28H42N4O4 | 498.7 | 499 |
| 1016 | C31H39N4O4F | 550.7 | 551 |
| 1017 | C31H41N4O4F | 552.7 | 553 |
| 1018 | C31H41N4O4F | 552.7 | 553 |
| 1019 | C27H40N4O4 | 484.6 | 485 |
| 1020 | C30H37N4O4F | 536.6 | 537 |
| 1021 | C25H39N5O4 | 473.6 | 474 |
| 1022 | C26H43N5O4 | 489.7 | 490 |
| 1023 | C29H39N5O5 | 537.7 | 538 |
| 1024 | C31H40N4O5 | 548.7 | 549 |
| 1025 | C30H38N4O5 | 534.6 | 535 |
| 1026 | C30H43N5O5 | 553.7 | 554 |
| 1027 | C29H38N5O4F | 539.6 | 540 |
| 1028 | C29H39N5O4 | 521.7 | 522 |
| 1029 | C30H42N5O4F | 555.7 | 556 |
| 1030 | C30H43N5O4 | 537.7 | 538 |
| 1031 | C28H37N5O4 | 507.6 | 508 |
| 1032 | C29H40N5O5F | 557.7 | 558 |
| 1033 | C31H41N4O4F | 552.7 | 553 |
| 1034 | C31H41N4O4F | 552.7 | 553 |
| 1035 | C32H43N4O4F | 566.7 | 567 |
| 1036 | C25H36N4O6 | 488.6 | 489 |
| 1038 | C31H39N4O4F3 | 588.7 | 589 |
| 1039 | C30H38N4O4Cl2 | 589.6 | 589 |
| 1040 | C30H38N4O4F2 | 556.6 | 557 |
| 1041 | C30H37N4O4F3 | 574.6 | 575 |
| 1042 | C30H35N4O4F5 | 610.6 | 611 |
| 1043 | C28H44N4O4 | 500.7 | 501 |
| 1044 | C27H41N4O4F | 504.6 | 505 |
| 1045 | C30H46N4O4 | 526.7 | 527 |
| 1046 | C29H44N4O4 | 512.7 | 513 |
| 1047 | C29H44N4O4 | 512.7 | 513 |
| 1048 | C26H38N4O4 | 470.6 | 471 |
| 1049 | C30H39N4O5F | 554.7 | 555 |
| 1050 | C25H38N4O5 | 474.6 | 475 |
| 1052 | C30H45N4O4F | 544.7 | 545 |
| 1053 | C30H38N4O5Br2 | 694.5 | 695* |
| 1058 | C27H42N4O5 | 502.6 | 503 |
| 1061 | C29H47N5O4 | 529.7 | 530 |
| 1062 | C32H45N5O5 | 579.7 | 580 |
| 1065 | C32H41N4O6F | 596.7 | 597 |
| 1066 | C32H40N4O6Br2 | 736.5 | 737* |
| 1068 | C31H42N4O5 | 550.7 | 551 |
| 1069 | C31H42N4O5 | 550.7 | 551 |
| 1071 | C32H43N4O4F | 566.7 | 567 |
| 1072 | C31H42N4O5 | 550.7 | 551 |
| 1074 | C30H39N5O5 | 549.7 | 550 |
| 1075 | C27H41N5O4 | 499.6 | 500 |
| 1076 | C31H41N5O5 | 563.7 | 564 |
| 1078 | C28H36N5O5F | 541.6 | 542 |
| 1079 | C29H39N5O5 | 537.7 | 538 |
| 1080 | C29H39N5O5 | 537.7 | 538 |
| 1081 | C30H41N5O5 | 551.7 | 552 |
| 1082 | C30H41N5O5 | 551.7 | 552 |
| 1083 | C30H40N4O5 | 536.7 | 537 |
| 1084 | C27H42N4O4 | 486.6 | 487 |
| 1085 | C30H40N4O5 | 536.7 | 537 |
| 1086 | C27H42N4O4 | 486.6 | 487 |
| 1087 | C30H41N5O5 | 551.7 | 552 |
| 1088 | C27H43N5O4 | 501.7 | 502 |
| 1089 | C30H41N5O5 | 551.7 | 552 |
| 1090 | C26H38N4O6 | 502.6 | 503 |
| 1098 | C31H43N5O5 | 565.7 | 566 |
| 1099 | C30H48N4O4 | 528.7 | 529 |
| 1100 | C29H35N4O4F3 | 560.6 | 561 |
| 1101 | C30H40N4O5 | 536.7 | 537 |
| 1103 | C29H38N4O5 | 522.6 | 523 |
| 1104 | C30H39N4O5F | 554.7 | 555 |
| 1105 | C34H46N4O5 | 590.8 | 591 |
| 1106 | C26H46N4O4 | 478.7 | 479 |
| 1107 | C28H50N4O4 | 506.7 | 507 |
| 1108 | C33H46N4O5 | 578.7 | 579 |
| 1109 | C29H36N4O4F2 | 542.6 | 543 |
| 1110 | C29H37N4O5F | 540.6 | 541 |
| 1111 | C26H39N4O4F | 490.6 | 491 |
| 1112 | C29H45N4O4F | 532.7 | 533 |
| 1113 | C32H43N4O5F | 582.7 | 583 |
| 1114 | C29H50N4O4 | 518.7 | 519 |
| 1115 | C30H46N4O5 | 542.7 | 543 |
| 1116 | C28H48N4O4 | 504.7 | 505 |
| 1117 | C30H39N6O4F | 566.7 | 567 |
| 1118 | C29H44N4O5 | 528.7 | 529 |
| 1119 | C32H44N4O5 | 564.7 | 565 |

Notes
*[(M + 2 + H)+]
1. Molecular formulas and molecular weights are calculated automatically from the structure via ActivityBase software (ID Business Solutions, Ltd., Guildford, Surrey, UK).
2. M + H obtained from LC-MS analysis using standard methods.
3. All analyses conducted on material after preparative purification.

3. Biological Methods

The compounds of the present invention were evaluated for their ability to interact at the human ghrelin receptor. A competitive radioligand binding assay, fluorescence assay or Aequorin functional assay can be employed. Such methods can be conducted in a high throughput manner to permit the simultaneous evaluation of many compounds.

Specific assay methods for the human (GHS-R1a), swine and rat GHS-receptors (U.S. Pat. No. 6,242,199, Intl. Pat. Appl. Nos. WO 97/21730 and 97/22004), as well as the canine GUS-receptor (U.S. Pat. No. 6,645,726), and their use in generally identifying agonists and antagonists thereof are known.

Appropriate methods for determining the functional and in vivo activity of compounds of the present invention that interact at the human ghrelin receptor are also described below. In addition, methods established in the art can be used to determine other parameters important for use as pharmaceutical agents, such as pharmacokinetics, Caco-2 permeability, plasma protein binding.

A. Competitive Radioligand Binding Assay (Ghrelin Receptor)

A competitive binding assay at the human growth hormone secretagogue receptor (hGHS-R1a) can be carried out analogously to assays described in the literature. (Bednarek, M. A.; et al. *J. Med Chem.* 2000, 43, 4370-4376; Palucki, B. L.; et al. *Bioorg. Med. Chem. Lett.* 2002, 11, 1955-1957.) See also U.S. patent application Ser. Nos. 11/149,512 and 11/149,731. Binding activity at the gherlin receptor for representative compounds of the present invention is shown in the Examples below.

B. Aequorin Functional Assay (Ghrelin Receptor)

The functional activity of compounds of the invention found to bind to the GHS-R1a receptor can be determined using the methods described in the literature, which can also be used as a primary screen for ghrelin receptor activity in a high throughput fashion. See also U.S. patent application Ser. Nos. 11/149,512 and 11/149,731. (LePoul. E.; et al. *J. Biomol. Screen* 2002, 7, 57-65; Bednarek, M. A.; et al. *J. Med. Chem.* 2000, 43, 4370-4376; Palucki, B. L.; et al. *Bioorg. Med Chem. Lett.* 2001, 11, 1955-1957.) Functional activity at the gherlin receptor for representative compounds of the present invention is presented in the Examples.

C. IP1 Functional Assay (Ghrelin Receptor)

The in-vitro functional potency of compounds of the invention as activators of the ghrelin receptor mediated signaling pathway can also be determined using HEK-293 cells stably expressing the human GHS-R1a.

Methods

A HEK-293 cell line stably expressing the human ghrelin receptor was used to test representative compounds of the invention. Receptor activation was monitored via the formation of myo-Inositol-1-phosphate (IP1), a metabolite of the Gq-protein/phospholipase C pathway, following 30 min incubation of the cells at 37° C. with multiple concentrations, typically 7-8, in the range of 0.001-1000 nM. Incubation was stopped by addition of lysis buffer. Lysates were allowed to incubate at room temperature for 1 h with IP1-d2 and Anti-IP1-cryptate before fluorescence reading. Each data point represents mean±SD of four independent experiments. Myo-inositol-1-phosphate (IP1) was quantified by means of the IP-One HTRF® assay (CisBio, Bedford, Mass., USA). This test constitutes a competitive immunoassay based on the use of cryptate-labeled anti-IP1 MAb and d2-labeled IP1 as indicator reagents. In the absence of endogenous IP1, cryptate Mab and IP-d2 interact and produce a quantifiable FRET (fluorescence energy transfer) signal.

Results

The results of this assay for two exemplary compounds of the invention are shown in FIG. 1.

D. Pharmacokinetic Analysis of Representative Compounds of the Invention

The pharmacokinetic behavior of compound of the invention can be ascertained by methods well known to those skilled in the art. (Wilkinson, G. R. "Pharmacokinetics: The Dynamics of Drug Absorption, Distribution, and Elimination" in *Goodman & Gilman's The Pharmacological Basis of Therapeutics*, Tenth Edition, Hardman, J. G.; Limbird, L. E., Eds., McGraw Hill, Columbus, Ohio, 2001, Chapter 1.) The following method was used to investigate the pharmacokinetic parameters (elimination half-life, total plasma clearance, etc.) for intravenous, subcutaneous and oral administration of compounds of the present invention. See also U.S. patent application Ser. Nos. 11/149,512 and 11/149,731 and Intl. Pat. Appl. No. PCT/US2007/017905. Oral bioavailability data for representative compounds of the present invention are presented in the Examples below.

E. Gastric Emptying in Fasted Rat Model

To examine the effects of compounds of the invention in a model for gastroparesis, compounds were evaluated for possible effects on gastric emptying in fasted rats. This model is used to determine the potential of compounds of the invention to promote motility in fasted rats.

Methods

1. Overnight-fasted rats (male, Wistar, 200 g, n=5/group) were given a meal (2 mL) of methylcellulose (2%) by intragastric gavage. The meal was labeled with phenol red (0.05%).
2. Test articles (dosed at various concentrations, typically 1, 3, 10, 30 mg/kg), vehicle and positive control (metoclopramide, a 5-HT ligand and prokinetic agent currently prescribed for the treatment of GI disorders, including gastroparesis) were administered by oral gavage immediately after the meal (time=0).
3. Animals were sacrificed 15 minutes later; the stomach was immediately removed and homogenized in 0.1 N NaOH and centrifuged.
4. Total phenol red remaining in the stomach was quantified by a colorimetric method at 560 nm.
5. A 30% or more increase in gastric emptying (as compared to the vehicle control) was considered significant.
6. One-way ANOVA, Dunnet's post-hoc statistical test was applied Results The effects of representative compounds of the present invention on gastric emptying using this rat model are presented in the Examples below.

F. Gastric Emptying and Intestinal Transit in Rat Model of Postoperative Ileus

This clinically relevant model for POI is adapted from that of Kalff. (Kalff, J. C.; Schraut, W. H.; Simmons, R. L.; Bauer, A. J. *Ann. Surg.* 1998, 228, 652-663.) Other known models can also be used to study the effect of compounds of the invention. (Trudel, L.; Bouin, M.; Tomasetto, C.; Eberling, P.; St-Pierre, S.; Bannon, P.; L'Heureux, M. C.; Poitras, P. *Peptides* 2003, 24, 531-534; (b) Trudel, L.; Tomasetto, C.; Rio, M. C.; Bouin, M.; Plourde, V.; Eberling, P.; Poitras, P. *Am. J. Physiol.* 2002, 282, G948-G952.)

Animals
1. Rat, Sprague-Dawley, male, ~300 g.
2. Fasted O/N prior to study.

Induction of Post-Operative Ileus (POI)
1. Isofluorane anaesthesia under sterile conditions.
2. Midline abdominal incision.
3. Intestines and caecum are eviscerated and kept moist with saline.
4. The intestines and caecum are manipulated along its entire length with moist cotton applicators analogous to the 'running of the bowel' in the clinical setting. This procedure was timed to last for 10 min.
5. Intestines are gently replaced into the abdomen and the abdominal wound was stitched closed under sterile conditions.

Dosing
1. Rat are allowed to recover from isofluorane anaesthesia.
2. Test compounds (or vehicle) are administered intravenously via previously implanted jugular catheter.
3. Immediate intragastric gavage of methylcellulose (2%) labeled with radioactive $^{99m}$Tc, t=0.

Experimental
1. At t=15 min, animal are euthanized with $CO_2$.
2. Stomach and 10 cm sections along the small intestine are to be immediately ligated, out and placed in tubes for measuring of $^{99m}$Tc in gamma counter.
3. Stomach emptying and small intestinal transit are measured by calculation of the geometric mean.

$$\text{Geometric mean} = \Sigma(\% \text{ total radioactivity} \times \text{number of segment})/100$$

G. Growth Hormone Response to Test Compounds

The compounds of the invention likewise can be tested in a number of animal models for their effect on OH release. For example, rats (Bowers, C. Y.; Momany, F.; Reynolds, G. A.; Chang, D.; Hong, A.; Chang, K. *Endocrinology* 1980, 106, 663-667), dogs (Hickey, G.; Jacks, T.; Judith, F.; Taylor, J.; Schoen, W. R.; Krupa, D.; Cunningham. P.; Clark, J.; Smith, R. G. *Endocrinology* 1994, 134, 695-701; Jacks, T.; Hickey, G.; Judith, F.; Taylor, J.; Chen, H.; Krupa, D.; Feeney, W.; Schoen, W. R.; Ok, D.; Fisher, M.; Wyvratt, M.; Smith, R. J. *Endocrinology* 1994, 143, 399-406; Hickey, G. J.; Jacks, T. M.; Schleim, K. D.; Frazier, E.; Chen, H. Y.; Krupa, D.; Feeney, W.; Nargund, R. P.; Patchett, A. A.; Smith, R. G. J, *Endocrinol.* 1997, 152, 183-192), and pigs (Chang, C. H.; Rickes, E. L.; Marsilio, F.; McGuire, L.; Cosgrove, S.; Taylor, J.; Chen, H. Y.; Feighner, S.; Clark, J. N.; Devita, R.; Schoen, W. R.; Wyvratt, M.; Fisher, M.; Smith, R. G.; Hickey, G. *Endocrinology* 1995, 136, 1065-1071; (b) Peschke, B.; Hanse, B. S. *Bioorg. Med Chem. Lett.* 1999, 9, 1295-1298) have all been successfully utilized for the in vivo study of the effects of GHS and would likewise be applicable for investigation of the effect of ghrelin agonists on GH levels. The measurement of ghrelin of GH levels in plasma after appropriate administration of compounds of the invention can be performed using radioimmunoassay via standard methods known to those in the art. (Deghenghi, R.; et al. *Life Sciences* 1994, 54, 1321-1328.) Binding to tissue can be studied using whole body autoradiography after dosing of an animal with test substance containing a radioactive label. (Ahnfelt-Rønne, I.; Nowak, J.; Olsen, U. B. Do growth hormone-releasing peptides act as ghrelin secretagogues? *Endocrine* 2001, 14, 133-135.)

The following method is employed to determine the temporal pattern and magnitude of the growth hormone (GH) response to test compounds, administered either systemically or centrally. Analogous methods can be used for other appropriate animal models, such as dogs and cynomolgus monkeys.

Dosing and Sampling Procedures for In Vivo Studies of GH Release

Adult male Sprague Dawley rats (225-300 g) are purchased from Charles River Canada (St. Constant, Canada) and individually housed on a 12-h light, 12-h dark cycle (lights on, time: 0600-1800) in a temperature (22±1° C.)- and humidity-controlled room. Purina rat chow (Ralston Purina Co., St. Louis, Mo.) and tap water are freely available. For these studies, chronic intracerebroventricular (icy) and intracardiac venous cannulas are implanted under sodium pentobarbital (50 mg/kg, ip) anesthesia using known techniques. The placement of the icy cannula are verified by both a positive drinking response to icv carbachol (100 ng/10 μl) injection on the day after surgery and methylene blue dye at the time of sacrifice. After surgery, the rats are placed directly in isolation test chambers with food and water freely available until body weight returned to preoperative levels (usually within 5-7 d). During this time, the rats are handled daily to minimize any stress associated with handling on the day of the experiment. On the test day, food is removed 1.5 h before the start of sampling and is returned at the end. Test samples at various dosing levels or normal saline were administered either intravenously or orally at two different time points during a 6-h sampling period. The times 1100 and 1300 are chosen because they reflect typical peak and trough periods of GH secretion, as previously documented. The human ghrelin peptide (5 μg. Phoenix Pharmaceuticals, Inc., Belmont, Calif.) is used as a positive control in the experiments and was diluted in normal saline just before use. To assess the central actions of test compounds on pulsatile OH release, a 10-fold lower dose of the test sample or normal saline is administered icy at the same time points, 1100 and 1300. Blood samples (0.35 mL) is withdrawn every 15 min over the 6-h sampling period (time: 1000-1600) from all animals. To document the rapidity of the GH response to the test compound, an additional blood sample is obtained 5 min after each injection. All blood samples are immediately centrifuged, and plasma is separated and stored at −20° C. for subsequent GH assay. To avoid hemodynamic disturbance, the red blood cells are resuspended in normal saline and returned to the animal after removal of the next blood sample. All animal studies are conducted under procedures approved by an animal care oversight committee.

GH Assay Method

Plasma GH concentrations are measured in duplicate by double antibody RIA using materials supplied by the NIDDK Hormone Distribution Program (Bethesda, Md.). The averaged plasma GH values for 5-6 rats per group are reported in terms of the rat GH reference preparation. All samples with values above the range of interest are reassayed at dilutions ranging from 1:2 to 1:10.

Results

Figure 2:
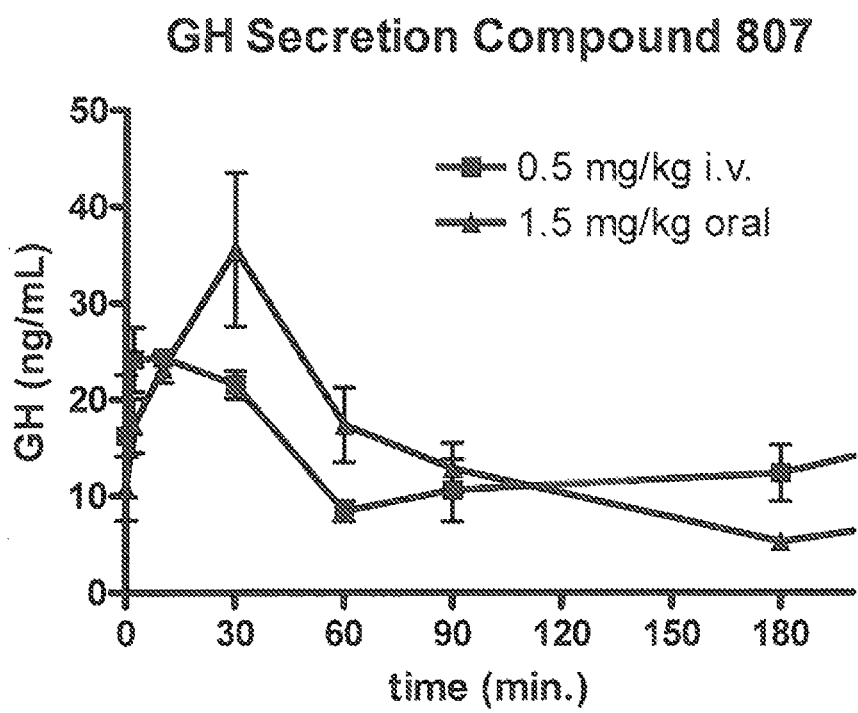
FIG. 2 shows a graph depicting the effect on pulsatile growth hormone release for an exemplary compound of the present invention.
Figure 3:
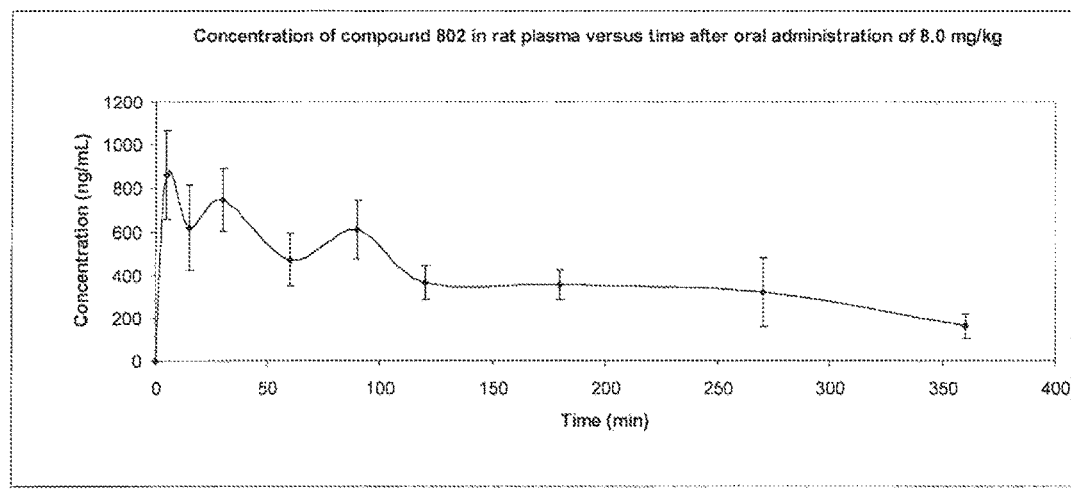
FIG. 3 shows graphs depicting pharmacokinetic parameters for exemplary compounds of the present invention, specifically after oral administration of 8 mg/kg compound 802 (panel A) and after oral administration of 8 mg/kg compound 807 (panel B).
Figure 3:
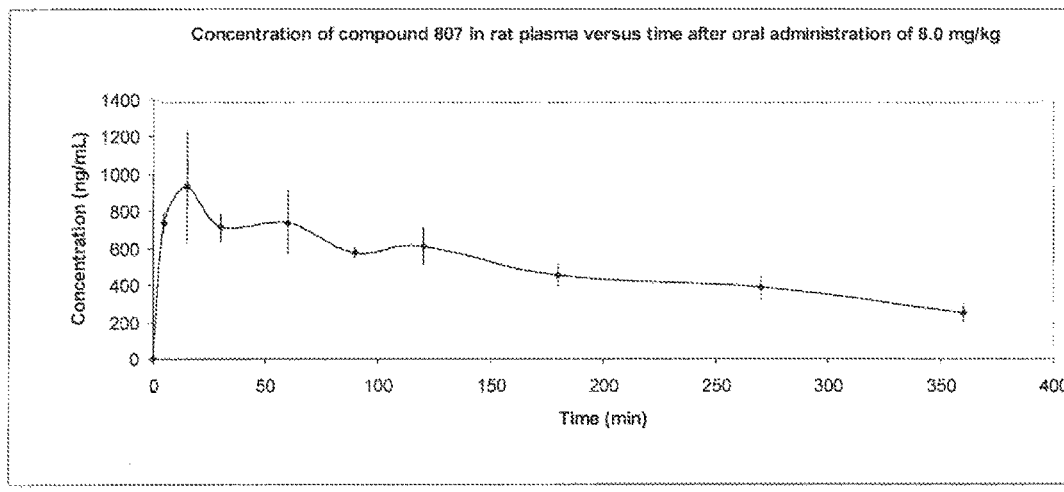
Figure 4:
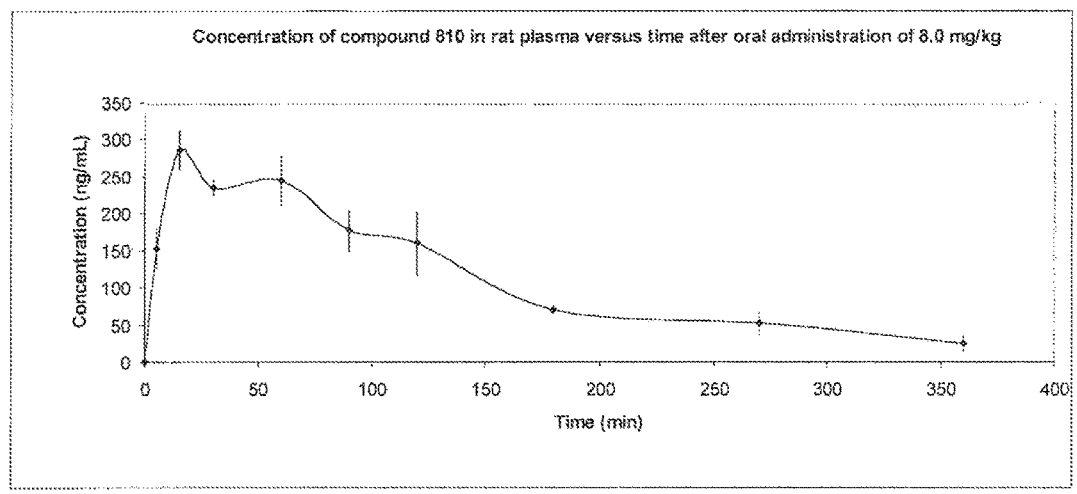
FIG. 4 shows graphs depicting pharmacokinetic parameters for exemplary compounds of the present invention, specifically after oral administration of 8 mg/kg compound 810 (panel A) and after oral administration of 8 mg/kg compound 819 (panel B).
Figure 4:
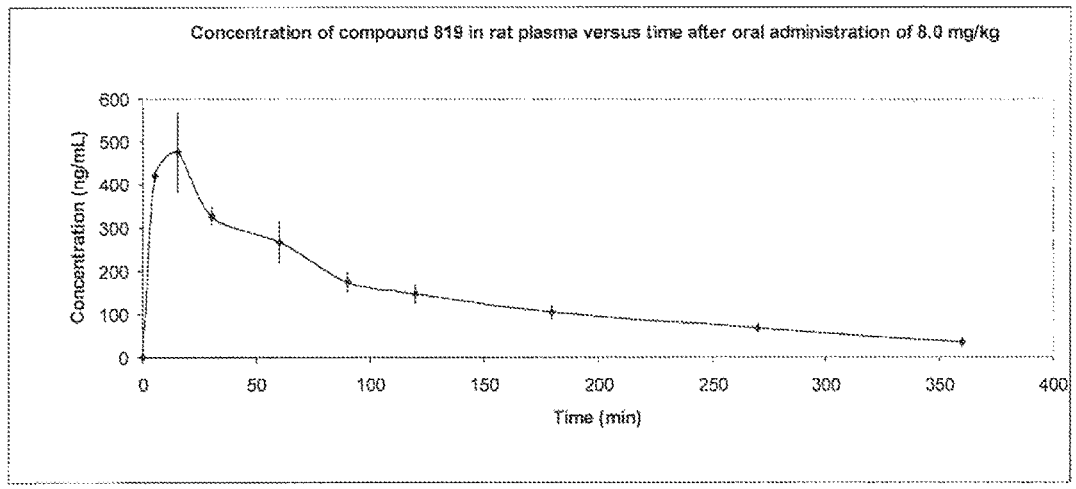
Figure 5:
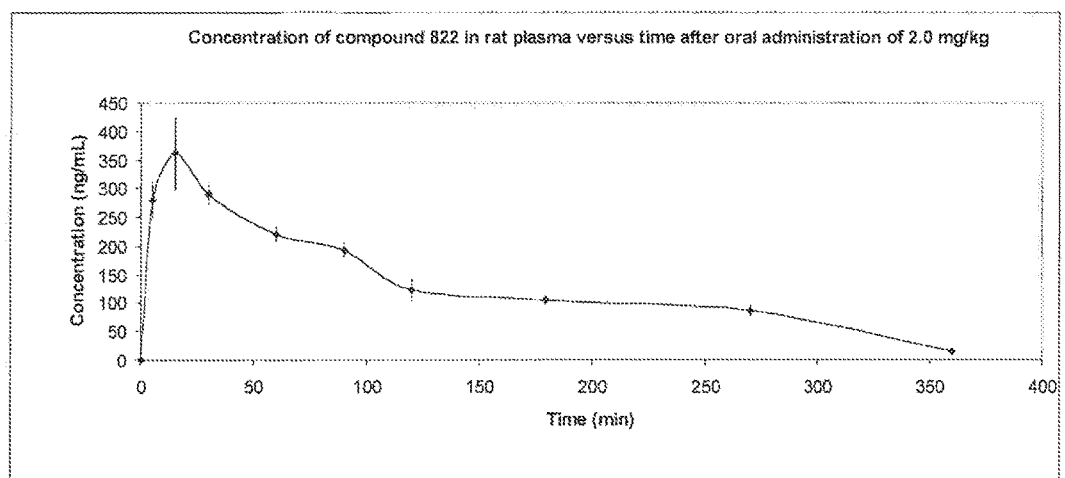
FIG. 5 shows graphs depicting pharmacokinetic parameters for exemplary compounds of the present invention, specifically after oral administration of 2 mg/kg compound 822 (panel A) and after oral administration of 8 mg/kg compound 825 (panel B).
Figure 5:
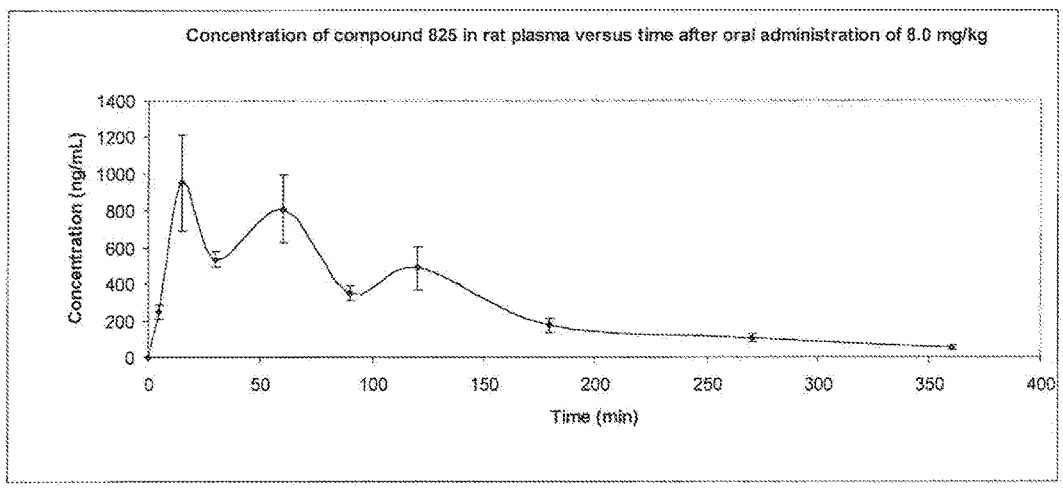
Figure 6:
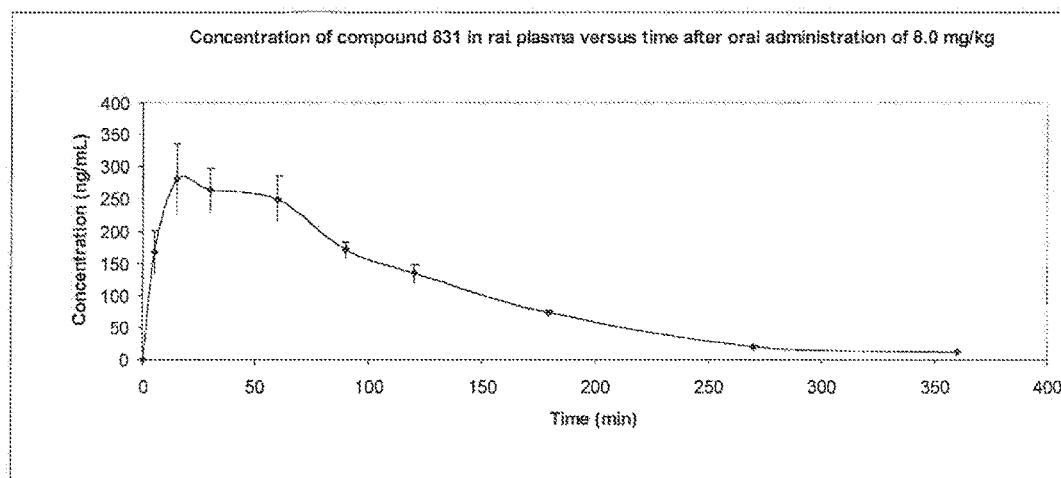
FIG. 6 shows graphs depicting pharmacokinetic parameters for exemplary compounds of the present invention, specifically after oral administration of 8 mg/kg compound 831 (panel A) and after oral administration of 8 mg/kg compound 854 (panel B).
Figure 6:
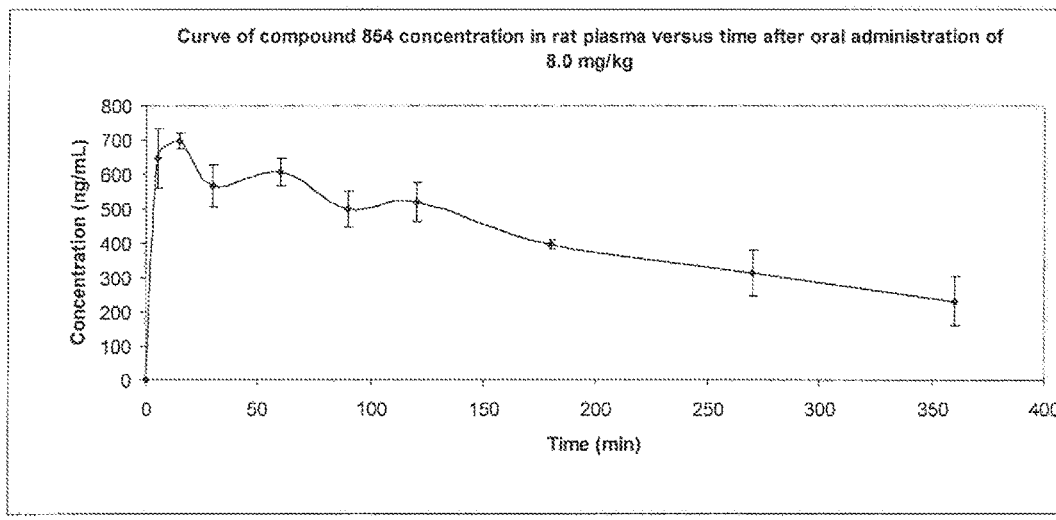
Figure 7:
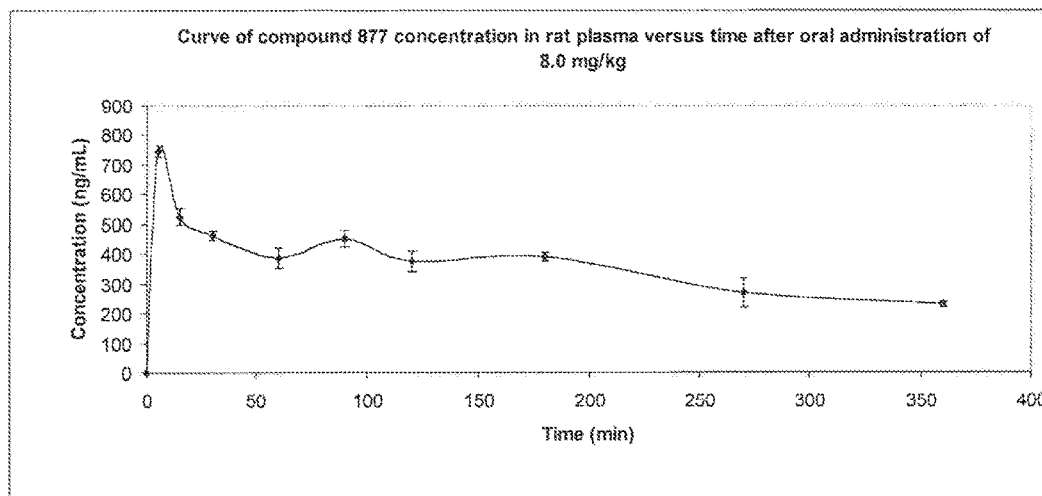
FIG. 7 shows graphs depicting pharmacokinetic parameters for exemplary compounds of the present invention, specifically after oral administration of 8 mg/kg compound 877 (panel A) and after oral administration of 8 mg/kg compound 968 (panel B).
Figure 7:
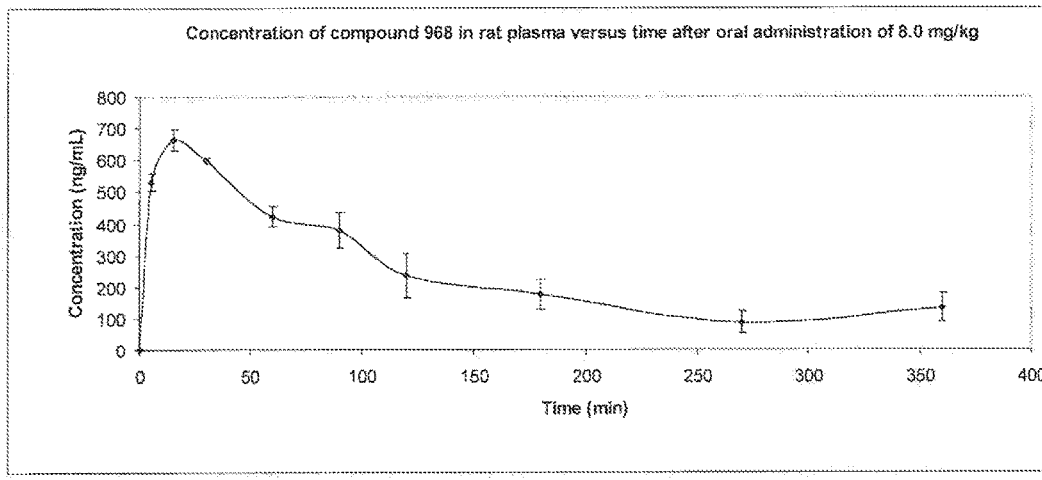
Figure 8:
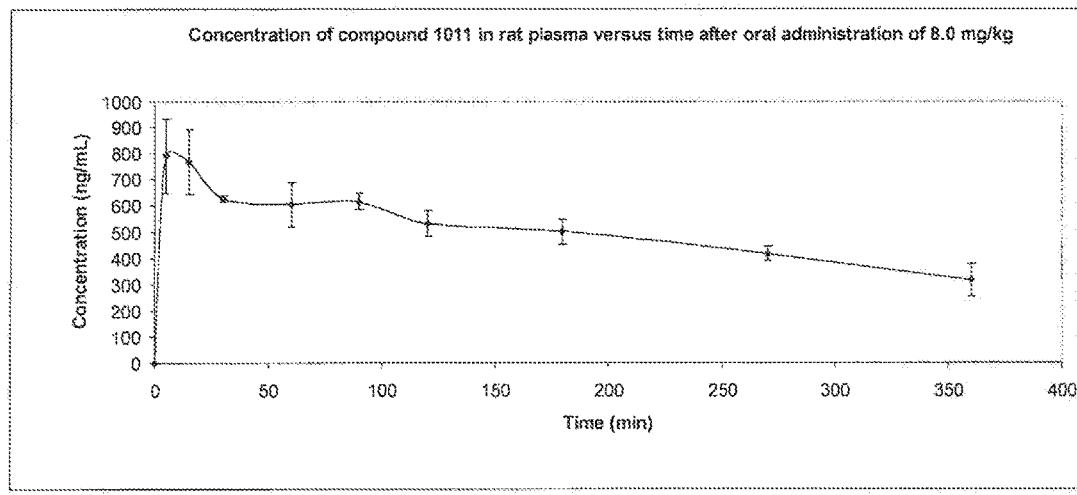
FIG. 8 shows graphs depicting pharmacokinetic parameters for exemplary compounds of the present invention, specifically after oral administration of 8 mg/kg compound 1011 (panel A) and after oral administration of 8 mg/kg compound 1069 (panel B).
Figure 8:
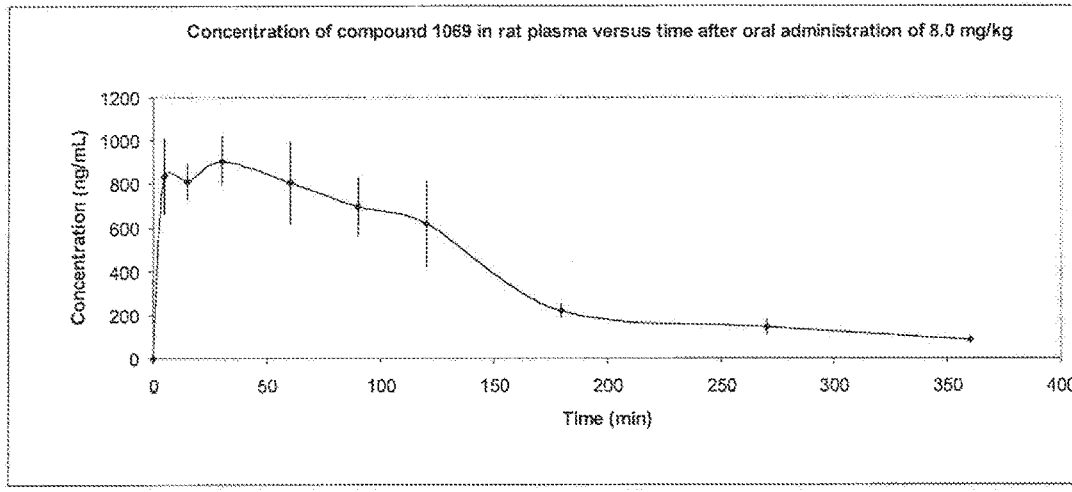

The effects of an exemplary compound of the invention on the secretion of growth hormone in cynomolgus monkeys after both intravenous and oral administration are presented in FIG. 2.

H. Mouse Model of Cancer Cachexia

Tumor cachexia is considered the major reason for mortality, rapidly declining quality of life and limitation of therapy in advanced tumor patients. Since agonism of the ghrelin receptor has been associated with increased food intake and the generation of a positive overall energy balance, the compounds of the present invention have applications to the treatment of this disorder. The following method was designed to investigate the effects of test compounds as compared to ghrelin peptide on tumor cachexia in the G361 melanoma model grown as a subcutaneous xenograft in BALB/c nu/nu mice. (Mori M, Yamaguchi K, Honda S, et al. *Cancer Res.* 1991, 51, 6656-6659.) Additional models are known in the art. (Emery, P. W. *Nutrition* 1999, 15, 600-603.)

For the method, 60 tumour-bearing mice are randomised 12 days post-inoculation into two sets of 5 groups containing 6 animals each. At initiation of treatment, the average body weight loss of Set 1 and Set 2 animals relative to the initial average body weight is determined. Treatment of Set 1 and 2 animals commences on Days 12 and 16, after tumor inoculation, respectively. Groups 1 and 6 receive vehicle i.v. s.c. or oral (depending on the mode of administration of the test compound) bid alone, while Groups 5 and 10 were administered rat ghrelin peptide s.c. (1 mg/kg; bid, 6 h apart) as a positive control. Test compounds are administered i.v., s.c. or oral twice daily, 6 h apart, at three dose levels (for example 3, 10, 30 mg/kg) for 20-40 consecutive days. Mice are culled during the study according to predetermined criteria including >15% initial body weight loss and/or tumor volume in excess of 2000 $mm^3$ and/or display of severe clinical signs.

Body weights are measured, along with quantity of food and water consumption. In addition, plasma levels of cholesterol, triglyceride, non-esterified fatty acids and blood glucose are determined during the course of treatment to provide further measures of the effects of the test compounds on the overall health of the animal.

I. Ex-vivo Potency Evaluation on the Rat Stomach Fundus

This method is employed to evaluate the potency of compounds of the invention as a prokinetic agent by treatment of rat stomach fundus strips in an organ bath ex vivo in the presence or absence of electrical field stimulation (EFS) using ghrelin peptide as a reference.

Methods

Fundus strips (approximately 0.4×0.1 cm) were cut from the stomach of adult male Wistar rats parallel to the circular muscle fibers. They were placed between two platinum ring electrodes, 1 cm apart (Radnoti, ADInstruments, USA) in 10 ml tissue baths containing Krebs solution bubbled with 5% $CO_2$ in $O_2$ and maintained at 37° C. Tissues were suspended under 1.5 g resting tension. Changes of tension were measured isometrically with force transducers and recorded with a PowerLab 8/30 data acquisition system (ADInstruments, USA). Tissues were allowed to equilibrate for 60 min during which time bath solutions were changed every 15 min.

EFS was achieved by applying 0.5 ms pulses, 5 Hz frequency, at a maximally effective voltage of 70 V. EFS was applied for 30 sec at 3 min intervals for a 30 min initial period. This initial period was separated by a 5 min interval with wash out of the bath solution. Then, a second period of stimulation was started. After obtaining consistent EFS-evoked contractions (after three or four 30 sec stimulations), the effects of ghrelin, test compounds at various concentrations (for example 0.01-10 µM), L-NAME (300 µM, as control) or their respective vehicles, applied non-cumulatively, on responses to EFS were studied over a 30 min period. Responses to the agents were measured and expressed as % of the mean of three or four pre-drug responses to EFS. All compounds were dissolved at 1 mM in distilled water or MeOH, as stock solutions.

Results $EC_{50}$ values for contractility were 5 nM for ghrelin peptide, 300 nM for compound 801 and 150 nM for compound 807 indicating a lower potency of the synthetic macrocyclic ghrelin agonists relative in the isolated rat stomach fundus system.

J. Plasma Protein Binding

The pharmacokinetic and pharmacodynamic properties of drugs are largely a function of the reversible binding of drugs to plasma or serum proteins such as albumin and $\alpha_1$-acid glycoprotein. In general, only unbound drug is available for diffusion or transport across cell membranes, and for interaction at the pharmacological target. On the other hand, drugs with low plasma protein binding generally have large volumes of distribution and rapid clearance since only unbound drug is available for glomerular filtration and, in some cases, hepatic clearance. Thus, the extent of plasma protein binding can influence efficacy, distribution and elimination. The ideal range for plasma protein binding is in the range of 87-98% for most drug products.

Protein binding studies were performed using human plasma. Briefly, 96-well microplates were used to incubate various concentrations of the test article for 60 min at 37° C. Bound and unbound fractions are separated by equilibrium dialysis, where the concentration remaining in the unbound fraction is quantified by LC-MS or LC-MS-MS analysis. Drugs with known plasma protein binding values such as quinine (~35%), warfarin (~98%) and naproxen (~99.7%) were used as reference controls.

Results for representative compounds of the invention are summarized in the Examples.

K. Assay for Cytochrome P450 Inhibition

Cytochrome P450 enzymes are implicated in the phase I metabolism of drugs. The majority of drug-drug interactions are metabolism-based and, moreover, these interactions typically involve inhibition of cytochrome P450s. Six CYP450 enzymes (CYP1A2, CYP2C8, CYP2C9, CYP2C19, CYP2D6 and CYP3A4) appear to be commonly responsible for the metabolism of most drugs and the associated drug-drug interactions. Assays to determine the binding of compounds of the invention to the various metabolically important isoforms of cytochrome P450 metabolizing enzymes are commercially available, for example NoAb BioDiscoveries (Mississaugua, ON, Canada) and Absorption Systems (Exton, Pa., USA). As well, a number of appropriate methods have been described or reviewed in the literature. (White, R. E. *Ann. Rev. Pharmacol. Toxicol.* 2000, 40, 133-157; Li, A. P. *Drug. Disc. Today* 2001, 6, 357-366; Turpeinen, M.; Korhonen, L. E. Tolonen, A.; et al. *Eur. J. Pharm. Sci.* 2006, 29, 130-138.)

The key aspects of the experimental method were as follows:

1. Assay was performed on microsomes (Supersomes®, BD Gentest, Becton-Dickinson) prepared from insect cells expressing individual human CYP-450 subtypes, specifically:
   CYP subtypes: 1A2, 2A6, 2B6, 2C8, 2C9, 2C19, 2D6, 2E1, 3A4
   Two substrates are typically tested for CYP-3A4 as this enzyme exhibits complex inhibition kinetics
2. Assays monitored, via fluorescence detection, the formation of a fluorescent metabolite following incubation of the microsomes with a specific CYP substrate.
3. Compounds of the present invention were tested in duplicate samples at eight test concentrations using 3-fold serial dilutions (concentration range of 0.0457 to 100 µM).

4. For each CYP-450 enzyme, a specific inhibitor was tested in duplicate at eight concentrations as a positive control.
5. The concentration of the inhibitor or test compound that inhibited metabolite formation by 50% ($IC_{50}$) was calculated by non-linear regression analysis of the % inhibition vs. log concentration (M) curve.

Results for representative compounds of the invention are summarized in the Examples.

L. Determination of Caco-2 Permeability

The Caco-2 cell line, derived from a human colorectal carcinoma, has become an established in vitro model for the prediction of drug absorption across the human intestine. (Sun, D.; Yu, L. X.; Hussain, M. A.; Wall, D. A.; Smith, R. L.; Amidon, G. L. *Curr. Opin. Drug Discov. Devel.* 2004, 7, 75-85; Bergstrom, C. A. *Basic Clin. Pharmacol. Toxicol.* 2005, 96, 156-61; Balimane, P. V.; Han, Y. H.; Chong, S. *AAPS J.* 2006, 8, EI-13; Shah, P.; Jogani, V.; Bagchi, T.; Misra, A. *Biotechnol. Prog.* 2006, 22, 186-198.) When cultured on semi-permeable membranes, Caco-2 cells differentiate into a highly functionalized epithelial barrier with remarkable morphological and biochemical similarity to the small intestinal columnar epithelium. Fully differentiated cell monolayers can be used to assess the membrane transport properties of novel compounds. In addition, the apparent permeability coefficients ($P_{app}$) obtained from Caco-2 cell transport studies have been shown to reasonably correlate with human intestinal absorption.

Assays to determine the permeability of compounds of the invention utilizing Caco-2 cells are commercially available, for example NoAb BioDiscoveries (Mississaugua, ON, Canada) and Absorption Systems (Exton, Pa., USA).

Alternatively, parallel artificial membrane permeability assays (PAMPA) can be utilized to assess intestinal permeability. (Avdeef, A. *Expert Opin. Drug. Metab. Toxicol.* 2005, 1, 325-42.)

Method

Permeability across the Caco-2 cell layer was determined by growing the cells on a membrane placed between two (donor and acceptor) chambers. Drug candidates are typically added to the apical (A) side of the cell layer and their appearance in the basolateral (B) side is measured over incubation time. Permeability in this direction represents intestinal absorption. Permeability may also be determined from the basolateral to the apical side of the Caco-2 cell. A higher apical to basolateral $P_{app}$, compared to the basolateral to apical $P_{app}$, is indicative of carrier-mediated transport, P-gp mediated transport is suggested when a higher basolateral to apical $P_{app}$ is observed relative to the apical to basolateral $P_{app}$.

Permeability (10 µM) for compounds of the invention in the apical to basolateral and basolateral to apical direction were tested in duplicate. Samples will be collected from the donor and acceptor chambers at the beginning (0 min) and following 60 min of incubation at 37° C. and stored frozen at −70° C. until bioanalysis. Samples for each test compound generated from the Caco-2 permeability assay were further analyzed by LC-MS-MS. The permeability of [$^3$H]-mannitol and [$^3$H]-propranolol were determined in parallel as controls.

The permeability coefficient ($P_{app}$) of each compound and radiolabeled standard was determined using the following equation:

$$P_{app} = \frac{dQ}{dT} \times 1/C_1 \times 1/A$$

where dQ/dT represents the permeability rate, $C_i$ denotes the initial concentration in the donor compartment, and A represents the surface area of the filter. $C_i$ is determined from the mean concentration of duplicate samples taken prior to addition to the donor compartment. Permeability rates were calculated by plotting the cumulative amount of compound measured in the acceptor compartment over time and determining the slope of the line by linear regression analysis. The duplicate and mean apical to basolateral and basolateral to apical $P_{app}$'s were reported for each compound and standard.

Results for representative compounds of the invention are summarized in the Examples.

M. Activation-Desensitization Profile

It is well-known that agonists of G-protein coupled receptors can induce desensitization or tachyphylaxis, thereby limiting the potential of agents acting at the receptor as therapeutics for chronic use. (Luttrell, L. M. *Methods Mol. Biol.* 2006, 332, 3-49; Kenakin, T. *Ann. Rev. Pharmacol. Toxicol.* 2002, 42, 349-379; Kenakin, T. *Nat. Rev. Drug Discov.* 2002, 1, 103-110; Ferguson, S. S. *Pharmacol. Rev.* 2001, 53, 1-24.) This method is used to assess the receptor activation-desensitization profile of compounds of the present invention relative to reference agonists using HEK293 cells stably expressing hGHS-R1a.

Methods
1. Ghrelin, GHRP-6 and capromorelin were used as reference agonists
2. Agonist-induced $Ca^{+2}$ fluxes were measured after loading with $Ca^{+2}$ indicator Fluo-4-AM.
3. The negative logarithm of the agonist concentration causing 50% maximal stimulation of hGHS-R1a was calculated ($pEC_{50}$)
4. The negative logarithm of the pre-incubation concentration reducing the maximum response to ghrelin to 50% of its control value was calculated ($pDC_{50}$)
5. To compare the relative activation-desensitization profile of ghrelin agonists, the difference between $pEC_{50}$ and $pDC_{50}$ values for individual compounds were calculated, with the higher positive numbers expected to have less desensitization potential and hence suitable for chronic applications as therapeutics.

Results

| Compound | Δ(activity − desensitization) ($pEC_{50}$ − $pDC_{50}$) |
|---|---|
| Ghrelin | 0.85 |
| GHRP-6 | 0.60 |
| Capromorelin | 0.91 |
| 801 | 3.30 |
| 807 | 3.08 |
| 826 | 1.90 |

The 100 to 1000-fold potency difference between receptor activation and desensitization suggests that compounds of the present invention should be comparatively less susceptible to inducing ghrelin receptor desensitization upon repeated exposure.

4. Pharmaceutical Compositions

The macrocyclic compounds of the present invention or pharmacologically acceptable salts thereof according to the invention may be formulated into pharmaceutical compositions of various dosage forms. To prepare the pharmaceutical compositions of the invention, one or more compounds, including optical isomers, enantiomers, diastereomers, racemates or stereochemical mixtures thereof, or pharmaceutically acceptable salts thereof as the active ingredient is intimately mixed with appropriate carriers and additives according to techniques known to those skilled in the art of pharmaceutical formulations.

A pharmaceutically acceptable salt refers to a salt form of the compounds of the present invention in order to permit their use or formulation as pharmaceuticals and which retains the biological effectiveness of the free acids and bases of the specified compound and that is not biologically or otherwise undesirable. Examples of such salts are described in *Handbook of Pharmaceutical Salts: Properties. Selection, and Use*, Wermuth, C. G. and Stahl, P. H. (eds.), Wiley-Verlag Helvetica Acta, Zürich, 2002 [ISBN 3-906390-26-8]. Examples of such salts include alkali metal salts and addition salts of free acids and bases. Examples of pharmaceutically acceptable salts, without limitation, include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, xylenesulfonates, phenylacetates, phenylpropionates, phenylbutyrates, citrates, lactates, γ-hydroxybutyrates, glycollates, tartrates, methanesulfonates, ethane sulfonates, propanesulfonates, toluenesulfonates, naphthalene-1-sulfonates, naphthalene-2-sulfonates, and mandelates.

If an inventive compound is a base, a desired salt may be prepared by any suitable method known to those skilled in the art, including treatment of the free base with an inorganic acid, such as, without limitation, hydrochloric acid, hydrobromic acid, hydroiodic, carbonic acid, sulfuric acid, nitric acid, phosphoric acid, and the like, or with an organic acid, including, without limitation, formic acid, acetic acid, propionic acid, maleic acid, succinic acid, mandelic acid, fumaric acid, malonic acid, pyruvic acid, oxalic acid, stearic acid, ascorbic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid, 2-hydroxyethanesulfonic acid, benzenesulfonic acid, cyclohexyl-aminosulfonic acid or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine, lysine and arginine; ammonia; primary, secondary, and tertiary amines such as ethylenediamine. N,N'-dibenzylethylenediamine, diethanolamine, choline, and procaine, and cyclic amines, such as piperidine, morpholine, and piperazine; as well as inorganic salts derived from sodium, calcium, potassium, magnesium, manganese, iron, copper, zinc, aluminum, and lithium.

The carriers and additives used for such pharmaceutical compositions can take a variety of forms depending on the anticipated mode of administration. Thus, compositions for oral administration may be, for example, solid preparations such as tablets, sugar-coated tablets, hard capsules, soft capsules, granules, powders and the like, with suitable carriers and additives being starches, sugars, binders, diluents, granulating agents, lubricants, disintegrating agents and the like. Because of their ease of use and higher patient compliance, tablets and capsules represent the most advantageous oral dosage forms for many medical conditions.

Similarly, compositions for liquid preparations include solutions, emulsions, dispersions, suspensions, syrups, elixirs, and the like with suitable carriers and additives being water, alcohols, oils, glycols, preservatives, flavoring agents, coloring agents, suspending agents, and the like. Typical preparations for parenteral administration comprise the active ingredient with a carrier such as sterile water or parenterally acceptable oil including polyethylene glycol, polyvinyl pyrrolidone, lecithin, arachis oil or sesame oil, with other additives for aiding solubility or preservation may also be included. In the case of a solution, it can be lyophilized to a powder and then reconstituted immediately prior to use. For dispersions and suspensions, appropriate carriers and additives include aqueous gums, celluloses, silicates or oils.

The pharmaceutical compositions according to embodiments of the present invention include those suitable for oral, rectal, topical, inhalation (e.g., via an aerosol) buccal (e.g., sub-lingual), vaginal, topical (i.e., both skin and mucosal surfaces, including airway surfaces), transdermal administration and parenteral (e.g., subcutaneous, intramuscular, intradermal, intraarticular, intrapleural, intraperitoneal, intrathecal, intracerebral, intracranially, intraarterial, or intravenous), although the most suitable route in any given case will depend on the nature and severity of the condition being treated and on the nature of the particular active agent which is being used.

Compositions for injection will include the active ingredient together with suitable carriers including propylene glycol-alcohol-water, isotonic water, sterile water for injection (USP), emulPhor™-alcohol-water, cremophor-EL™ or other suitable carriers known to those skilled in the art. These carriers may be used alone or in combination with other conventional solubilizing agents such as ethanol, propylene glycol, or other agents known to those skilled in the art.

Where the macrocyclic compounds of the present invention are to be applied in the form of solutions or injections, the compounds may be used by dissolving or suspending in any conventional diluent. The diluents may include, for example, physiological saline, Ringer's solution, an aqueous glucose solution, an aqueous dextrose solution, an alcohol, a fatty acid ester, glycerol, a glycol, an oil derived from plant or animal sources, a paraffin and the like. These preparations may be prepared according to any conventional method known to those skilled in the art.

Compositions for nasal administration may be formulated as aerosols, drops, powders and gels. Aerosol formulations typically comprise a solution or fine suspension of the active ingredient in a physiologically acceptable aqueous or non-aqueous solvent. Such formulations are typically presented in single or multidose quantities in a sterile form in a sealed container. The sealed container can be a cartridge or refill for use with an atomizing device. Alternatively, the sealed container may be a unitary dispensing device such as a single use nasal inhaler, pump atomizer or an aerosol dispenser fitted with a metering valve set to deliver a therapeutically effective amount, which is intended for disposal once the contents have been completely used. When the dosage form comprises an aerosol dispenser, it will contain a propellant such as a compressed gas, air as an example, or an organic propellant including a fluorochlorohydrocarbon or fluorohydrocarbon.

Compositions suitable for buccal or sublingual administration include tablets, lozenges and pastilles, wherein the active ingredient is formulated with a carrier such as sugar and acacia, tragacanth or gelatin and glycerin.

Compositions for rectal administration include suppositories containing a conventional suppository base such as cocoa butter.

Compositions suitable for transdermal administration include ointments, gels and patches.

Other compositions known to those skilled in the art can also be applied for percutaneous or subcutaneous administration, such as plasters.

Further, in preparing such pharmaceutical compositions comprising the active ingredient or ingredients in admixture with components necessary for the formulation of the compositions, other conventional pharmacologically acceptable additives may be incorporated, for example, excipients, stabilizers, antiseptics, wetting agents, emulsifying agents, lubricants, sweetening agents, coloring agents, flavoring agents, isotonicity agents, buffering agents, antioxidants and the like. As the additives, there may be mentioned, for example, starch, sucrose, fructose, dextrose, lactose, glucose, mannitol, sorbitol, precipitated calcium carbonate, crystalline cellulose, carboxymethylcellulose, dextrin, gelatin, acacia, EDTA, magnesium stearate, talc, hydroxypropylmethylcellulose, sodium metabisulfite, and the like.

In some embodiments, the composition is provided in a unit dosage form such as a tablet or capsule.

In further embodiments, the present invention provides kits including one or more containers comprising pharmaceutical dosage units comprising an effective amount of one or more compounds of the present invention.

The present invention further provides prodrugs comprising the compounds described herein. The term "prodrug" is intended to mean a compound that is converted under physiological conditions or by solvolysis or metabolically to a specified compound that is pharmaceutically active. The "prodrug" can be a compound of the present invention that has been chemically derivatized such that, (i) it retains some, all or none of the bioactivity of its parent drug compound, and (ii) it is metabolized in a subject to yield the parent drug compound. The prodrug of the present invention may also be a "partial prodrug" in that the compound has been chemically derivatized such that, (i) it retains some, all or none of the bioactivity of its parent drug compound, and (ii) it is metabolized in a subject to yield a biologically active derivative of the compound. Known techniques for derivatizing compounds to provide prodrugs can be employed. Such methods may utilize formation of a hydrolyzable coupling to the compound.

The present invention further provides that the compounds of the present invention may be administered in combination with a therapeutic agent used to prevent and/or treat metabolic and/or endocrine disorders, gastrointestinal disorders, cardiovascular disorders, obesity and obesity-associated disorders, central nervous system disorders, bone disorders, genetic disorders, hyperproliferative disorders and inflammatory disorders. Exemplary agents include analgesics (including opioid analgesics), anesthetics, antifungals, antibiotics, antiinflammatories (including nonsteroidal anti-inflammatory agents), anthelmintics, antiemetics, antihistamines, antihypertensives, antipsychotics, antiarthritics, antitussives, antivirals, cardioactive drugs, cathartics, chemotherapeutic agents (such as DNA-interactive agents, antimetabolites, tubulin-interactive agents, hormonal agents, and agents such as asparaginase or hydroxyurea), corticoids (steroids), antidepressants, depressants, diuretics, hypnotics, minerals, nutritional supplements, parasympathomimetics, hormones (such as corticotrophin releasing hormone, adrenocorticotropin, growth hormone releasing hormone, growth hormone, thyrptropin-releasing hormone and thyroid stimulating hormone), sedatives, sulfonamides, stimulants, sympathomimetics, tranquilizers, vasoconstrictors, vasodilators, vitamins and xanthine derivatives.

Subjects suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and birds in ovo.

The present invention is primarily concerned with the treatment of human subjects, but the invention can also be carried out on animal subjects, particularly mammalian subjects such as mice, rats, dogs, cats, livestock and horses for veterinary purposes, and for drug screening and drug development purposes.

In therapeutic use for treatment of conditions in mammals (i.e. humans or animals) for which a modulator, such as an agonist, of the ghrelin receptor is effective, the compounds of the present invention or an appropriate pharmaceutical composition thereof may be administered in an effective amount. Since the activity of the compounds and the degree of the therapeutic effect vary, the actual dosage administered will be determined based upon generally recognized factors such as age, condition of the subject, route of delivery and body weight of the subject. The dosage can be from about 0.1 to about 100 mg/kg, administered orally 1-4 times per day. In addition, compounds can be administered by injection at approximately 0.01-20 mg/kg per dose, with administration 1-4 times per day. Treatment could continue for weeks, months or longer. Determination of optimal dosages for a particular situation is within the capabilities of those skilled in the art.

5. Methods of Use

The compounds of the present invention can be used for the prevention and treatment of a range of medical conditions including, but not limited to, metabolic and/or endocrine disorders, gastrointestinal disorders, cardiovascular disorders, obesity and obesity-associated disorders, central nervous system disorders, bone disorders, genetic disorders, hyperproliferative disorders, inflammatory disorders and combinations thereof where the disorder may be the result of multiple underlying maladies. In particular embodiments, the disease or disorder is irritable bowel syndrome (IBS), non-ulcer dyspepsia, Crohn's disease, gastroesophogeal reflux disorders, constipation, ulcerative colitis, pancreatitis, infantile hypertrophic pyloric stenosis, carcinoid syndrome, malabsorption syndrome, diarrhea, diabetes including diabetes mellitus (type II diabetes), obesity, atrophic colitis, gastritis, gastric stasis, gastrointestinal dumping syndrome, postgastroenterectomy syndrome, celiac disease, an eating disorder or obesity. In other embodiments, the disease or disorder is congestive heart failure, ischemic heart disease or chronic heart disease. In still other embodiments, the disease or disorder is osteoporosis and/or frailty, congestive heart failure, accelerating bone fracture repair, metabolic syndrome, attenuating protein catabolic response, cachexia, protein loss, impaired or risk of impaired wound healing, impaired or risk of impaired recovery from burns, impaired or risk of impaired recovery from surgery, impaired or risk of impaired muscle strength, impaired or risk of impaired mobility, altered or risk of altered skin thickness, impaired or risk of impaired metabolic homeostasis or impaired or risk of impaired renal homeostasis. In other embodiments, the disease or disorder involves facilitating neonatal development, stimulating growth hormone release in humans, maintenance of muscle strength and function in humans, reversal or prevention of frailty in humans, prevention of catabolic side effects of glucocorticoids, treatment of osteoporosis, stimulation and increase in muscle mass and muscle strength, stimulation of the immune system, acceleration of wound healing, acceleration of bone fracture repair, treatment of renal failure or insufficiency resulting in growth retardation, treatment of short stature, treatment of obesity and growth retardation, accelerating the recovery and reducing hospitalization of burn patients, treatment of intrauterine growth retardation, treatment of skeletal dysplasia, treatment of hypercortisolism, treatment of Cushing's syndrome, induction of pulsatile growth hormone release, replacement of growth hormone in stressed patients, treatment of osteochondrodysplasias, treatment of Noonans syndrome, treatment of schizophrenia, treatment of depression, treatment of Alzheimer's disease, treatment of emesis, treatment of memory loss, treatment of reproduction disorders, treatment of delayed wound healing, treatment of psychosocial deprivation, treatment of pulmonary dysfunction, treatment of ventilator dependency; attenuation of protein catabolic response, reducing cachexia and protein loss, treatment of hyperinsulinemia, adjuvant treatment for ovulation induction, stimulation of thymic development, prevention of thymic function decline, treatment of immunosuppressed patients, improvement in muscle mobility, maintenance of skin thickness, metabolic homeostasis, renal homeostasis, stimulation of osteoblasts, stimulation of bone remodeling, stimulation of cartilage growth, stimulation of the immune system in companion animals, treatment of disorders of aging in companion animals, growth promotion in livestock, and/or stimulation of wool growth in sheep. Other embodiments provide for methods of treatment of inflammatory disorders, including ulcerative colitis, inflammatory bowel disease, Crohn's disease, pancreatitis, rheumatoid arthritis, osteoarthritis, asthma, vasculitis, psoriasis, allergic rhinitis, peptic ulcer disease, postoperative intra-abdominal sepsis, ischemia-reperfusion injury, pancreatic and liver damage, sepsis and septic shock, gastric damage caused by certain drugs, stress-induced gastric damage, gastric damage caused by *H. pylori*, inflammatory pain, chronic kidney disease and intestinal inflammation.

According to a further aspect of the invention, there is provided a method for the treatment of post-operative ileus, cachexia (wasting syndrome), such as that caused by cancer, AIDS, cardiac disease and renal disease, gastroparesis, such as that resulting from type I or type II diabetes, other gastrointestinal disorders, growth hormone deficiency, bone loss, and other age-related disorders in a human or animal patient suffering therefrom, which method comprises administering to said patient an effective amount of at least one member selected from the compounds disclosed herein having the ability to modulate the ghrelin receptor. Other diseases and disorders treated by the compounds disclosed herein include short bowel syndrome, gastrointestinal dumping syndrome, postgastroenterectomy syndrome, celiac disease, and hyperproliferative disorders such as tumors, cancers, and neoplastic disorders, as well as premalignant and non-neoplastic or non-malignant hyperproliferative disorders. In particular, tumors, cancers, and neoplastic tissue that can be treated by the present invention include, but are not limited to, malignant disorders such as breast cancers, osteosarcomas, angiosarcomas, fibrosarcomas and other sarcomas, leukemias, lymphomas, sinus tumors, ovarian, uretal, bladder, prostate and other genitourinary cancers, colon, esophageal and stomach cancers and other gastrointestinal cancers, lung cancers, myelomas, pancreatic cancers, liver cancers, kidney cancers, endocrine cancers, skin cancers and brain or central and peripheral nervous (CNS) system tumors, malignant or benign, including gliomas and neuroblastomas.

In particular embodiments, the macrocyclic compounds of the present invention can be used to treat post-operative ileus. In other embodiments, the compounds of the present invention can be used to treat gastroparesis. In still other embodiments, the compounds of the present invention can be used to treat diabetic gastroparesis. In another embodiment, the compounds of the present invention can be used to treat opioid-induced bowel dysfunction. In further embodiments, the compounds of the present invention can be used to treat chronic intestinal pseudoobstruction.

In particular embodiments of the present invention, the compounds of the present invention can be used to treat postoperative ileus, gastroparesis, opioid-induced bowel dysfunction, chronic intestinal pseudo-obstruction, acute colonic pseudo-obstruction (Ogilvie's syndrome), short bowel syndrome, emesis, constipation-predominant irritable bowel syndrome (IBS), chronic constipation, cancer-associated dyspepsia syndrome, delayed gastric emptying, gastrointestinal dysfunction or delayed gastric emptying in patients with Parkinson's disease, gastrointestinal dysfunction or delayed gastric emptying in myotonic muscular dystrophy, gastrointestinal dysfunction or delayed gastric emptying in patients with scerloderma, gastroesophageal reflux disease (GERD), gastric ulcers, or Crohn's disease.

The present invention further provides methods of treating a horse or canine for a gastrointestinal disorder comprising administering a therapeutically effective amount of a modulator having the structure of formula I, In some embodiments, the gastrointestinal disorder is ileus or colic.

As used herein, "treatment" is not necessarily meant to imply cure or complete abolition of the disorder or symptoms associated therewith.

The compounds of the present invention can further be utilized for the preparation of a medicament for the treatment of a range of medical conditions including, but not limited to, metabolic and/or endocrine disorders, gastrointestinal disorders, cardiovascular disorders, central nervous system disorders, obesity and obesity-associated disorders, genetic disorders, bone disorders, hyperproliferative disorders and inflammatory disorders.

Further embodiments of the present invention will now be described with reference to the following examples. It should be appreciated that these examples are for the purposes of illustrating embodiments of the present invention, and do not limit the scope of the invention.

EXAMPLES

Example 1

Binding Activity

The table below presents binding activity at the human ghrelin receptor for representative compounds of the invention.

| Compound No. | $K_i$ (nM)$^a$ |
| --- | --- |
| 801 | A |
| 802 | C |
| 803 | C |
| 807 | B |
| 808 | C |
| 809 | C |
| 810 | C |

-continued

| Compound No. | K$_i$ (nM)$^a$ |
|---|---|
| 813 | B |
| 816 | B |
| 818 | B |
| 819 | B |
| 820 | C |
| 822 | C |
| 825 | B |
| 826 | C |
| 828 | A |
| 829 | A |
| 831 | A |
| 832 | A |
| 833 | B |
| 851 | C |
| 853 | C |
| 854 | C |
| 855 | C |
| 856 | D |
| 857 | D |
| 858 | D |
| 859 | D |
| 860 | B |
| 862 | B |
| 863 | C |
| 864 | B |
| 865 | C |
| 866 | C |
| 867 | C |
| 869 | C |
| 870 | D |
| 871 | D |
| 872 | B |
| 873 | C |
| 874 | C |
| 876 | C |
| 877 | C |
| 878 | C |
| 923 | C |
| 934a | C |
| 934b | E |
| 935 | C |
| 936 | C |
| 937 | D |
| 938 | C |
| 939 | C |
| 944 | D |
| 945 | D |
| 946 | B |
| 947 | B |
| 950 | D |
| 951 | D |
| 954 | D |
| 965 | D |
| 966 | D |
| 968 | C |
| 969a | C |
| 969b | C |
| 972 | C |
| 973a | C |
| 973b | E |
| 974 | C |
| 975 | C |
| 976 | C |
| 977 | D |
| 978 | C |
| 979 | C |
| 981 | B |
| 982 | A |
| 986 | E |
| 987 | D |
| 988 | C |
| 989 | C |
| 991 | C |
| 992 | C |
| 993 | C |
| 994 | C |

-continued

| Compound No. | K$_i$ (nM)$^a$ |
|---|---|
| 995 | C |
| 996a | B |
| 996b | D |
| 997 | D |
| 998 | C |
| 999a | E |
| 999b | D |
| 1000 | D |
| 1003 | C |
| 1005 | C |
| 1006 | D |
| 1007 | C |
| 1008 | C |
| 1009 | A |
| 1010 | B |
| 1011 | B |
| 1014 | D |
| 1015 | D |
| 1016 | C |
| 1017a | C |
| 1017b | D |
| 1018 | C |
| 1019a | D |
| 1019b | E |
| 1020a | C |
| 1020b | C |
| 1021 | E |
| 1022 | D |
| 1023 | C |
| 1024 | C |
| 1025 | D |
| 1026 | C |
| 1027 | C |
| 1028 | C |
| 1029 | B |
| 1030 | C |
| 1031 | C |
| 1032 | D |
| 1033 | C |
| 1034 | C |
| 1035 | C |
| 1036 | E |
| 1038 | C |
| 1039 | C |
| 1040 | C |
| 1041 | C |
| 1042 | C |
| 1043 | C |
| 1044 | D |
| 1045 | C |
| 1046 | C |
| 1047 | C |
| 1048 | E |
| 1049 | C |
| 1050 | E |
| 1052 | A |
| 1053 | C |
| 1058 | C |
| 1061 | C |
| 1062 | B |
| 1065 | C |
| 1066 | C |
| 1068 | C |
| 1069 | C |
| 1071 | D |
| 1072 | D |
| 1074 | C |
| 1075 | C |
| 1076 | C |
| 1078 | C |
| 1079 | C |
| 1080 | C |
| 1081 | E |
| 1082 | D |
| 1083 | C |
| 1084 | C |

-continued

| Compound No. | $K_i$ (nM)[a] |
|---|---|
| 1085a | C |
| 1085b | C |
| 1086 | C |
| 1087a | D |
| 1087b | C |
| 1088 | D |
| 1089a | C |
| 1089b | D |
| 1090 | D |
| 1098a | D |
| 1098b | C |
| 1099 | A |
| 1100 | B |
| 1101 | D |
| 1103 | E |
| 1104 | C |
| 1105 | A |
| 1106 | C |
| 1107 | C |
| 1108 | A |
| 1109 | B |
| 1110 | C |
| 1111 | C |
| 1112 | A |
| 1113 | A |
| 1114 | A |
| 1115 | D |
| 1116 | C |
| 1118 | B |
| 1119 | C |

[a]Binding activity determined using standard method A, $K_i$ values are expressed as follows: A ≤ 1 nM, B ≤ 10 nM, C ≤ 100 nM, D ≤ 500 nM, E > 500 nM.

Example 2

Functional Activity

The table below presents functional activity at the human ghrelin receptor for representative compounds of the invention.

| Compound | $EC_{50}$ (nM) |
|---|---|
| 807 | A |
| 877 | A |
| 968 | C |
| 969a | C |
| 969b | C |
| 973a | C |
| 973b | C |
| 975 | D |
| 976 | C |
| 982 | A |
| 802 | B |
| 1009 | A |
| 1018 | C |
| 1033 | B |
| 1043 | B |
| 1058 | B |
| 1061 | B |
| 1062 | A |

[b]Functional activity determined using standard method B, $EC_{50}$ values are expressed as follows: A ≤ 50 nM, B ≤ 100 nM, C ≤ 400 nM, D > 400 nM

Example 3

Oral Pharmacokinetics

The table below presents oral bioavailability and elimination half-life data in the rat for representative compounds of the present invention. The parameters were determined by HPLC-MS after oral administration of an 8 mg/kg dose of the compound, except for compound 822 where a 2 mg/kg dose was used.

| Compound | Elimination Half-life ($t_{1/2}$, rat, min) | Oral Bioavailability (rat, % F) |
|---|---|---|
| 801 | 42 | 4 |
| 802 | 160 | 26 |
| 803 | 151 | 9 |
| 807 | 197 | 23 |
| 808 | 238 | 18 |
| 810 | 116 | 15 |
| 813 | 31 | 4 |
| 819 | 116 | 12 |
| 820 | 137 | 18 |
| 822 | 65 | 51 |
| 825 | 101 | 37 |
| 826 | 77 | 29 |
| 829 | 45 | 8 |
| 831 | 120 | 15 |
| 854 | 223 | 22 |
| 862 | 77 | 22 |
| 877 | 255 | 15 |
| 935 | 42 | 11 |
| 968 | 103 | 26 |
| 979 | 34 | 11 |
| 989 | 138 | 7 |
| 999 | 122 | 9 |
| 1011 | 268 | 22 |
| 1027 | 46 | 6 |
| 1061 | 23 | 4 |
| 1069 | 128 | 32 |

In addition, the plasma concentration versus time profiles for representative compounds 802, 807, 810, 819, 822, 825, 831, 854, 877, 968, 1011 and 1069 are provided in FIGS. 3-8.

Example 4

Interaction Profile at Cytochrome P450 Enzyme Subtypes

Inhibition of CYP P450 Isozymes by Representative Compounds of the Invention.

| | $IC_{50}$ (μM) | | | | | | | | | |
|---|---|---|---|---|---|---|---|---|---|---|
| Compound | 3A4 (BQ) | 3A4 (BFC) | 1A2 | 2A6 | 2B6 | 2C8 | 2C9 | 2C19 | 2D6 | 2E1 |
| 803 | 11.5 | — | >100 | >100 | 53.6 | 54.6 | >100 | >100 | >100 | >100 |
| 807 | 6.1 | 23.3 | >100 | >100 | >100 | >100 | >100 | >100 | >100 | >100 |
| 809 | 1.53 | 6.61 | >100 | >100 | >100 | >100 | >100 | >100 | >100 | >100 |
| 810 | 1.08 | 7.42 | 69 | >100 | 102 | >100 | >100 | >100 | >100 | >100 |

-continued

| | IC$_{50}$ (μM) | | | | | | | | | |
|---|---|---|---|---|---|---|---|---|---|---|
| Compound | 3A4 (BQ) | 3A4 (BFC) | 1A2 | 2A6 | 2B6 | 2C8 | 2C9 | 2C19 | 2D6 | 2E1 |
| 816 | 1.36 | 5.85 | >100 | >100 | >100 | >100 | >100 | >100 | >100 | >100 |
| 820 | 13.8 | 47.4 | >100 | >100 | >100 | >100 | >100 | >100 | >100 | >100 |
| 822 | 4.15 | 14.2 | >100 | >100 | >100 | >100 | >100 | >100 | >100 | >100 |
| 825 | 6.7 | 93.4 | >100 | >100 | >100 | >100 | >100 | >100 | >100 | >100 |
| 826 | 4.5 | 47.5 | >100 | >100 | >100 | >100 | >100 | >100 | >100 | >100 |
| 828 | 8.9 | 18.7 | >100 | >100 | >100 | >100 | >100 | >100 | >100 | >100 |

Example 5

Permeability Assays

The table below presents Caco-2 permeability assay data for representative compounds of the present invention.

| Compound | $P_{app}$ A to B cm/sec × $10^{-6}$ | $P_{app}$ B to A cm/sec × $10^{-6}$ | BtoA/AtoB |
|---|---|---|---|
| 801 | 163 | 110 | 0.672 |
| 803 | 12.1 | 67.3 | 5.59 |
| 811 | 125 | 198 | 1.59 |
| 825 | 113 | 123 | 1.08 |
| 826 | 11.2 | 46.9 | 4.18 |

Example 6

Protein Binding

The table below presents protein binding data for representative compounds of the present invention in both human and rat plasma.

| Compound | Test Concentration (μg/mL) | Human Plasma Protein Binding (%) | Rat Plasma Protein Binding (%) |
|---|---|---|---|
| 801 | 3 | 88.4 | nd |
| 802 | 1 | 93.4 | 99.8 |
| 803 | 1 | 97.8 | 99.1 |
| 807 | 5 | 99.3 | 84.0 |
| 808 | 5 | 99.9 | 89.2 |
| 809 | 3 | 88.4 | 92.8 |
| 810 | 3 | 78.9 | nd |
| 819 | 3 | 95.2 | 98.2 |
| 820 | 3 | 99.0 | 98.8 |
| 822 | 3 | 93.0 | 99.1 |
| 825 | 1 | 83 | 96.6 |
| 825 | 5 | 70 | 73 |
| 826 | 3 | 94.3 | 97.2 |
| 828 | 3 | 76.8 | nd |
| 829 | 3 | 91.6 | nd |
| 832 | 3 | 88.9 | 97.3 |
| 833 | 3 | 77.4 | 94.0 |
| 1118 | 3 | 92.8 | 95.5 | nd = not determined

Example 7

Gastric Emptying Model

The effects of representative compounds of the invention in the rat gastric emptying model described in standard method E are provided in the following table. In cases where an experiment was conducted multiple times, the average of the individual results is presented.

Percent Increase in Gastric Emptying after Oral Administration

| | Dose (mg/kg) | | | |
|---|---|---|---|---|
| Compound | 1 | 3 | 10 | 30 |
| 801 | — | 27 | 31 | 40 |
| 802 | 12 | 11 | 26 | — |
| 807 | 17 | 31 | 41 | — |
| 808 | 18 | 37 | 40 | — |
| 809 | — | 5 | — | — |
| 813 | — | 11 | — | — |
| 818 | — | 11 | — | — |
| 819 | 9 | 21 | 18 | — |
| 820 | 6 | 20 | 22 | — |
| 822 | — | 6 | — | — |
| 826 | 19 | 12 | 30 | — |
| 828 | — | 24 | — | — |
| 829 | — | 28 | — | — |
| 831 | — | 32 | — | — |
| 832 | — | 13 | — | — |
| 833 | — | 6 | — | — |
| metoclopramide | — | — | — | 35 |

— indicates not determined

With the relatively long half-lives exhibited by some of these compounds as shown in Example 3, it could be expected that their effects on gastric emptying could be prolonged. Indeed, this was confirmed for compound 807, where gastric emptying rates remained increased (18-23%) up to 24 h post-dose.

Also of note is the effectiveness of compound 801 at promoting gastric emptying even though its oral bioavailability was only 4% (Example 3). This suggests that the compound and certain others of the invention possess pro-motility activity locally in the GI system, while limiting systemic exposure. Such a characteristic could lead to reduced side effects in their use as a pharmaceutical agent.

Example 8

Post-Operative Ileus

Effect of Representative Compound in the Treatment of Post-operative Ileus in Rat.

Methods
1. Model adapted from Kälff et al. (1998), Ann Surg 228:652-63.
2. Rats (male, Sprague-Dawley, 250-300 g) are implanted with jugular vein catheters to accommodate dosing of test articles.
3. Rats are fasted O/N, anesthetized with isofluorane and subjected to abdominal surgery.
4. Following an abdominal incision, the small intestine caecum and large intestine are eviscerated for a period of 15 min and kept moist with saline.

5. A "running of the bowel" is performed, a clinically-relevant manipulation of the intestines characterized by first pinching the upper small intestine and continuing this manipulation down through the large intestine.
6. Rats are allowed a 15 min recovery beginning after the disappearance of any effects of the isofluorane anesthesia.
7. Rats are dosed with vehicle or test compound at appropriate dose levels (for example 30, 100, or 300 μg/kg, i.v., N=6/gp) followed by intragastric gavage of $^{99m}$Tc methylcellulose (2%) meal.
8. After 15 min, the rats are euthanized and the stomach and consecutive 10 cm segments of the intestine are isolated. Radioactivity ($^{99m}$Tc) in each tissue isolate is measured as a means of measuring the transit of the meal.

Example 9

Opioid-Delayed Gastric Emptying

Effect of Representative Compound on Gastric Emptying and Gastrointestinal Transit in a Model of Opioid-Delayed Gastric Emptying.

Opioid analgesics, such as morphine, are well known to delay gastrointestinal transit which is an important side-effect for this class of drugs. The clinical term for this syndrome is opioid bowel dysfunction (OBD). Importantly, patients recovering from abdominal surgery experience post-operative ileus that is further exacerbated by concomitant opioid therapy for post-surgical pain. The objective of this procedure is to determine whether compounds of the invention may have therapeutic utility in the treatment of OBD.

Methods
1. Rats (male, Sprague-Dawley, 250-300 g) are implanted with jugular vein catheters to accommodate dosing of test articles.
2. Overnight-fasted rats are administered morphine (3 mg/kg s.c.).
3. After 30 min, rats are to be dosed with vehicle or test compound at appropriate dose levels (for example 300 or 1000 μg/kg, i.v., n=4-to-6/gp) followed by intragastric gavage of $^{99m}$Tc methylcellulose (2%) meal.
4. After 15 min, the rats are euthanized and the stomach and consecutive 10 cm segments of the intestine are isolated. Radioactivity ($^{99m}$Tc) in each tissue isolate is measured as a means of measuring the transit of the meal.

Example 10

Gastroparesis Animal Model

High caloric meals are well known to impede gastric emptying. This observation has recently been exploited by Megens, A.A.; et al. (unpublished) to develop a rat model for delayed gastric emptying as experienced in gastroparesis.

Materials
1. Wistar rats, male, 200-250 g
2. Chocolate test meal: 2 mL Clinutren ISO® (1.0 kcal/mL, Nestle SA, Vevey Switzerland)

Method

The test meal is given to the subjects by oral gavage at time=0. After 60 min, the subjects are sacrificed, the stomachs excised and the contents weighed.

Test compounds are administered intravenously as aqueous solutions, or solutions in normal saline, at time=0 at three dose levels (0.08 mg/kg; 0.30-0.31 mg/kg, 1.25 mg/kg). When necessary, cyclodextrin (CD) was added to solubilize the material. Test compounds to be examined utilizing subcutaneous injection are administered at time=−30 min. Four to five (4-5) rats were tested per group, except in the case of the cyclodextrin control in which ten (10) rats comprise the group.

Results are to be reported as percentage relative to the stomach weight for injection only of solvent as a control to illustrate the gastric emptying capability of the compounds of the present invention.

Example 11

Synthesis of Tethers

A. Standard Procedure for the Synthesis of Tether T85

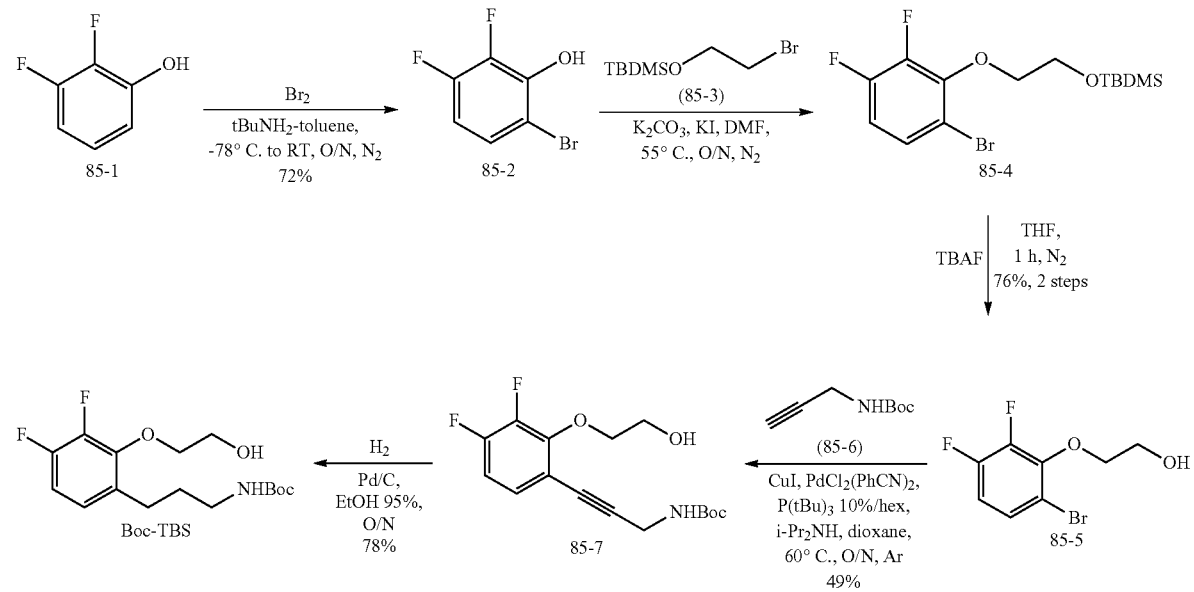

The tether Boc-T85 was constructed starting from 2,3-difluorophenol (85-1, 20 g, 154 mmol) in 21% overall yield for 5 steps.

TLC: $R_f$: 0.13 (25/75 AcOEt/Hex), detection: UV, ninhydrin $^1$H NMR (CDCl$_3$): δ 6.84 (m, 2H), 4.19 (m, 2H), 3.97 (m, 2H), 3.08 (m, 2H), 2.95 (m, 2H), 2.16 (s, 1H), 1.74 (m, 2H), 1.44 (m, 9H)

LC-MS (Grad A4) $t_R$: 6.31 min

B. Standard Procedure for the Synthesis of Tether T86

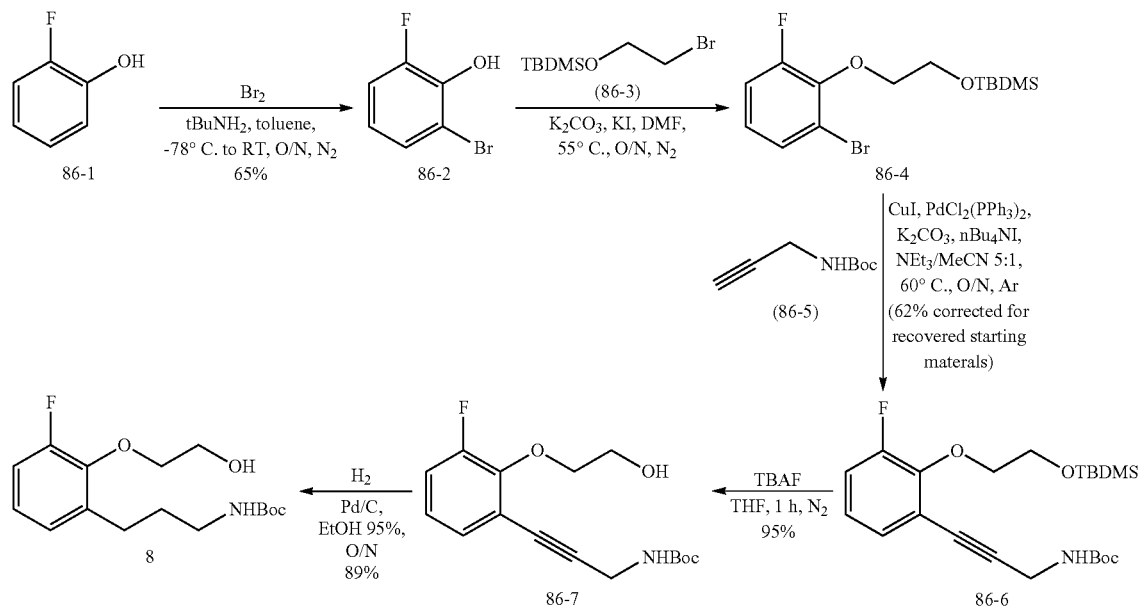

Starting from 2-fluorophenol (86-1, 33.8 g, 302 mmol), Boc-T86 was prepared utilizing the five step process shown in 26% yield (corrected for recovered starting materials in step 3).

TLC: $R_f$: 0.33 (50/50 AcOEt/Hex), detection: UV, ninhydrin $^1$H NMR (CDCl$_3$): δ 6.94 (m, 2H), 5.09 (m, 1H), 4.15 (m, 2H), 3.94 (m, 2H), 3.08 (m, 2H), 2.70 (m, 2H), 1.78 (m, 1H), 1.61 (m, 2H), 1.44 (s, 9H)

LC-MS (Grad A4) $t_R$: 6.81 min

C. Standard Procedure for the Synthesis of Tether T87

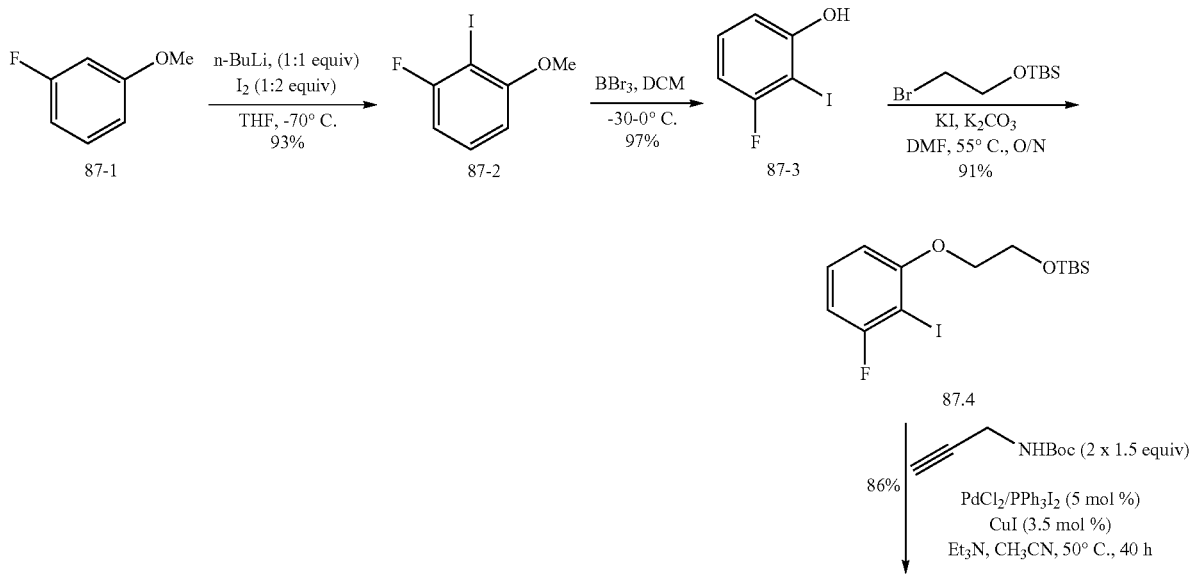

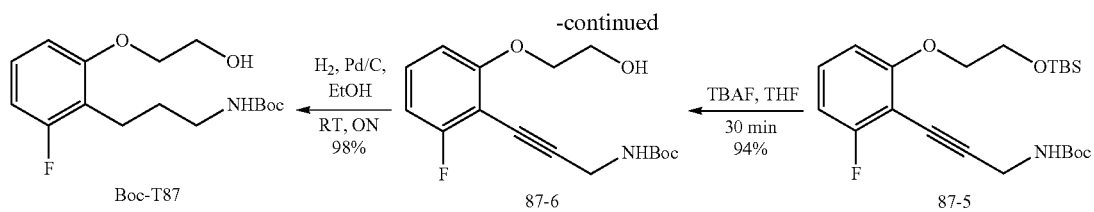

Boc-T87 was synthesized from 3-fluoro-2-iodoanisole (87-2, 23.4 g, 92.7 mmol, Grunewald, O. L. et. al. *J. Med. Chem.* 1986, 29, 1972-1982), using the sequence of reactions presented in 65% overall yield.

TLC, $R_f$=0.3 (AcOEt/hexanes, 1/1)

D. Standard Procedure for the Synthesis of Tether T100

Step T100-1. 3-Bromo-2-hydroxy-benzaldehyde 100-1: To a stirred suspension of 2-bromophenol (100-0, 3.5 g, 20 mmol) and paraformaldehyde (8.1 g, 270 mmol) in 100 mL of dry acetonitrile at room temperature was added $MgCl_2$ (2.85 g, 30 mmol) and triethylamine (10.45 mL, 75 mmol). The reaction was stirred vigorously at reflux

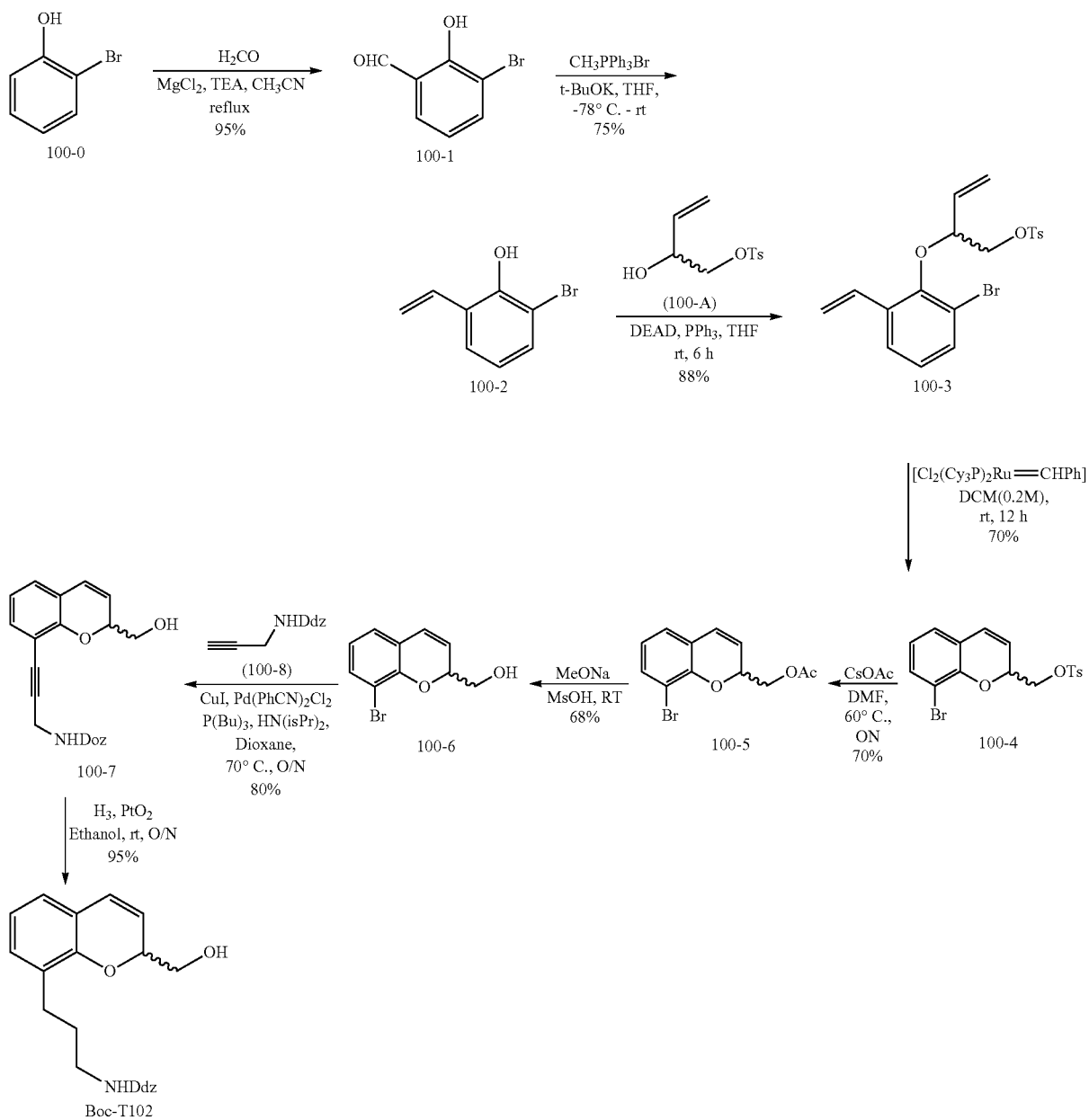

overnight. The mixture was cooled down to room temperature, then 30 mL of 5% HCl added and the product extracted with Et₂O to give 4 g (95%) of 100-1.

Step T100-2. 2-Bromo-6-vinyl-phenol 2: To a stirred solution of CH₃PPh₃Br (72 g, 0.033 mol) at room temperature was added, over 5 min, tBuOK (4.1 g, 0.03 mol) in THF (50 mL). The mixture was cooled to −78° C. and 100-1 (3 g, 0.015 mol) added dropwise over 15 min. The reaction mixture was stirred at room temperature for 24 h, After this time, the solvent was removed in vacuo and the residue purified by flash column chromatography using Et₂O as an eluent to afford 100-2 as a colorless oil (2.2 g, 75%).

Step T100-3. Toluene-4-sulfonic acid 2-(2-bromo-6-vinyl-phenoxy)-but-3-enyl ester 3. To a solution of 110-2 (2.5 g, 12 mmol), Ph₃P (4.6 g, 18 mmol) and toluene-4-sulfonic acid 2-hydroxy-but-3-enyl ester (100-A, 4.3 g, 18 mmol) in 150 mL of THF was slowly added diethyl azodicarboxylate (3.5 mL, 18 mmol) at room temperature. The mixture was stirred at room temperature for 6 h until complete as evidenced by TLC. The solvent was removed under high vacuum and the residue purified by flash column chromatography to obtain 100-3 as a pale brown liquid (4.6 g, 68%).

Step T100-4. Toluene-4-sulfonic acid 8-bromo-2H-chromen-2-ylmethyl ester 4, 100-3 (3.4 g, 8 mmol) was treated with 2$^{nd}$ generation Grubbs catalyst (0.02%) in 50 mL of DCM. The mixture was stirred at room temperature for 6 h until complete by TLC analysis. The solvent was removed under high vacuum and the residue purified by flash column chromatography to obtain 100-4 as a pale brown liquid (2.15 g, 70%).

Step T100-5. Acetic acid 8-bromo-2H-chromen-2-ylmethyl ester 5. To a solution of 100-4 (1.43 g, 23 mmol) in dry DMF (50 mL) was added cesium acetate (2.09 g, 10.9 mmol) under argon. The solution was stirred at 50° C. for 12 h. After this time, the solvent was removed under high vacuum and the residue purified by flash column chromatography to obtain 100-5 as a pale brown liquid (0.7 g, 70%).

Step T100-6. (8-Bromo-2H-chromen-2-yl)-methanol 6. To a solution of 100-5 (5.5 g, 23 mmol) in dry MeOH (150 mL) was added sodium metal in a catalytic amount under argon. The solution was stirred at room temperature for 30 min. After this time, Amberlite IRA-120 (H⁺) resin was added and the mixture vigorously stirred for 10 min. The resin was removed by filtration and the solvent evaporated. Pure compound 100-6 was recovered as a colorless oil (4.5 g, 90%).

Step T100-7. [3-(2-Hydroxymethyl-2H-chromen-8-yl)-prop-2-ynyl]-carbamic acid 3,5-dimethoxybenzyl ester 7, 100-6 (4.5 g, 18 mmol) and Ddz-propargylamine (100-B, 15.2 g, 55.8 mmol) were dissolved in dioxane (150 mL) and diisopropylamine (27 mL) and the reaction mixture degassed by bubbling argon through the solution. PdCl₂(PhCN)₂ (430 mg, 1.11 mmol, 0.06 eq), CuI (220 mg, 1.11 mmol, 0.06 eq), and tributylphosphine 10% in hexane (4.4 mL, 2.23 mmol) were added and the mixture warmed to 70° C. and stirred overnight. The solvent was removed under high vacuum and the residue purified by flash column chromatography to obtain 100-7 as a pale brown liquid (3.2 g, 80%)

Step T100-8. [3-(2-Hydroxymethyl-chroman-8-yl)-propyl]-carbamic acid 3,5-dimethoxybenzyl ester 8. 100-7 (4.5 g, 0.2 mol) was dissolved in EtOH (150 mL) and the solution purged with nitrogen for 10 min. PtO₂ (10 mol %, 450 mg) was then added, and the mixture charged into a Parr apparatus flushed with hydrogen (simply fill with hydrogen at 60 psi and release under vacuum, then refill, repeat this fill—release—refill cycle three times), and reacted with hydrogen at 60 psi at room temperature overnight. The reaction mixture was filtered over a pad of Celite® (use methanol for washing the residue) and the filtrate concentrated to afford a practically pure (by NMR), but colored, sample of Ddz-T100 in a quantitative yield. Further purification can be achieved by subjecting this material to flash chromatography. Note that the product has the same $R_f$ as the starting material and hence, NMR is required to differentiate them.

¹H NMR (300 MHz, CDCl₃): δ 6.82-6.98 (m, 2H); 6.80-6.75 (m, 1H); 6.53 (s, 2H); 6.35 (t, 1H, 2 Hz); 5.23 (b, 1H); 4.08 (m, 1H); 3.90-3.68 (m, 8H); 3.20-2.97 (m, 2H); 2.95-53 (m, 4H); 2.0-1.63 (m, 10H).

¹³C NMR (75.5 MHz, CDCl₃): δ ☐160.85; 155.56; 152.55; 149.56; 128.13; 127.77; 120.28; 103.22; 98.43; 80.72; 76.80; 65.76; 55.46; 40.23; 30.45; 29.34; 29.22; 27.10; 24.97; 23.94.

E. Standard Procedure for the Synthesis of Tethers T100a and T100b

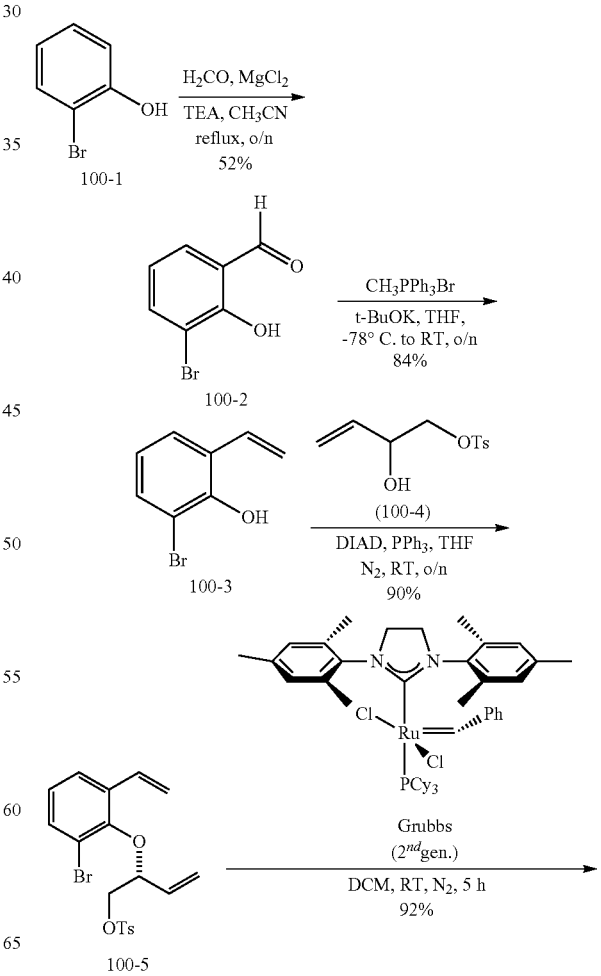

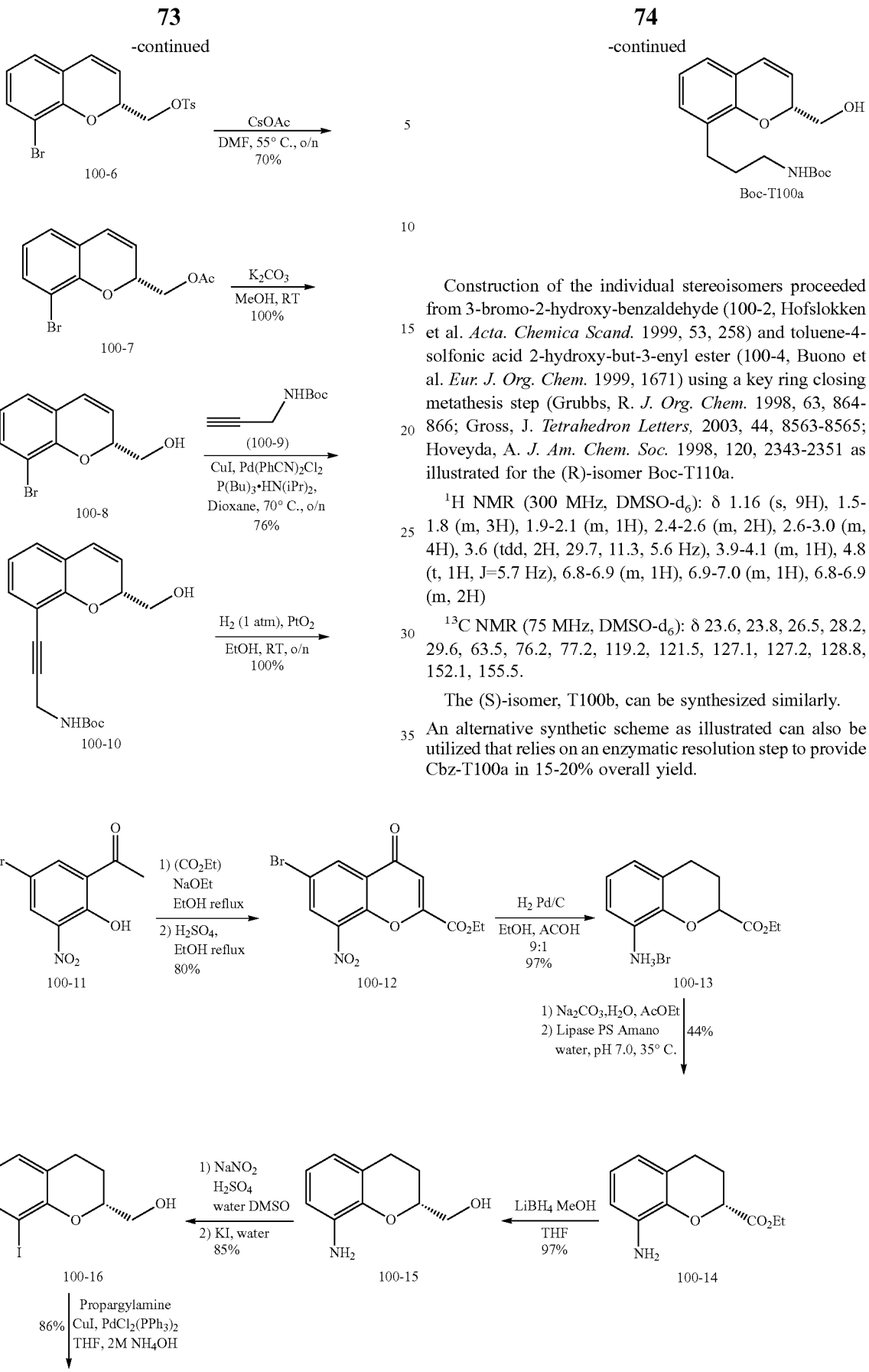

Construction of the individual stereoisomers proceeded from 3-bromo-2-hydroxy-benzaldehyde (100-2, Hofslokken et al. *Acta. Chemica Scand.* 1999, 53, 258) and toluene-4-solfonic acid 2-hydroxy-but-3-enyl ester (100-4, Buono et al. *Eur. J. Org. Chem.* 1999, 1671) using a key ring closing metathesis step (Grubbs, R. *J. Org. Chem.* 1998, 63, 864-866; Gross, J. *Tetrahedron Letters*, 2003, 44, 8563-8565; Hoveyda, A. *J. Am. Chem. Soc.* 1998, 120, 2343-2351 as illustrated for the (R)-isomer Boc-T110a.

$^1$H NMR (300 MHz, DMSO-$d_6$): δ 1.16 (s, 9H), 1.5-1.8 (m, 3H), 1.9-2.1 (m, 1H), 2.4-2.6 (m, 2H), 2.6-3.0 (m, 4H), 3.6 (tdd, 2H, 29.7, 11.3, 5.6 Hz), 3.9-4.1 (m, 1H), 4.8 (t, 1H, J=5.7 Hz), 6.8-6.9 (m, 1H), 6.9-7.0 (m, 1H), 6.8-6.9 (m, 2H)

$^{13}$C NMR (75 MHz, DMSO-$d_6$): δ 23.6, 23.8, 26.5, 28.2, 29.6, 63.5, 76.2, 77.2, 119.2, 121.5, 127.1, 127.2, 128.8, 152.1, 155.5.

The (S)-isomer, T100b, can be synthesized similarly.

An alternative synthetic scheme as illustrated can also be utilized that relies on an enzymatic resolution step to provide Cbz-T100a in 15-20% overall yield.

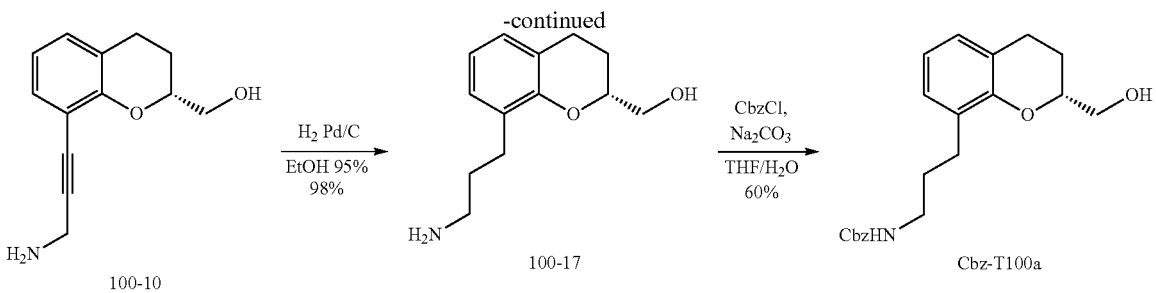

F. Standard Procedure for the Synthesis of Tether T101

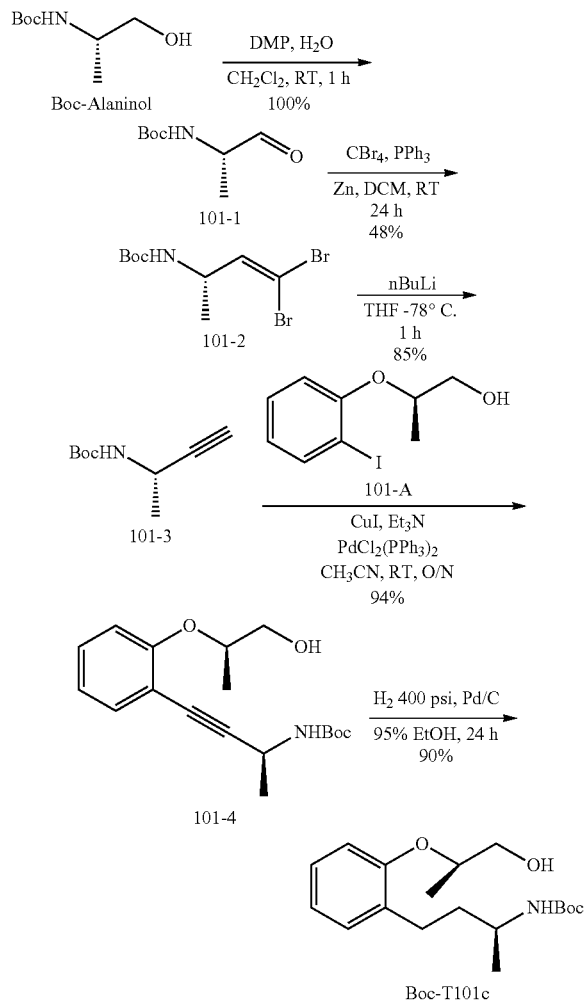

Step T101-1: Synthesis of aldehyde 101-1 (Meyer, S. D. and S. L. Schreiber *J. Org. Chem* 1994, 59, 7549-7552): To a solution of Boc-alaninol (29.5 g, 168 mmol, 1.0 eq) in DCM (1 L) was added Dess-Martin periodinane (100 g, 236 mmol, 1.4 eq). IBX and pyr-SO₃ can alternatively be used for the oxidation. H₂O (4.25 mL, 1.4 eq) was added with a dropping funnel over 0.5 hour with vigorous stirring. Et₂O was added and the solution filtered, then concentrated by rotary evaporator. The residue was dissolved in Et₂O and the solution was washed sequentially with saturated NaHCO₃: 10% sodium thiosulfate (1:1), water, brine. Extra washes with the first mixture are sometimes needed to remove the acetic acid formed by the DMP reagent. The combined aqueous phases were back-extracted once with Et₂O and the combined organic phases dried with MgSO₄, filtered and concentrated by rotary evaporator to afford 29 g (100%) of 101-1 as a white solid that was gently azeotroped with toluene(3×). This material was typically used immediately after preparation.

TLC: $R_f$=0.3 (hexane/EtOAc, 1/4)

¹H NMR (CDCl₃, 300 MHz): δ 9.56 (s, 1H), 5.07 (br s, 1H) 4.29-4.17 (m, 1H), 1.45 (s, 9H), 1.34 (d, 3H, J=7.4 Hz).

Step T101-2: Synthesis of dibromide 101-2: To activated [washed with 0.5 N HCl. (3×), H₂O (3×), MeOH (3×), Et₂O (3×) and dried under vacuum pump] Zn powder (20.9 g, 320 mmol, 2.0 eq) and CBr₄ (106 g, 320 mmol, 2.0 eq) in DCM (1 L) at 0° C. was added, in three portions over 5 min to control the exothermic reaction, PPh₃ (83.9 g, 320 mmol, 2.0 eq). The solution was stirred at room temperature for 24 h during which time the color turns from yellow to pink. Freshly prepared 101-1 (27.7 g, 160 mmol, 1.0 eq) was added in DCM (100 mL). The solution turns to dark violet over the next 24 h. The solution was concentrated by rotary evaporator and then purified by flash column chromatography on silica gel (hexane/EtOAc, 10/1) to afford 25.5 g (48%) of 101-2 as white solid.

TLC: $R_f$=0.67 (EtOAc/Hexanes, 3/7)

¹H NMR (CDCl₃, 300 MHz): δ 6.34 (d, 1H, J=8.2 Hz), 4.53 (br s, 1H), 4.341-4.27 (m, 1H), 1.45 (s, 9H), 1.24 (d, 3H, J=6.8 Hz).

Step T101-3: Synthesis of alkyne 101-3: To a solution of 101-2 (25.5 g, 77.5 mmol, 1.0 eq) in dry THF (1.2 L) at −78° C. was added dropwise a freshly titrated solution of n-BuLi in hexanes (2.0 M, 116 mL, 232.5 mmol, 3.0 eq). The solution was stirred at −78° C. for 1.0 h. A solution of 0.01 N NaOH (300 mL) was then added and the mixture warmed to room temperature. The aqueous phase was extracted with Et₂O (2×300 mL). The combined organic phases were washed with brine (2×300 mL), dried over MgSO₄, concentrated by rotary evaporator, then purified by flash column chromatography on silica gel (hexanes/EtOAc, 4/1) to afford 11.1 g (85%) of 101-3 as a white solid.

TLC: $R_f$=0.57 (Et₂O/Hexane, 2/3)

¹H NMR (CDCl₃, 300 MHz): δ 4.68 (br s, 1H), 4.55-4.41 (m, 1H), 2.24 (d, 1H, J=2.3 Hz), 1.45 (s, 9H), 1.40 (d, 3H, J=6.9 Hz).

Step T101-4: Synthesis of alkyne 101-4: To a solution of 101-3 (10.0 g, 62.1 mmol, 1.0 eq) and iodo-alcohol [101-A, 22.5 g, 80.7 mmol, 1.3 eq, prepared as previously described for T33 (WO 2004/111077; WO 2005/012331; WO 2006/009674)] in CH₃CN (460 mL) was bubbled argon for 20 min. Freshly distilled Et₃N (refluxed for 4 h on CaH₂ then distilled, 31 mL, 224 mmol, 3.6 eq) was added and argon was bubbled for 10 min. Recrystallized CuI (355 ng, 1.9 mmol, 0.03 eq) and PdCl₂(PPh₃)₂ (1.33 g, 1.9 mmol, 0.03 eq) were then added. The reaction was stirred under argon atmosphere overnight at room temperature with TLC monitoring. The volatiles were removed by rotary evaporator and the residue purified by flash column chromatography on silica gel (DCM/EtOAc, 4/1) to afford 18.6 g (94%) of 101-4 as an orange solid. TLC: $R_f$=0.13 (Et₂O/Hexane, 1/4)

¹H NMR (CDCl₃, 300 MHz): δ 7.37 (dd, 1H, J=1.8, 7.8 Hz), 7.28-7.23 (m, 1H), 6.94 (dtd, 2H, J=1.1, 3.5, 4.6 Hz), 4.87 (br s, 1H), 4.78-465 (m, 1H), 4.52-4.41 (m, 1H), 3.74 (dd, 2H, J=2.2, 5.0 Hz), 1.49 (d, 3H, J=6.8 Hz), 1.46 (s, 9H), 1.32 (d, 3H, J=6.2 Hz)

The corresponding (2R,9R)-stereoisomer of 101-4 is prepared analogously starting from Boc-D-alaninol in similar yields.

¹H NMR (CDCl₃, 300 MHz): δ 7.37 (dd, 1H, J=1.7, 7.8 Hz), 7.26 (dd, 1H, J=1.7, 15.8 Hz), 6.98-6.92 (m, 2H), 4.98 (br s, 1H), 4.79-4.64 (m, 1H), 4.47 (d p, 1H, J=3.5, 6.3 Hz), 3.73 (dq, 2H, J=5.0, 11.8 Hz), 1.48 (d, 3H, J=6.9 Hz), 1.46 (s, 9H), 1.31 (d, 3H, J=6.2 Hz)

Step T101-5: Hydrogenation: To alkyne 101-4 (1.87 g, 5.86 mmol, 1.0 eq) was added 10% Pd/C (280 mg, 15% by weight) and 95% EtOH (150 mL). The mixture was placed in a hydrogenation apparatus (Parr for example) under a pressure of 400 psi of hydrogen for 24 h. Monitoring can be performed by LC-MS. The mixture was filtered through a Celite® pad, then concentrated by rotary evaporator to afford 1.7 g (90%) of Boc-T101c as a colorless oil.

¹H NMR (CDCl₃, 300 MHz): δ 7.18-7.10 (m, 2H), 6.90-6.82 (m, 2H), 4.58-4.46 (m, 2H), 3.79 (d, 2H, J=5.2 Hz), 3.74-3.60 (m, 1H), 2.61 (dtd, 2H, J=5.4, 12.9, 23,5 Hz), 1.92-1.85 (m, 2H), 1.44 (s, 9H), 1.26 (d, 3H, J=6.2 Hz), 1.16 (d, 3H, J=6.5 Hz)

LC-MS (Grad B4) $t_R$: 12.62 min

Boc-T101a is prepared similarly from the (2R,9R)-isomer of 101-4.

¹H NMR (CDCl₃, 300 MHz): δ 7.19-7.11 (m, 2H), 6.91-6.84 (m, 2H), 4.58-4.48 (m, 2H), 3.87-3.79 (m, 1H), 3.74 (dd, 1H, J=6.3, 11.8 Hz), 3.69-3.55 (m, 1H), 2.64 (t, 2H, J=7.4 Hz), 1.85-1.61 (m, 2H), 1.45 (s, 9H), 1.29 (d, 3H, J=6.2 Hz), 1.15 (d, 3H, J=6.6 Hz).

LC-MS (Grad B4) $t_R$: 12.57 min

Analogous syntheses starting from one or both of the enantiomeric starting materials, Boc-D-alaninol and the Boc-(R)-methylpropargylamine (101-3), can be applied to provide the other possible stereoisomers.

G. Standard Procedure for the Synthesis of Tether T102

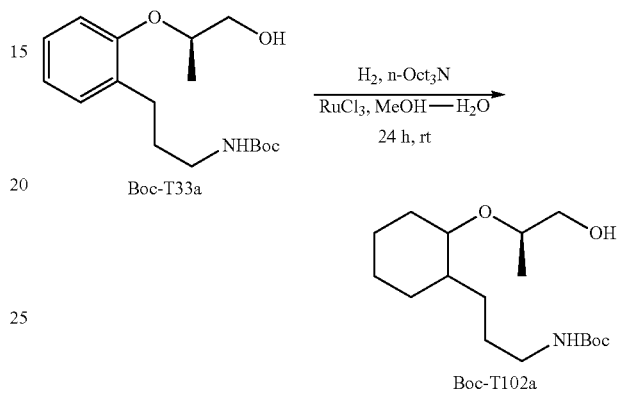

Precursor Boc-T33a is obtained as previously described (WO 2004/111077; WO 2005/012331). Boc-T33a (39 mmol), trioctylamine (1.2 mL, 3.28 mmol) and RuCl₃ (0.936 mmol, 195 mg) were dissolved in 59 mL MeOH—H₂O (70:30, v/v) and stirred under 750 psi H₂ for 24 h at room temperature. The mixture was filtered, then concentrated under reduced pressure. The residue was purified by flash column chromatography (3/7, AcOEt/Hexanes) to provide Boc-T102a in 80-90% yield. Boc-T102b can be synthesized analogously from Boc-T33b.

LC-MS (Grad B4) $t_R$: 7.62 and 8.12 min (diasteroemeric mixture around ring C atoms); MS: 315

H. Standard Procedure for the Synthesis of Tether T103

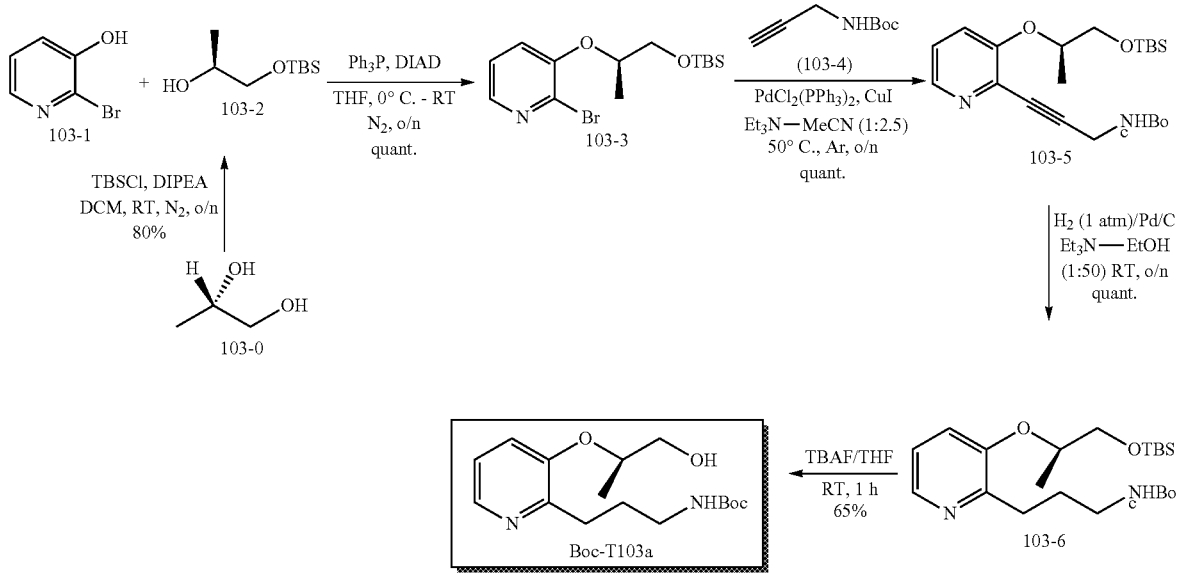

The four (4) step reaction sequence starting from 103-1 and 103-2 (prepared as shown from S-(+)-1,2-propanediol (103-0)) provided Boc-T103a in a very good overall yield of 85%. The alternatively protected analogue Ddz-T103a was prepared using the same procedure with an overall yield of 55% [1.4 g Ddz(2RMe)opy18 was obtained starting from 1 g (5.8 mmol) of 103-1]. Synthesis of the Boc-T103b stereoisomer proceeds similarly, but starting from R-(−)-1,2-propanediol.

TLC: $R_f$: 0.3 (100% EtOAc)

I. Standard Procedure for the Synthesis of Tether T104

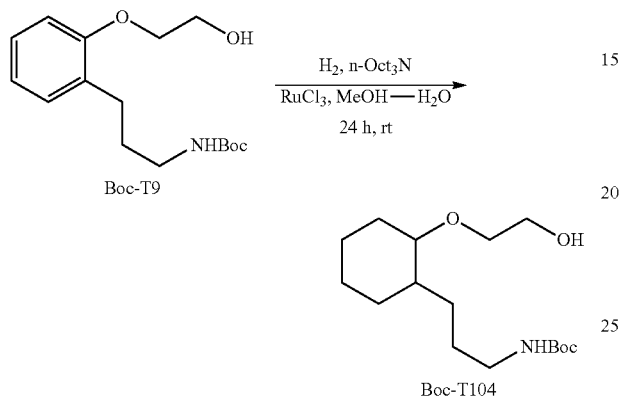

This tether was prepared in 80-90% yield from Boc-T9 in a manner analogous to that already described for Boc-T102.

J. Standard Procedure for the Synthesis of Tether T105

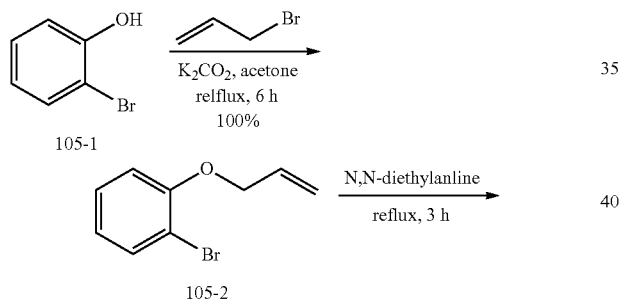

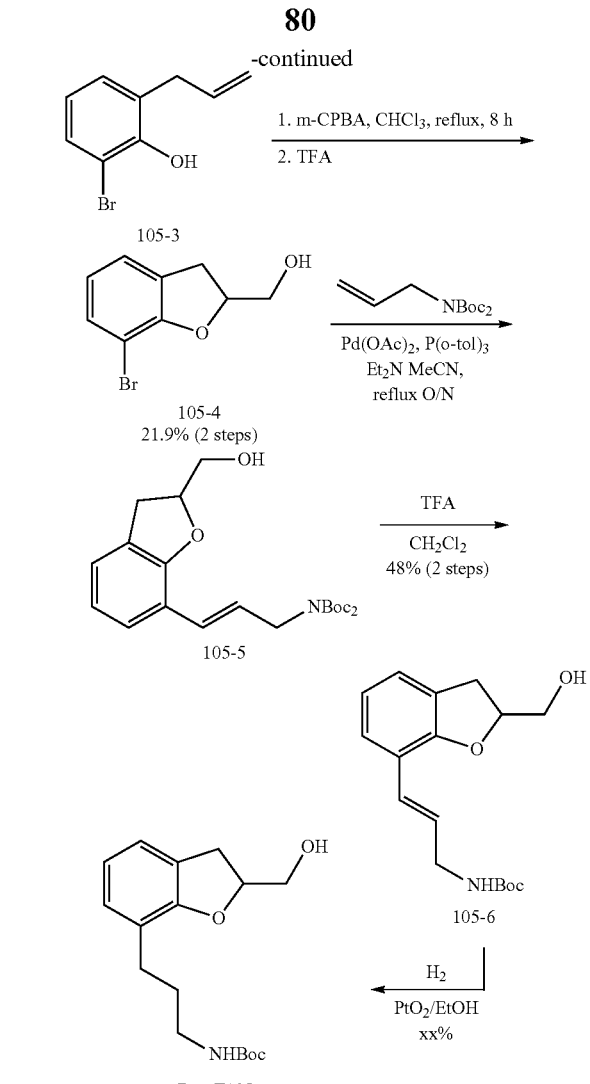

Construction of Boc-T105 was accomplished in ~10% overall yield starting from 2-bromophenol (105-1, 45 g, 260 mmol).

K. Standard Procedure for the Synthesis of Tether T108

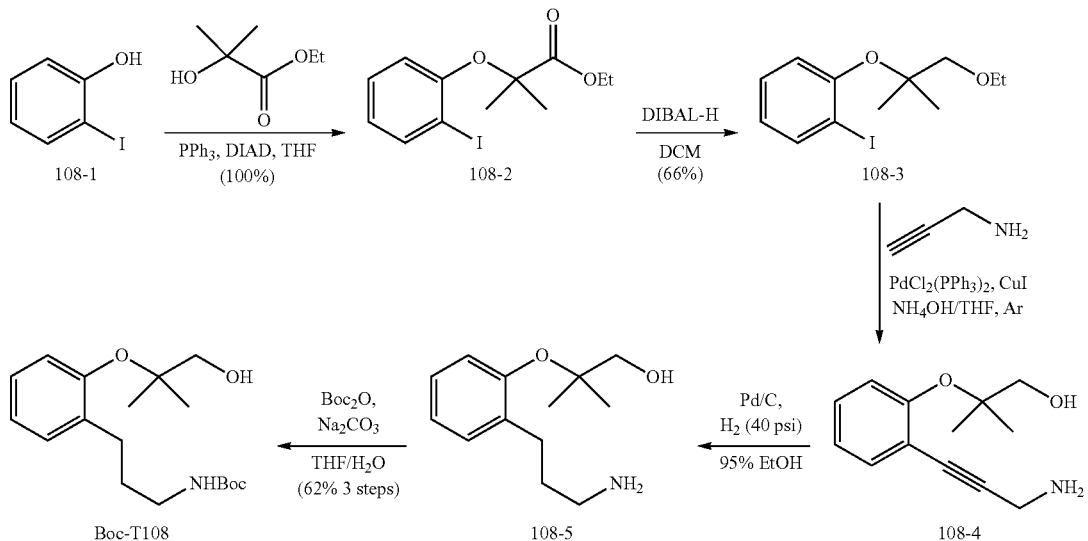

Beginning from 2-iodophenol (108-1, 10.0 g, 45.5 mmol, 1.0 eq.), Boc-T108 was prepared in 53% overall yield for the five (5) step procedure illustrated.

TLC: R$_f$=0.47 (Hex/EtOAc (1:1)), detection: UV+Mo/Ce $^1$H NMR (CDCl$_3$): δ 7.16-6.98, (m, 4H), 5.40-5.08 (bs, 1H), 3.68 (s, 2H), 3.04-2.92 (t, 2H), 2.73-2.68 (t, 2H), 2.46-2.16 (bs, 1H), 1.78-1.69 (q, 2H), 1.45 (s, 9H), 1.31 (s, 6H)

L. Standard Procedure for the Synthesis of Tether T109

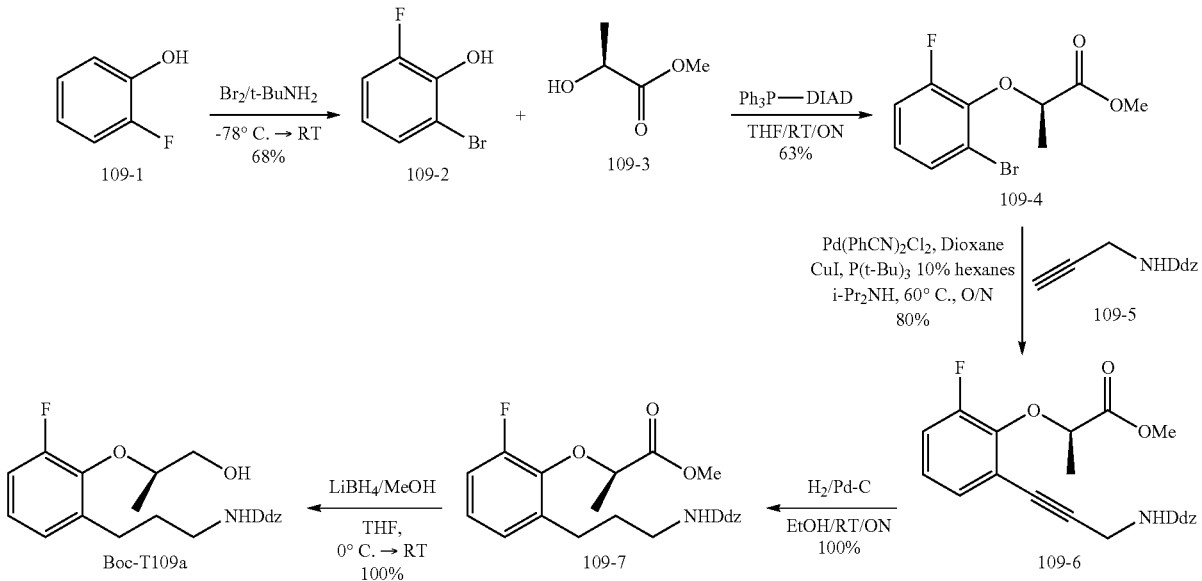

This tether required a five (5) step procedure in order to prepare Ddz-T109 in an overall yield of 34% starting from 2-fluorophenol (109-1, 11.2 g, 100 mmol). The corresponding (S)-isomer, Boc-T109b, can be constructed analogously, but using (R)-methyl lactate in place of (S)-methyl lactate (109-3) in the second step.

TLC: R$_f$: 0.25 [Et$_2$O:hexane, (1:1)]

Boc-T109 was synthesized similarly in an overall yield of 15-25%.

$^1$H NMR (CDCl$_3$, 300 MHz): δ 6.94 (m, 3 H), 4.45 (m, 1 H), 3.85 (dd, J=12, 3.2, 1 H), 3.72 (m, 1 H), 3.05 (m, 2 H), 2.72 (m, 2 H), 2.52 (s, br, 1 H), 1.76 (m, 2 H), 1.45 (s, 9 H), 1.24 (dd, J=6.5, 1.1, 3 H).

$^{13}$C NMR (CDCl$_3$, 75 MHz): δ 136.97, 125.26, 125.22, 123.81, 123.70, 122.78, 114.62, 114.36, 79.82, 79.75, 66.31, 39.55, 30.58, 28.41, 26.66, 16.08.

MS: 328 (M+H)$^+$

M. Standard Procedure for the Synthesis of Tether T110

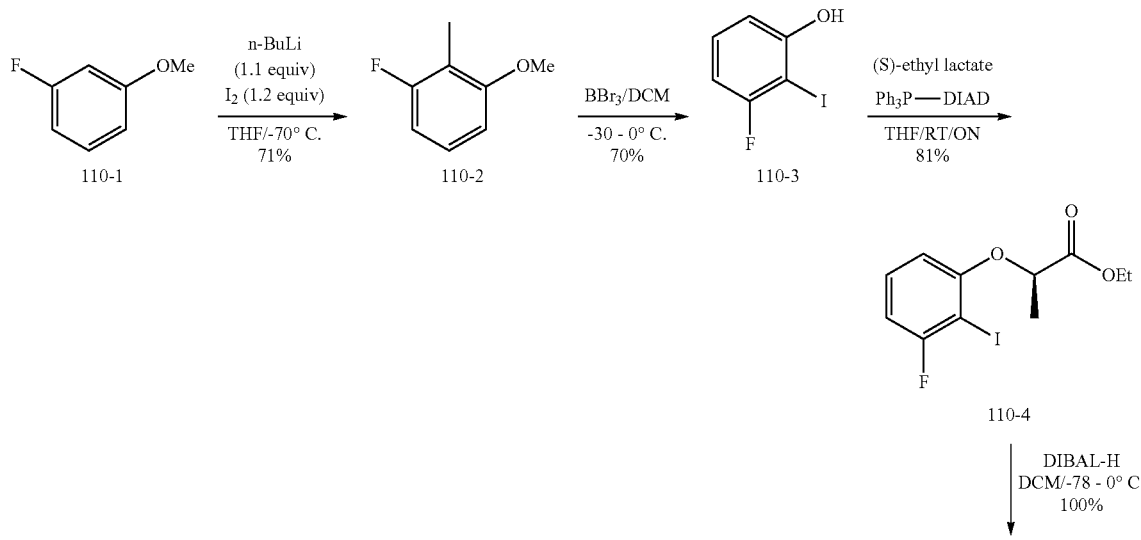

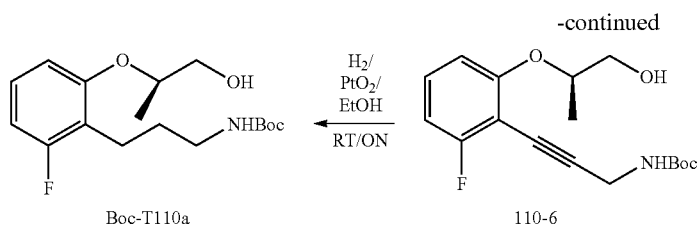
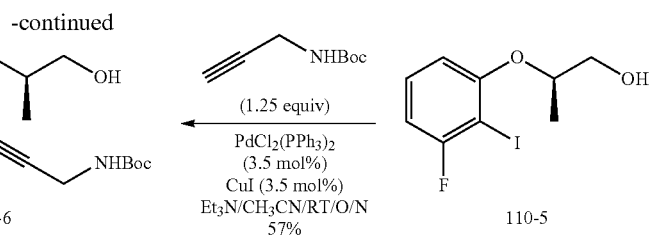

Boc-T110a was synthesized from 3-fluoroanisole (110-1, 12.6 g, 100 mmol) in six (6) steps in an overall yield of 19%.

$^1$H NMR (CDCl$_3$, 300 MHz): δ 7.09 (m, 1 H), 6.65 (m, 2 H), 4.54 (m, 1 H), 3.79 (m, 2 H), 3.13 (m, 2 H), 2.98 (s, br, 1 H), 2.71 (m, 2 H), 1.76 (m, 2 H), 1.44 (s, 9 H), 1.26 (d, J=6.5, 3 H)

MS: 328 (M+H)$^+$:

Tether T110 b can be made using this route substituting (R)-methyl lactate in the third step. An alternative synthetic route analogous to that described previously for T109 is provided in the following that can be applied to either T110a or T110b using (S)-methyl lactate or (R) methyl lactate respectively.

Alternative Synthetic Route to T110

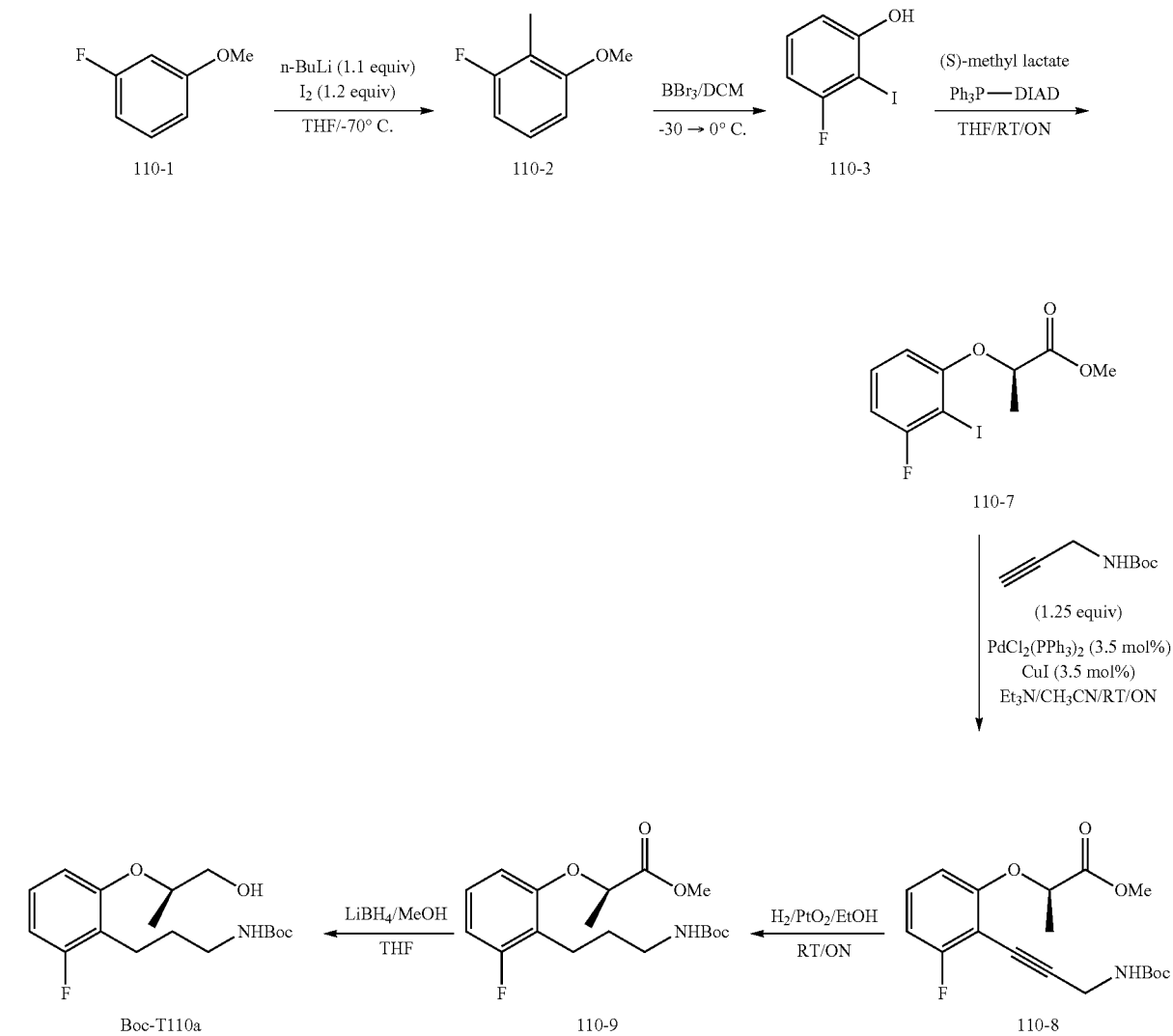

N. Standard Procedure for the Synthesis of Tether T111

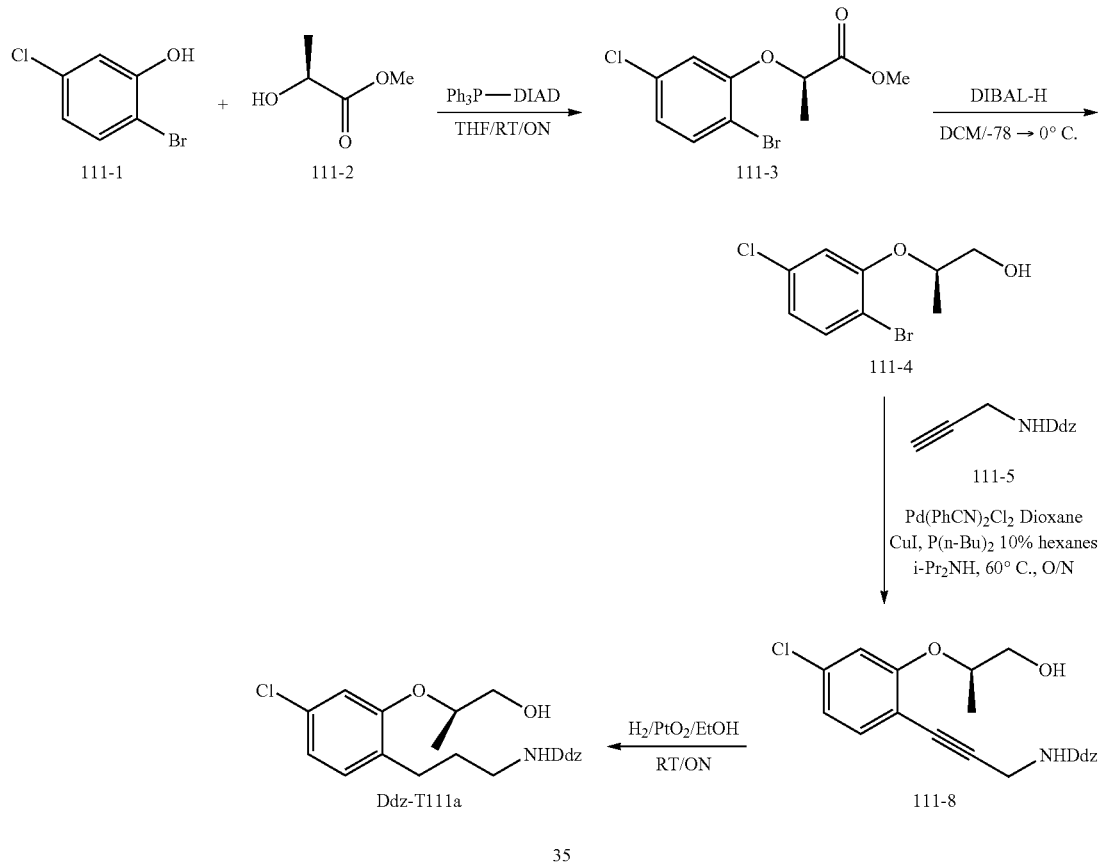

In a similar manner to that previously described for T75 (WO 2006/009674). Ddz-T111a was constructed starting from 2-bromo-5-chlorophenol (111-1) and (S)-methyl lactate (111-2). The corresponding Boc-protected tether was prepared using Boc instead of Ddz protection on the alkyne 111-5. The enantiomeric tether, T111b, is synthesized starting from (R)-methyl lactate in place of 111-2.

O. Standard Procedure for the Synthesis of Tether T112

Tether Boc-T112a was synthesized utilizing the route shown in 47% overall yield from 4,5-difluoro-2-bromophenol (112-I, 5.0 g, 23.92 mmol, 1.0 eq) and, (S)-methyl-(−)-lactate (2.39 g, 28.7 mmol, 1.2 eq). The corresponding Ddz-protected T112 was prepared using Boc instead of Ddz protection on the alkyne 112-0. The enantiomeric tether, T112b, is synthesized starting from (R)-methyl lactate in the first step.

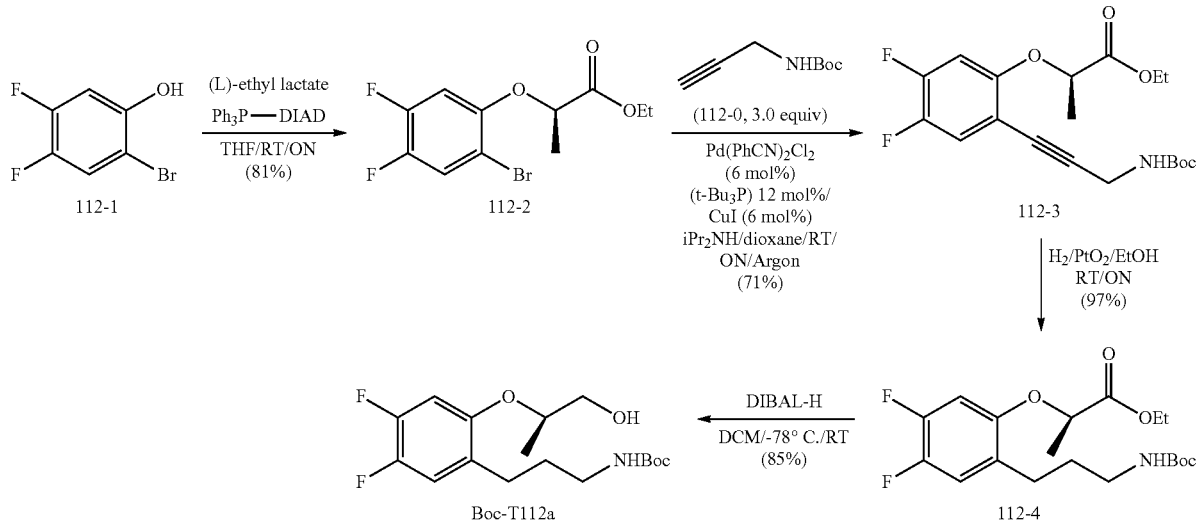

¹H NMR (CDCl₃, 300 MHz) δ 6.92 (m, 1 H), 6.71 (m, 1 H), 4.39 (m, 1 H), 3.77 (m, 2 H), 3.07 (m, 2 H), 2.56 (m, 3 H), 1.72 (m, 2 H), 1.44 (s, 9 H), 1.25 (d, j=6.2, 3 H)

MS: 246 (M+H-Boc)⁺

P. Standard Procedure for the Synthesis of Tether T114

Perkin Trans. 1 2000, 367-376.) This provides 114-5a as the free alcohol, which can be transformed into T114a and T114d, with (S)-methyl lactate (114-0) and (R)-methyl lactate, respectively, in the subsequent reaction to form 114-8. Similarly, use of intermediate 114-5b also produced in the

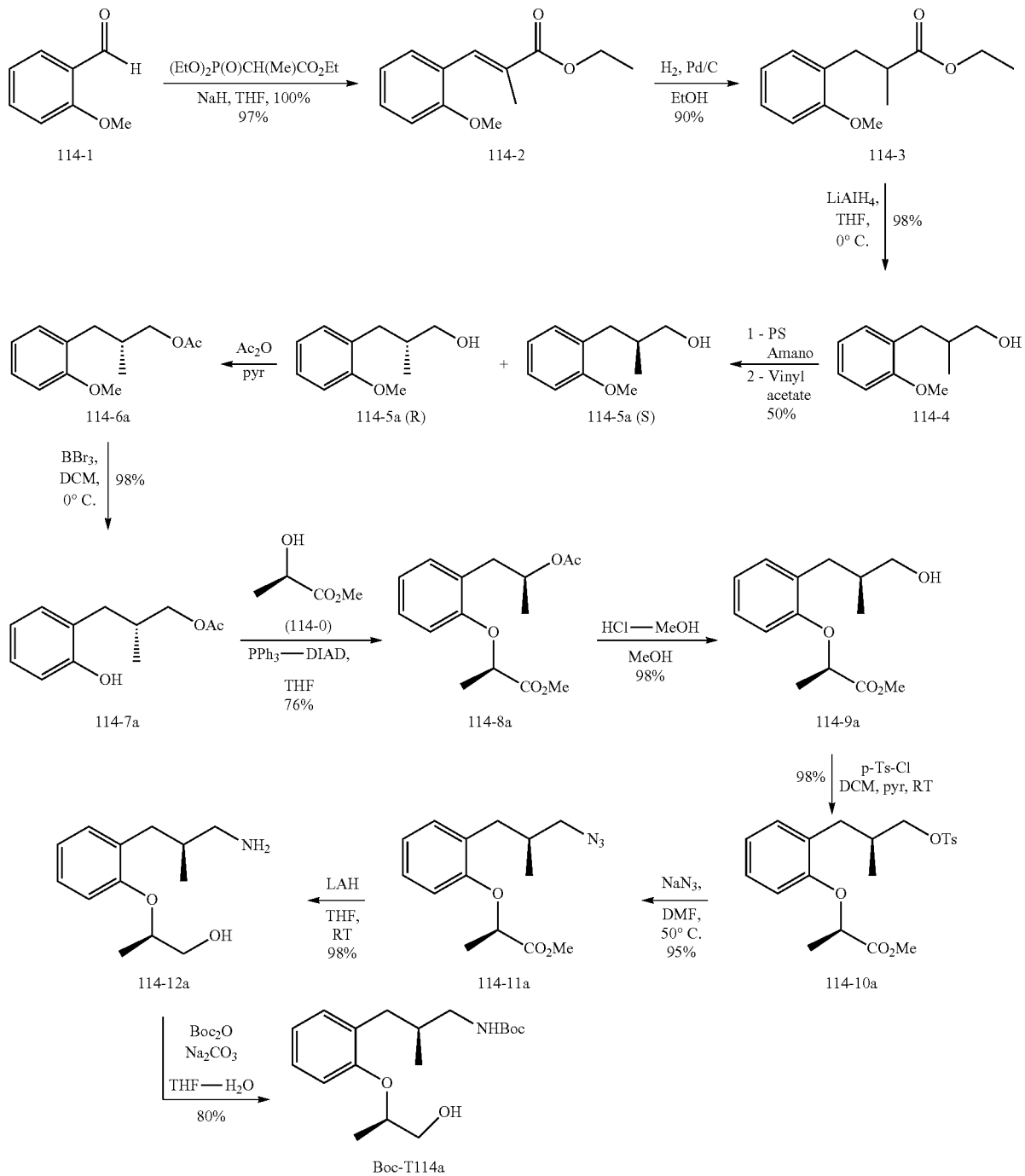

The synthesis of Boc-T114 required the lengthy sequence illustrated starting from 2-methoxybenzaldehyde (114-1). The key step is the kinetic resolution of intermediate 114-4 using PS Amano lipase. (Nordin, O.; Nguyen, B.-V.; Vörde, C.; Erik Hedenström, E.; Högberg, H.-E. *J. Chem. Soc., Perkin Trans. 1* 2000, 367-376.)

resolution process can provide T114b and T114c, with (S)-methyl lactate (114-0) and (R)-methyl lactate, respectively. In this manner, all of the four diastereomers of this tether can be accessed. Alternative protecting groups, such as Ddz or Fmoc, can be introduced using standard methods in the final step as required.

Q. Standard Procedure for the Synthesis of Tether T115

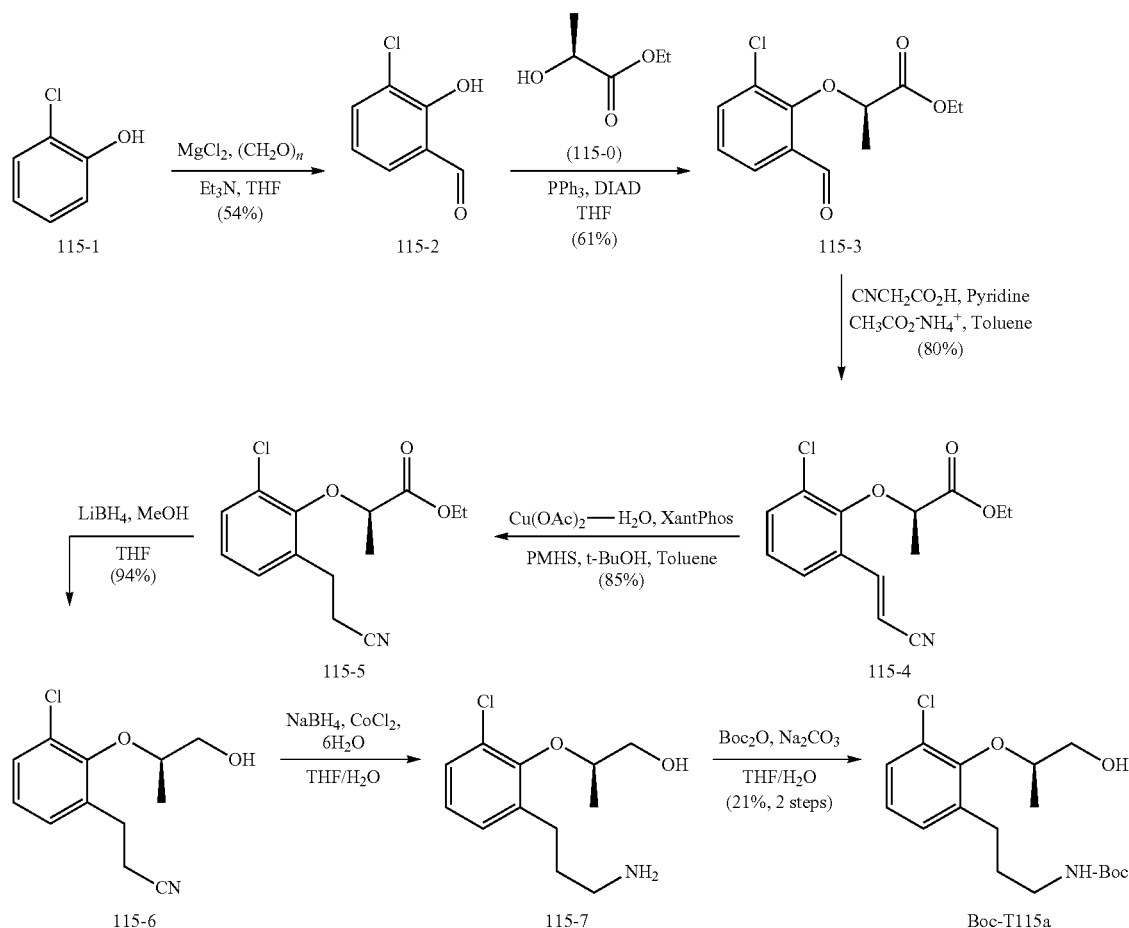

Boc-T115 has been prepared from 2-chlorophenol (115-1) and (S)-ethyl lactate (115-0) using the multi-step procedure shown.

TLC: $R_f$=0.45 [Hexanes/MTBE (3:7)], detection: UV+Mo/Ce $^1$H NMR (CDCl$_3$): δ 7.23-7.20, (m, 1H), 7.01-7.07, (m, 1H), 7.02-6.95 (m, 1H), 5.15-4.93 (bs, 1H), 4.58-4.49 (m, 1H), 3.91-3.86 (dd, 1H), 3.77-3.71 (dd, 1H), 3.17-3.07 (m, 1H), 3.03-2.94 (m, 1H), 2.86-2.73 (q, 1H), 2.72-2.61 (q, 1H), 2.22-2.00 (bs, 1H), 1.84-1.65 (m, 2H), 1.45 (s, 9H), 1.24-1.19 (d, 3H).

Use of (R)-ethyl lactate in the second step provides the enantiomeric tether, T115b. Alternative ester groups compatible with the reaction sequence can be similarly employed.

R. Standard Procedure for the Synthesis of Tether T116

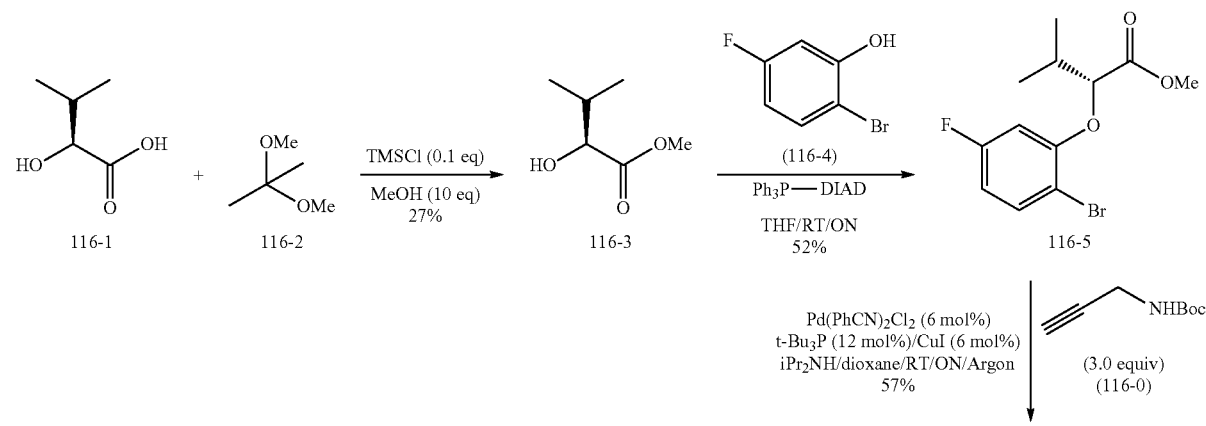

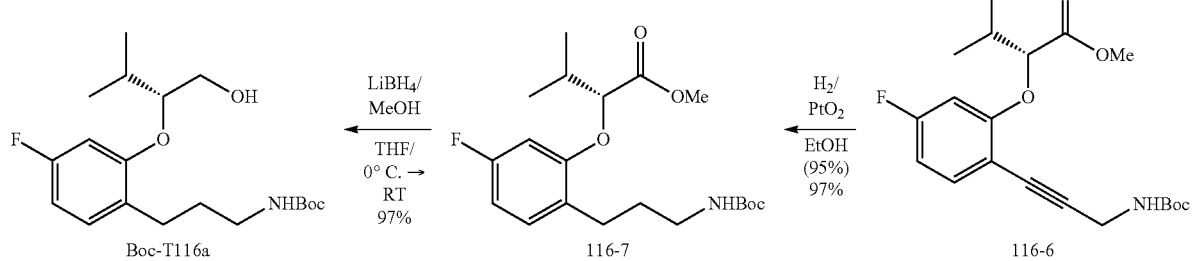

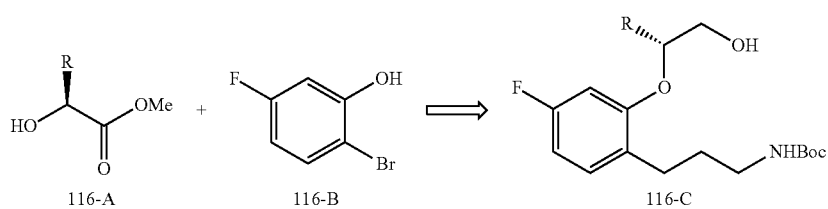

The route to T116 begins with the Mitsunobu reaction of methyl ester (116-3) of (S)-(+)-2-hydroxy-3-methyl butyric acid (116-1, Spur, B. W. et. al. *Tetrahedron Lett.* 1998, 39, 8563-8566) and 5-fluoro-2-bromophenol (116-4). Subsequent Sonagashira coupling, hydrogenation and ester reduction provided Boc-T116a in 18% overall yield from 116-3.

$^1$H NMR (CDCl$_3$, 300 MHz): δ 7.04 (m, 1 H), 6.63 (dd, J=2.3, 11.4, 1 H), 6.56 (dt, J=2.3, 8.2, 1 H), 4.13 (m, 1 H), 3.85 (d, J=4.7, 2 H), 3.09 (m, 2 H), 2.74 (m, 1 H), 2.52 (m, 1 H), 2.12 (m, 2 H), 1.77 (m, 2 H), 1.43 (s, 9 H), 1.02 (d, J=7.0, 3 H), 0.97 (d, J=6.7, 3 H)

MS: 256 (M+H-Boc)$^+$

Similar methods can be employed from appropriate starting materials to provide other alkylated derivatives (116C). Use of the enantiomeric (R)-ester of 116-1 leads to Boc-T116b. Likewise, other protecting groups, as long as they are compatible with the hydrogenation and borohydride reduction steps which is known to those in the art, can be used on the alkyne (116-0) to provide the tether with alternative protection.

Synthesis of T116 Analgoues with Alternative R Groups

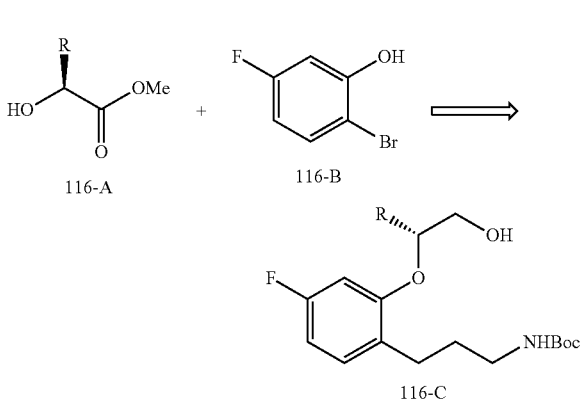

S. Standard Procedure for the Synthesis of Tether T117

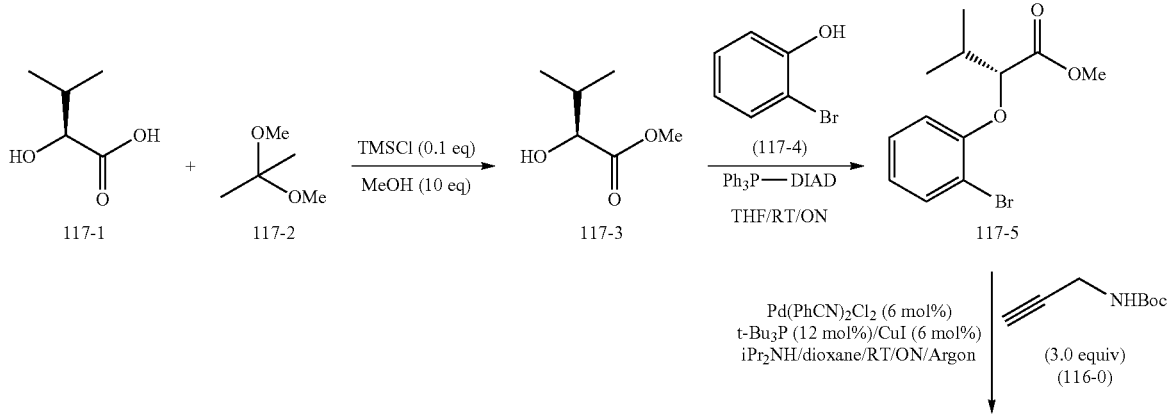

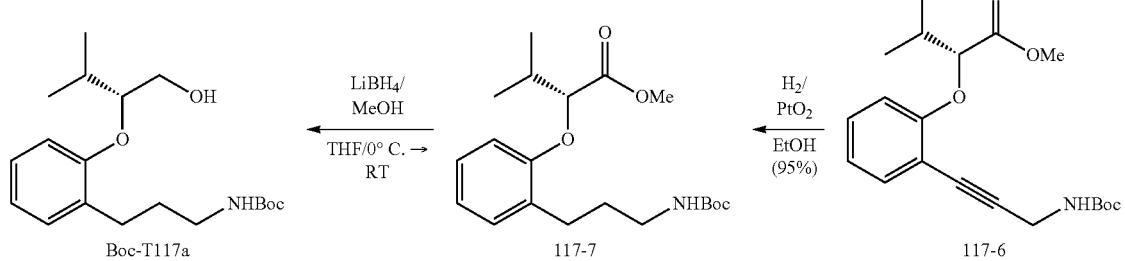

The construction of this tether parallels that of T116, but starts from 2-bromophenol and the methyl ester (117-3) of (S)-(+)-2-hydroxy-3-methyl butyric acid (1176-1, Spur, B. W. et. al. *Tetrahedron Lett.* 1998, 39, 8563-8566).

Likewise, the same considerations with respect to stereoisomers, protection strategies and alternative R groups as described for T116 also holds for T117.

T. Standard Procedure for the Synthesis of Tether T118

D.; Sieser, J. E. *Tetrahedron Lett.* 2000, 41, 2299-2302. Opening of the lactone with ammonia, LAH reduction of the amide and protection of the 118-5. Mitsunobu reaction with (S)-methyl lactate and lithium borohydride reduction of the product completed the construction of Boc-T118.

$^1$H NMR (300 MHz, CDCl$_3$): δ 7.16 (m, 2 H), 6.92 (m, 2 H), 4.54 (m, 1 H), 3.68 (m, 2 H), 3.30 (m, 2 H), 2.78 (m,

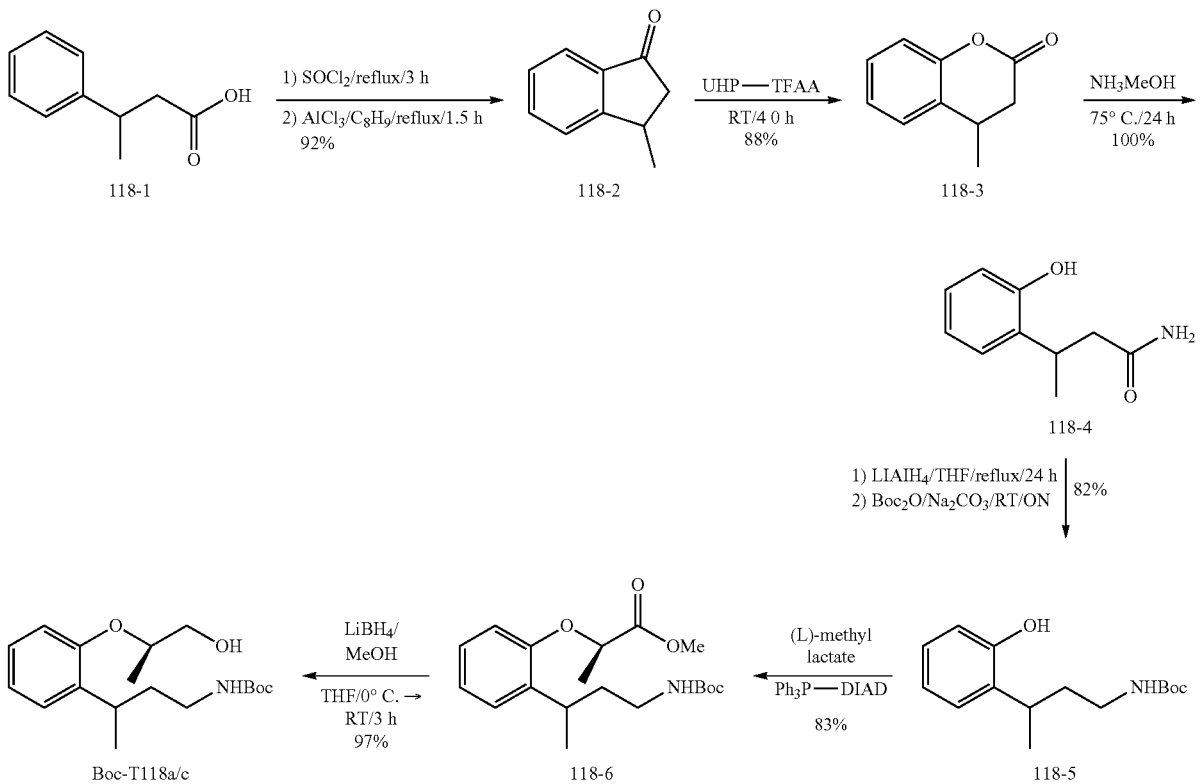

Staring from (±)-3-Phenylbutyric acid (118-1) and using the scheme outlined, tether T118 was prepared as a mixture of stereoisomers at the (*)carbon atom, although that at the other chiral center is controlled by that of the lactate ester. Treatment of 118-1 with thionyl chloride followed by intramolecular Freidel-Crafts acylation gave 118-2 (Smonou, I.; Orfanopoulos, M. *Synth. Commmun.* 1990, 20, 1387-1397; Stephan, E. et. al. *Tetrahedron: Asy.* 1994, 5, 41-44). Baeyer-Villager reaction of 118-2 with urea hydrogen peroxide (UHP) proceeded to give racemic 118-3 (Caron, S.; Do, N.

1 H), 2.67 (s, br, 1 H), 1.67 (m, 2 H), 1.44, 1.43 (s, 9 H), 127 (m, 6 H)

MS: 324 (M+H)$^+$

Use of (R)-methyl lactate in the second step provides the diastereomeric tethers, T118b/d. In order to obtain one isomer at the * carbon atom, use of an enantiomeric coumarin corresponding to 118-3 is required. This can be accessed using the method shown for the synthesis of 118-10 (Arp. F. O.; Fu, G. C. *J. Am. Chem. Soc.* 200, 127, 1048210483).

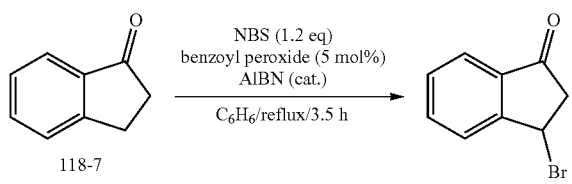
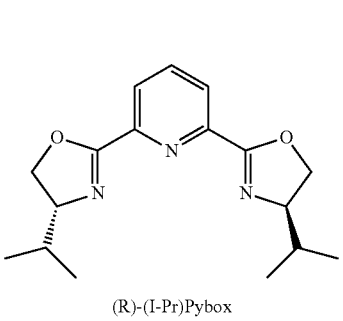
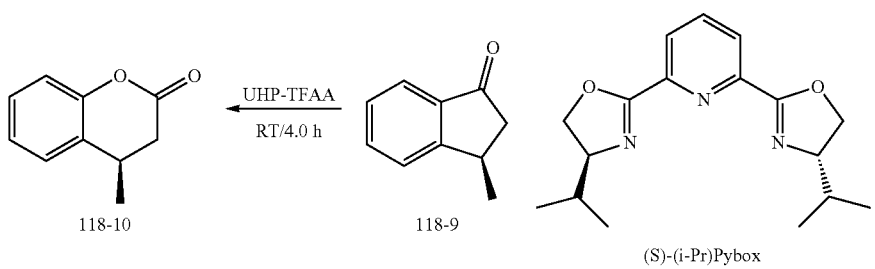

Note that catalytic AIBN was employed in the first step to give (±)-3-bromo-1-indanone (118-8) in high yield (Minuti, L. et. al. *Tetrahedron* 1993, 51, 8953-8958). Asymmetric alkylation of 118-8 in the presence of (R)-(i-Pr)Pybox gave the optically active product 118-9 as the (R)-isomer. Subsequent Bayer-Villager reaction provided (R)-118-10 in 31% overall yield.

$^1$H NMR (300 MHz, CDCl$_3$): δ 7.25 (nm, 1 H), 7.13 (dt, J=1.2, 7.3, 1 H), 7.06 (m, 1 H), 3.18 (m, 1 H), 2.85 (dd, J=5.6, 15.8, 1 H), 2.58 (dd, J=7.3, 15.8, 1 H), 1.34 (d, J=7.0, 3 H.)

The (S)-enantiomer of 118-9 can be obtained in 58% isolated yield by using (S)-(i-Pr)Pybox, which can be converted similarly to (S)-118-10.

U. Standard Procedure for the Synthesis of Tether T119

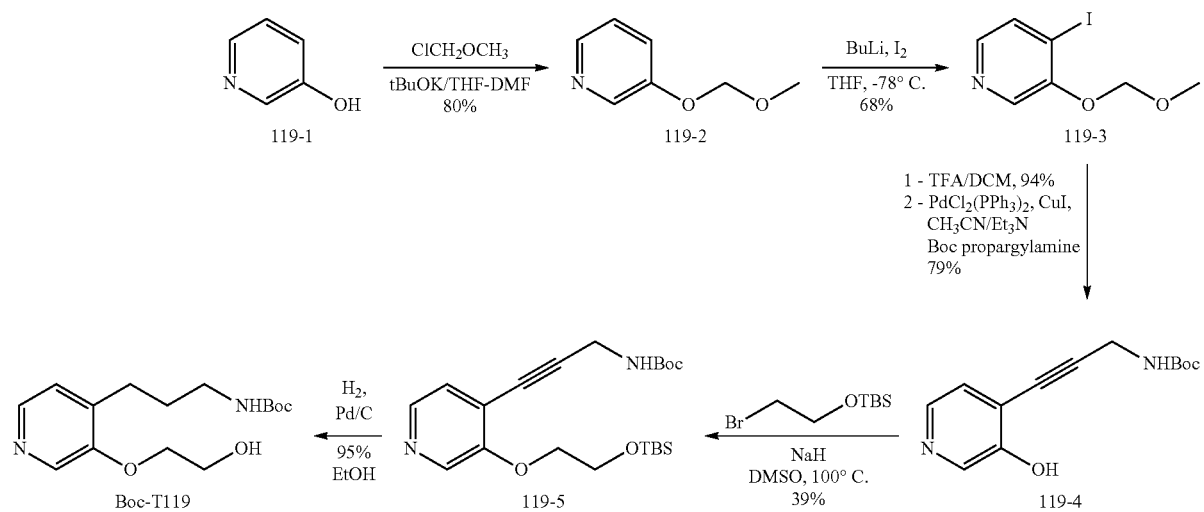

Boc-T19 is prepared from 3-hydroxypyridine (119-1, 14 g, 0.147 mmol) using the reaction sequence shown in an overall yield of 14-15%.

V. Standard Procedure for the Synthesis of Tether T122
Synthesis of Boc-(2RMe,NMe)o18r Tether

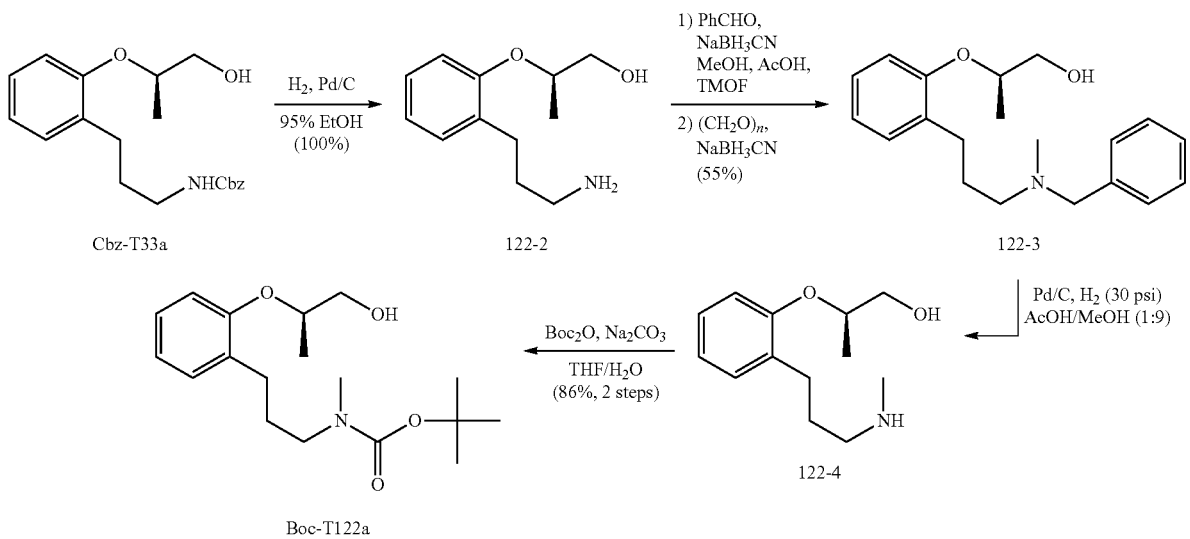 [SMILES: C[C@H](CO)Oc1ccccc1CCCNC(=O)OCc1ccccc1 ; C[C@H](CO)Oc1ccccc1CCCN ; C[C@H](CO)Oc1ccccc1CCCN(C)Cc1ccccc1 ; C[C@H](CO)Oc1ccccc1CCCN(C)C(=O)OC(C)(C)C ; CNCCCc1ccccc1O[C@H](C)CO]

Boc-T122a is synthesized in 47% overall yield in five steps originating from a different tether, Cbz-T33a, as summarized in the scheme.

TLC: $R_f$=0.50 [Hexanes/EtOAc (1:1)], detection: UV+Mo/Ce

MS: 323 (M+)

W. Standard Procedure for the Synthesis of Tether T123

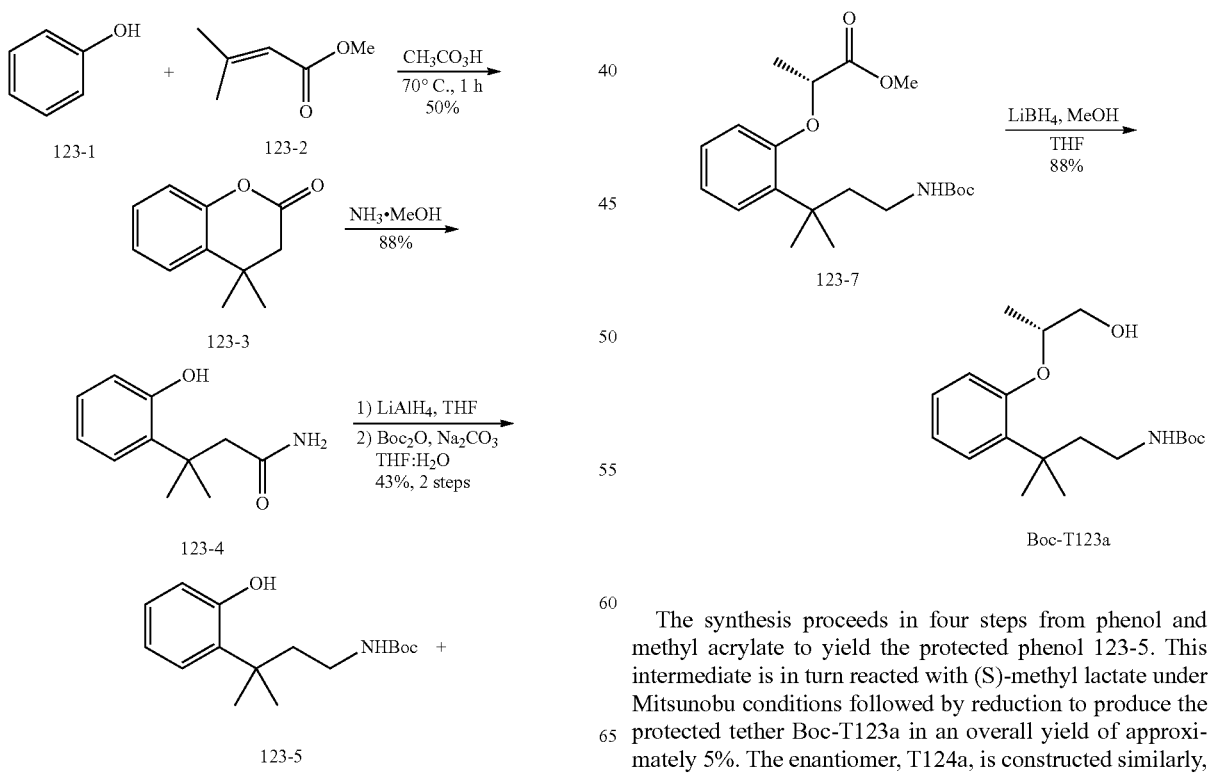

The synthesis proceeds in four steps from phenol and methyl acrylate to yield the protected phenol 123-5. This intermediate is in turn reacted with (S)-methyl lactate under Mitsunobu conditions followed by reduction to produce the protected tether Boc-T123a in an overall yield of approximately 5%. The enantiomer, T124a, is constructed similarly, but using (R)-methyl lactate.

X. Standard Procedure for the Synthesis of Tether T-124

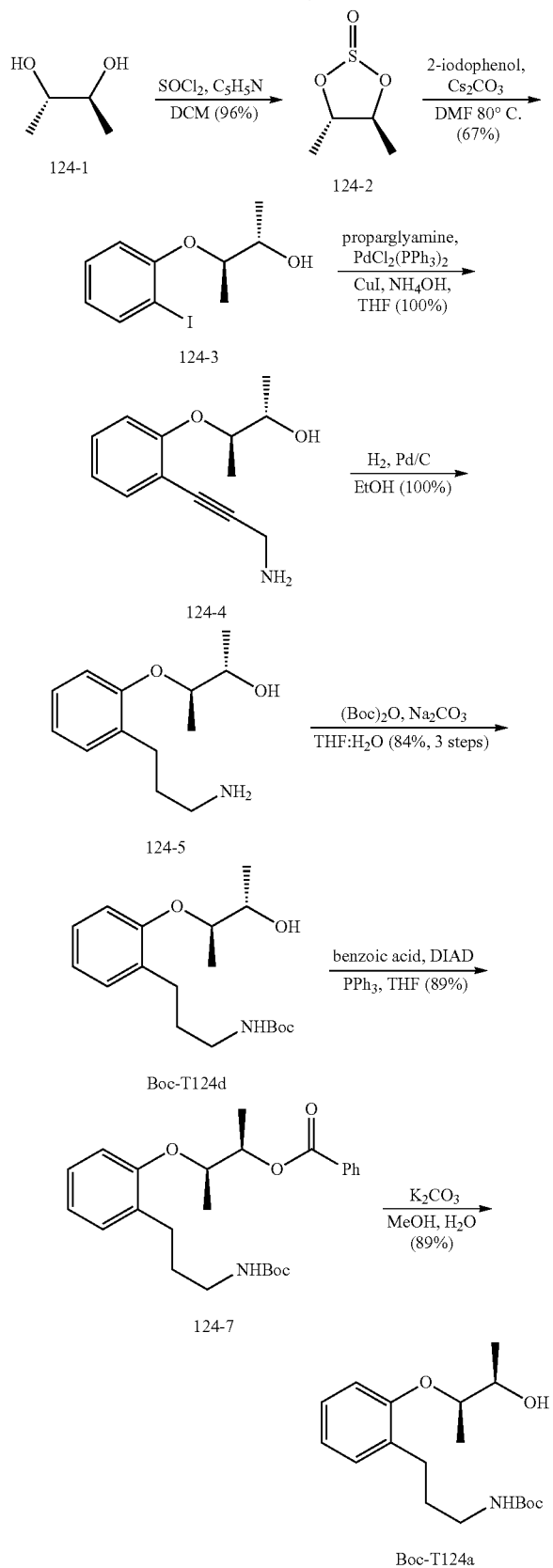

Two of the diastereomers of T124 can be accessed beginning from opening of the cyclic sulfite of (2S,3S)-butanediol (124-1) with 2-iodophenol to give 124-3. Subsequent Sonagashira coupling, hydrogenation, and Boc protection provided Boc-T124d.

$^{1}$H-NMR (CDCl$_3$, 300 MHz): δ 7.19-7.11 (m, 2H), 6.92-6.83 (m, 2H), 4.88 (br s, 1H), 4.38 (dq, 1H, J=3.1 & J=6.3 Hz), 4.07 (br s, 1H), 3.16-3.04 (m, 2H), 2.73-2.57 (m, 2H), 2.27 (br s, 1H), 1.83-1.72 (m, 2H), 1.45 (s, 9H), 1.28 (d, 3H, J=4.2 Hz), 1.26 (d, 3H, J=: 4.0 Hz)

LC-MS (Grad B4) t$_R$: 12.57 min

Inversion of the chiral alcohol center of T124d under Mitsunobu conditions followed by hydrolysis yielded Boc-T124a.

TLC: R$_f$=0.5 (EtOAc:Hexanes, 1:1), detection: UV, CMA
$^{1}$H-NMR (CDCl$_3$, 300 MHz): δ 7.19-7.12 (m, 2H), 6.93-6.86 (m, 2H), 4.86 (br s, 1H), 4.23 (p, 1H, J=3.1 & 6.3 Hz), 3.95-3.87 (m, 1H), 3.11 (dd, 2H, J=6.2 & 12.7 Hz), 2.66 (t, 2H, J=7.3 Hz), 2.56 (br s, 1H), 1.82-1.71 (m, 2H), 145 (s, 9H), 1.28 (d, 3H, J=6.4 Hz), 1.25 (d, 3H, J=6.1 Hz)

LC-MS (Grad A4) t$_R$: 7.59 min

The other two diastereoisomers of T124 were accessed with an essentially identical strategy from the cyclic sulfite of (2R,3R)-butanediol (124-8) as shown.

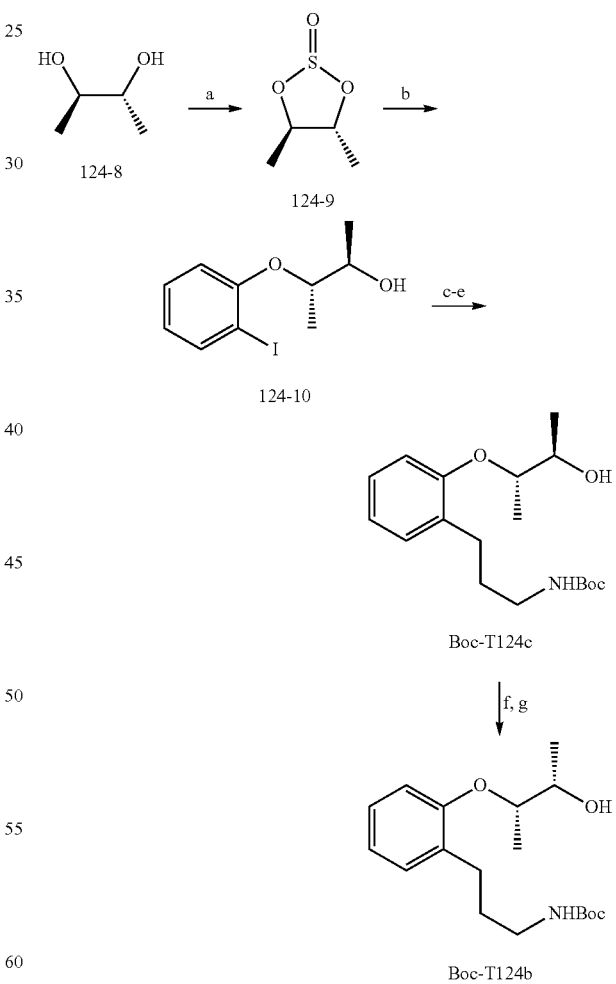

a. SOCl$_2$, C$_5$H$_5$N, DCM (91%);
b. 2-iodophenol, Cs$_2$CO$_3$, DMF, 80° C. (71%);
c. proparglyamine, PdCl$_2$(PPh$_3$)$_2$, CuI, NH$_4$OH, THF;
d. H$_2$, Pd/C, EtOH;
e. (Boc)$_2$O, Na$_2$CO$_3$, THF:H$_2$O (58%, 3 steps);
f. benzoic acid, DIAD, PPh$_3$, THF (61%); g. K$_2$CO$_3$, MeOH, H$_2$O (88%)

Y. Standard Procedure for the Synthesis of Tether T125

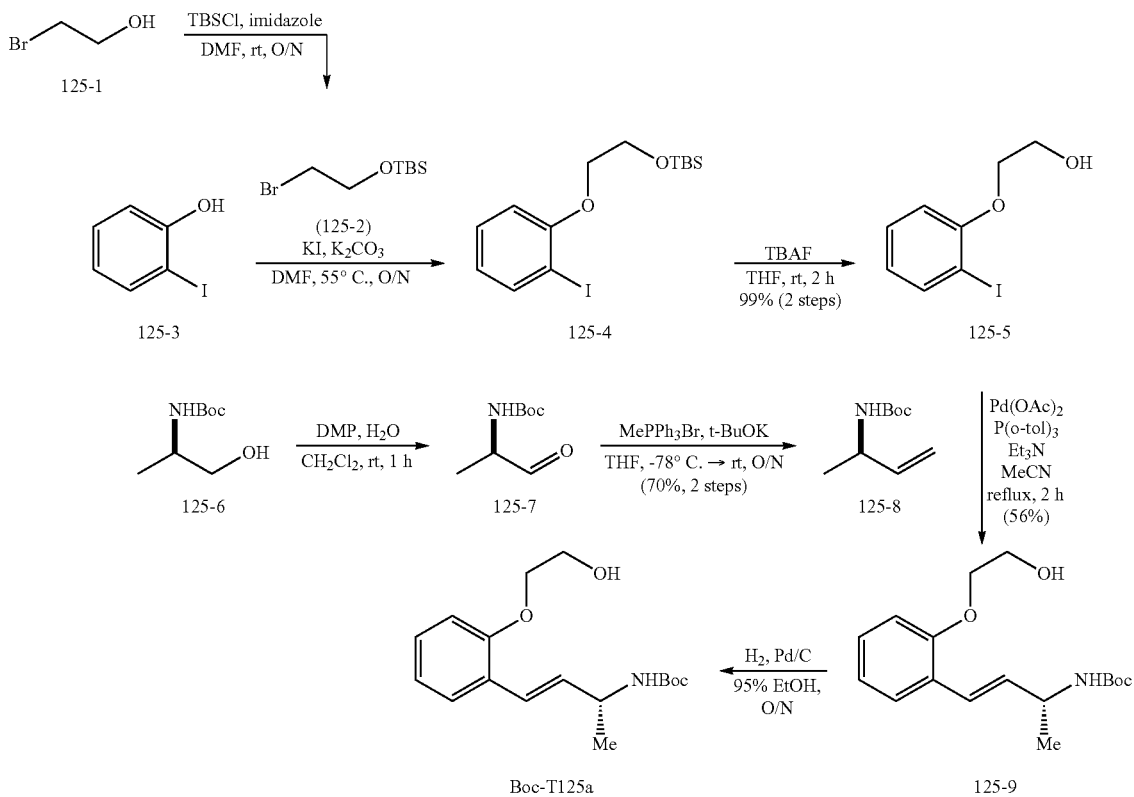

Starting from 2-bromoethanol (125-1), 2-iodophenol (125-3) and Boc-(R)-alaninol (125-6), the tether (Boc-T125a) was obtained in 50-60% overall yield.

The (S) isomer, Boc-T125b, is synthesized analogously starting from Boc-(S)-alaninol.

Z. Standard Procedure for the Synthesis of Tether T126

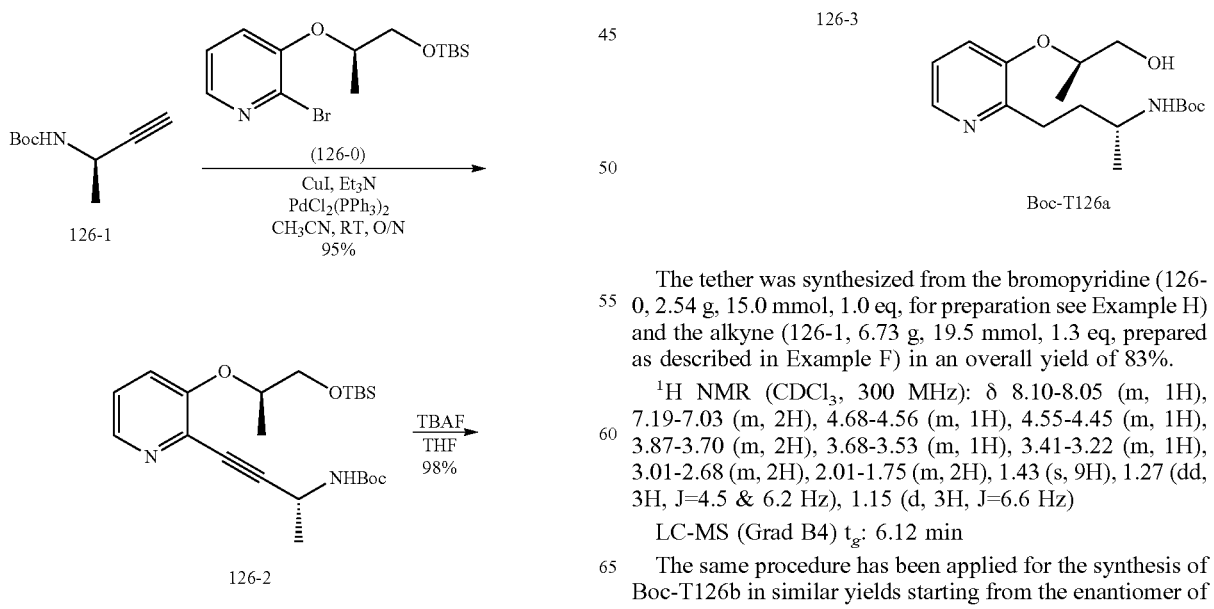

The tether was synthesized from the bromopyridine (126-0, 2.54 g, 15.0 mmol, 1.0 eq, for preparation see Example H) and the alkyne (126-1, 6.73 g, 19.5 mmol, 1.3 eq, prepared as described in Example F) in an overall yield of 83%.

$^1$H NMR (CDCl$_3$, 300 MHz): δ 8.10-8.05 (m, 1H), 7.19-7.03 (m, 2H), 4.68-4.56 (m, 1H), 4.55-4.45 (m, 1H), 3.87-3.70 (m, 2H), 3.68-3.53 (m, 1H), 3.41-3.22 (m, 1H), 3.01-2.68 (m, 2H), 2.01-1.75 (m, 2H), 1.43 (s, 9H), 1.27 (dd, 3H, J=4.5 & 6.2 Hz), 1.15 (d, 3H, J=6.6 Hz)

LC-MS (Grad B4) t$_g$: 6.12 min

The same procedure has been applied for the synthesis of Boc-T126b in similar yields starting from the enantiomer of 126-1.

AA. Standard Procedure for the Synthesis of Tether T129

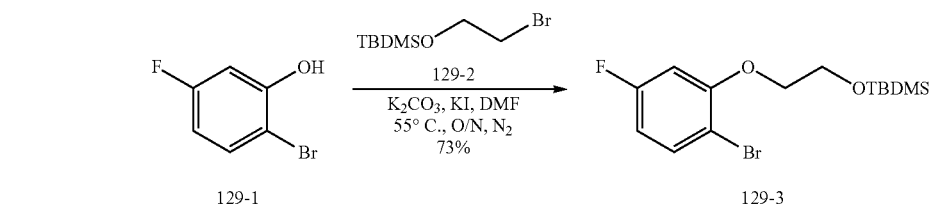

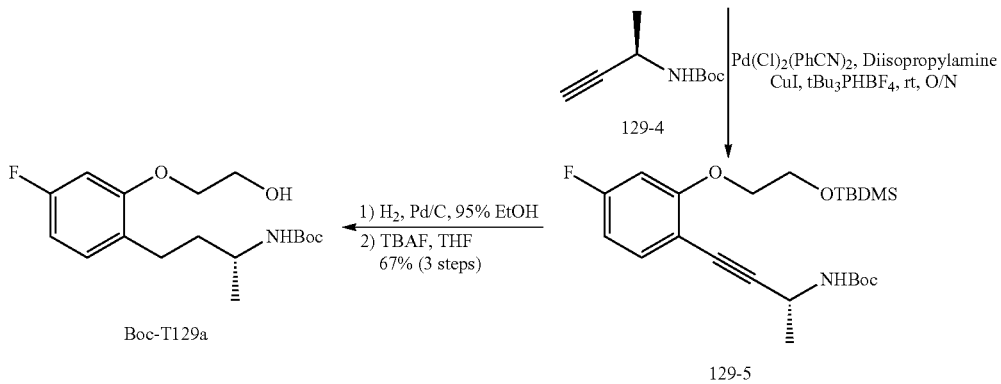

Boc-T129a was produced from 5-fluoro-2-bromophenol (129-1), TBDMS-protected 2-bromo-ethanol (129-2) and Boc-(R)-methylpropargylamine (129-4) using the reaction sequence presented in 48% overall yield.

$^1$H NMR (CDCl$_3$, 300 MHz): δ 7.07-7.00 (m, 1 H, aryl), 6.62-6.52 (m, 2 H, aryl), 4.60 (bs, 1 H, NHBoc), 4.08-3.90 (m, 4 H, OCH$_2$CH$_2$OH)), 3.70-3.55 (m, 1 H, CH$_3$CHNHBoc), 3.18-3.32 (bs, 1H, OH), 2.75-2.42 (m, 2 H, arylCH$_2$), 1.92-1.50 (m, 2 H, CH$_2$CH$_2$CH), 1.45 (s, 9 H, C(CH$_3$)$_3$,) 1.14 (d, J=6.6, 3 H, CHCH$_3$)

MS: 327 (M$^+$)

The enantiomeric tether Boc-T129b likewise can be prepared using the same sequence from Boc-(S)-methylpropargylamine.

BB. Standard Procedure for the Synthesis of Tether T130

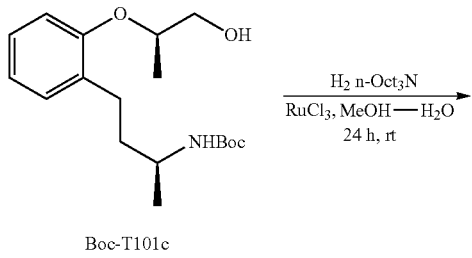

-continued

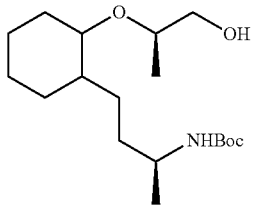

In a manner analogous to the synthesis of tether T102 from T33, tether T30 can be obtained in 80-90% yield from the corresponding aromatic compound by catalytic hydrogenation. Other side chain stereoisomers apart from than that illustrated can be accessed from their corresponding precursors similarly.

CC. Standard Procedure for the Synthesis of Chiral T102, T104 and T130 Tethers

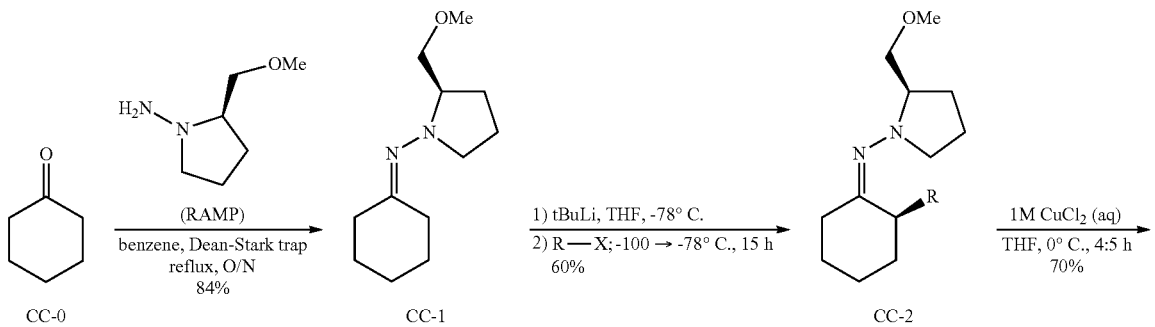

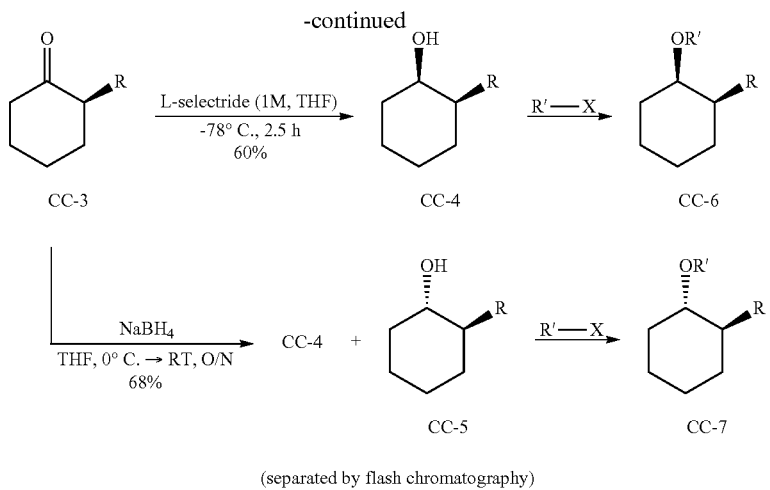

(separated by flash chromatography)

To provide access these tethers in optically active form, an alternative methodology is required to introduce the centers on the cyclohexane ring. For this purpose, the use of Enders asymmetric hydrozone alkylation methodology proved useful. (Job, A.; Carsten F. Janeck, C. F.; Bettray, W.; Peters, R. Enders, D. *Tetrahedron* 2002, 58, 2253-2329.) As illustrated, the chiral cyclohexanone derivative (CC-1) was prepared under standard conditions, then alkylated with an appropriate first electrophile (R-X). Subsequent hydrazone hydrolysis let to the chiral cyclohexanone CC-3. Depending on the reagent employed in the reduction step, either the cis (CC-4) or trans (CC-5) isomer could be obtained. L-Selectride produced exclusively the cis, while sodium borohydride produced an approximately 1:1 mixture of CC-4:CC-5, from which the desired product could be isolated by flash chromatography (gradient, 10/1 to 7/1 to 5/1, Hexanes/Ethyl Acetate). The chiral alcohols can be alkylated with a second electrophile to prepare the desired tether as will be clear to those in the art. For example, for T104, the first electrophile (R-X) could be ICH2CH2CH2NHBoc, while the second electrophile (R'-X) could be Br-CH2CH2OTBDMS. The yields presented are for T102. Use of the opposite chiral hydrazine (SAMP), provides the other stereoisomer at the center alpha to the carbonyl. In this manner, all the stereoisomers of these tethers can be prepared.

DD. Standard Procedure for the Synthesis of Tether T131

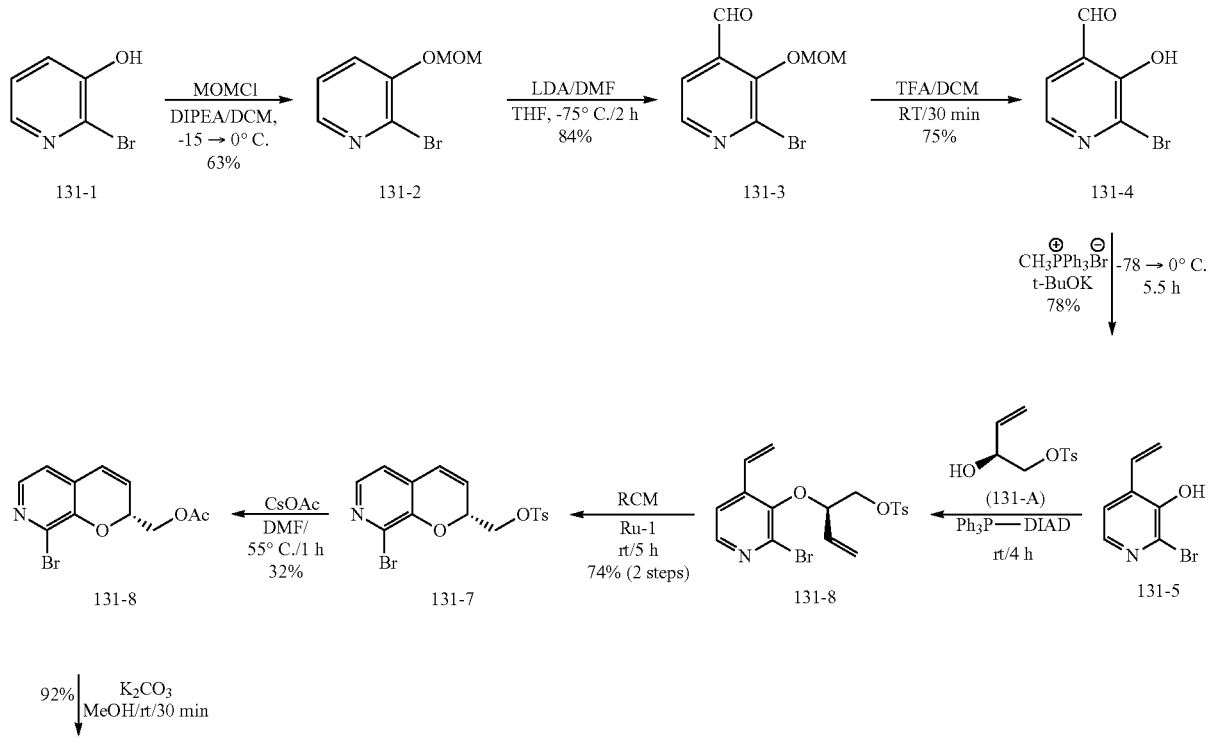

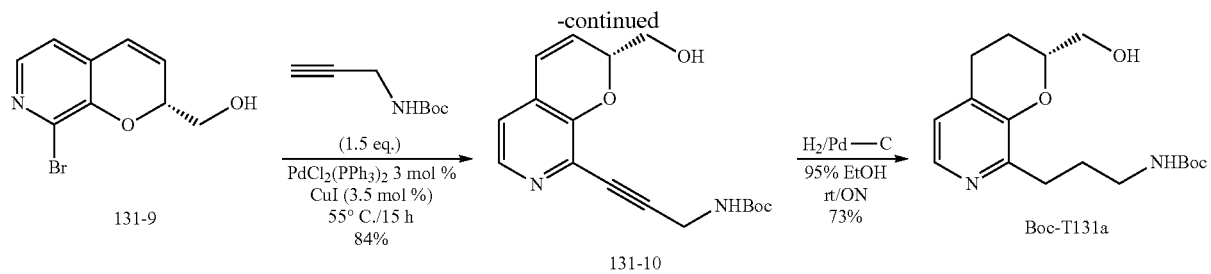

Synthesis of T131 proceeded from the known intermediate 131-3 (Schlosser, M. et. al. *Tetrahedron* 2005, 61, 717-725) via the multi-step sequence illustrated. For the key RCM step, either Grubb's second generation catalyst (Ru-1) or the Grubbs-Hoveyda catalyst (Ru-2) could be employed. The yield for the synthesis of 131-8 was complicated by concurrent elimination side reaction. In order to avoid this, an alternative synthetic route conducting the RCM prior to the displacement reaction can be employed.

$^1$H NMR (CDCl$_3$, 300 MHz): δ 7.97 (d, J=4.7, 1 H), 6.84 (d, J=5.0, 1 H), 5.02 (s, br, 1 H), 4.14 (m, 1 H), 3.83 (m, 2 H), 3.13 (m, 2 H), 2.80 (m, 5 H) 1.90 (m, 4 H), 1.44 (s, 9 H)

$^{13}$C NMR (CDCl$_3$, 75 MHz): δ 156.14, 150.12, 149.36, 140.12, 129.59, 122.20, 79.19, 77.20, 65.19, 40.13, 29.42, 28.42, 28.24, 24.06, 22.94

MS: 323 (M+H)$^+$:

EE. Standard Procedure for the Synthesis of Tether T132

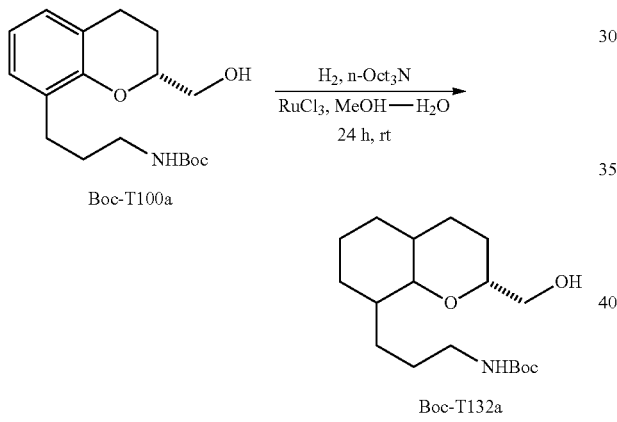

In a manner analogous to the synthesis of tether T102 from T33, tether T132 can be obtained in 80-90% yield from the corresponding aromatic compound, Boc-T100, by catalytic hydrogenation. Likewise, reduction of Boc-T100b provides Boc-T132b FF. Standard Procedure for the Synthesis of Macrocycles Containing Tether T133

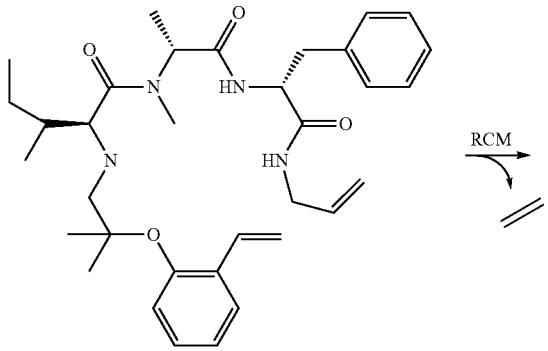

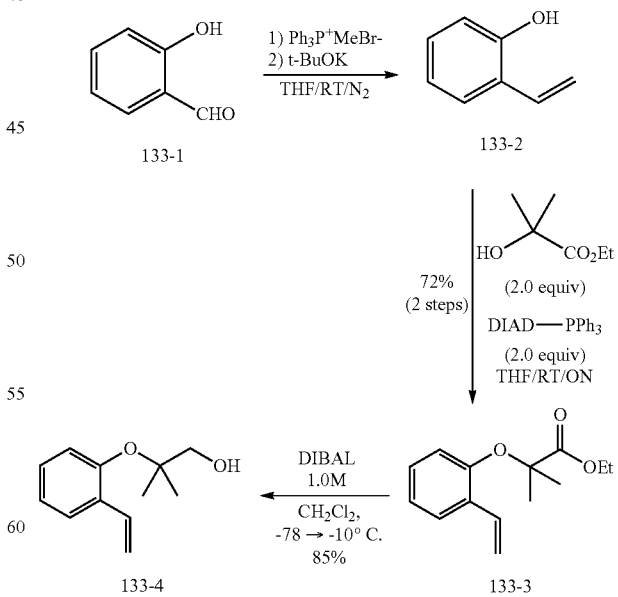

This tether is introduced in two pieces from appropriate precursors as illustrated. A detailed discussion of the use of RCM that can be applied to prepare compounds of the invention is presented in WO 2006/009674.

The necessary precursor, 133-4, is accessed through the procedure shown and then attached to the AA$_1$ amino acid typically via a Mitsubobu reaction. The allyl amide attached to the AA$_3$ amino acid, that provides the other part of the tether, is prepared using standard methods.

$^1$H NMR (CDCl$_3$, 300 MHz): δ 7.53 (dd, J=7.6, 2.1, 1 H), 7.11 (m, 4 H), 5.70 (dd, J=17.9, 1.5, 1 H), 5.27 (dd, J=11, 1.5, 1 H), 3.63 (s, 2 H), 2.18 (s, br, 1 H), 1.29 (s 6 H)

$^{13}$C NMR (CDCl$_3$, 75 MHz): δ 152.36, 132.54, 132.45, 128.30, 126.18, 123.60, 123.24, 114.53, 81.88, 70.51, 23.34
MS: 121 (M+H-72)

Example 12

Synthesis of Macrocycles

A. Standard Procedure for the Synthesis of Compound 801

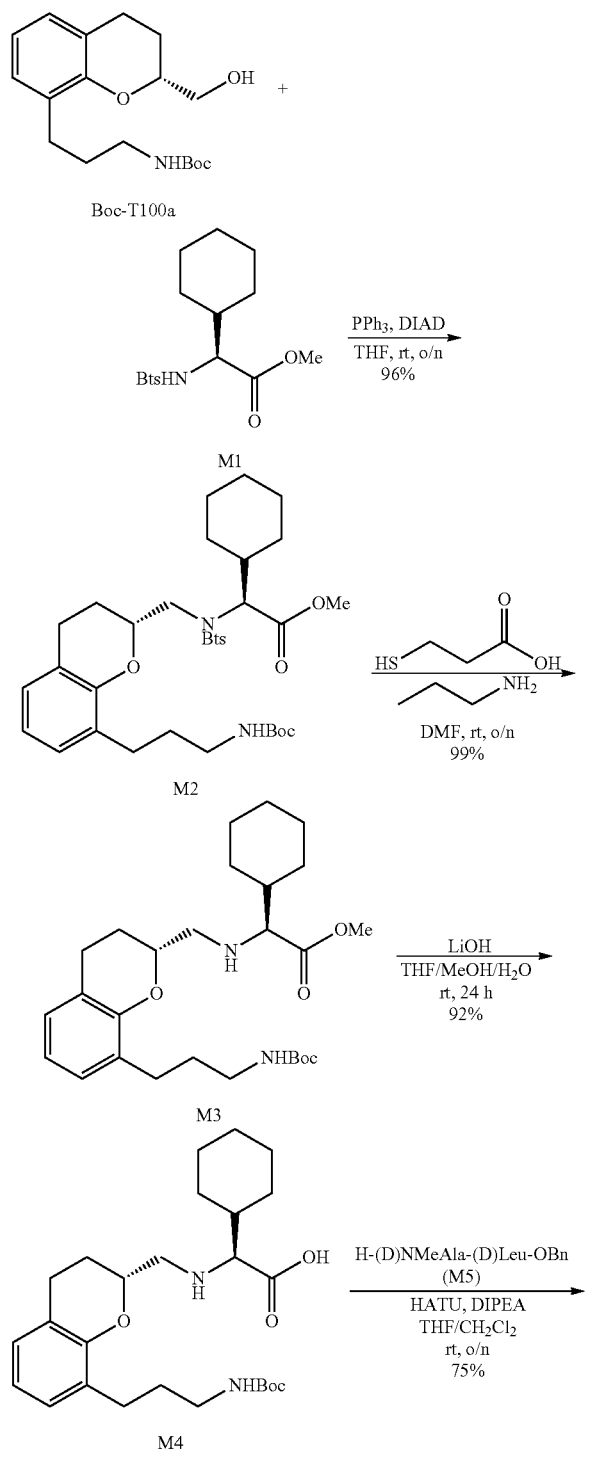

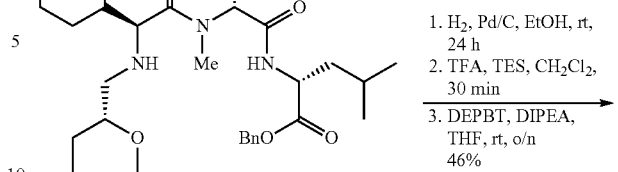

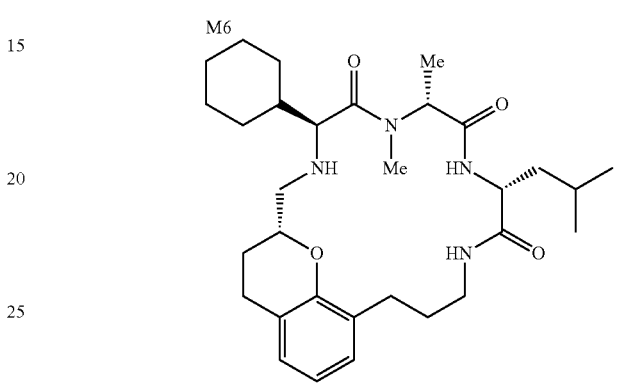

Step A-1: To a solution of Boc-T100a (35.04 g, 112 mmol, 1.1 eq) and M1 (37.46 g, 102 mmol, 1.0 eq) in THF (205 mL) was added PPh$_3$ (29.4 g, 112 mmol, 1.1 eq). The solution was cooled to 0° C. and DIAD (22 mL, 112 mmol, 1.1 eq) added over a period of 5 min. The ice bath was left in place and the reaction agitated overnight. Solvents were evaporated in vacuo and the residue was purified on dry pack column chromatography (5% acetone/toluene) to give M2 (73 g, 96%).

Step A-2: To a solution of M1 (73.0 g, 109 mmol, 1.0 eq) in DMF (550 mL) were added mercaptopropionic acid (47 mL, 545 mmol, 5 eq) and n-propylamine (45 mL, 545 mmol, 5 eq). The mixture was stirred at room temperature overnight. Water (1000 mL) was then added and the mixture extracted with Et$_2$O (4×500 mL). The combined organic phase was washed with a saturated solution of NaHCO$_3$ (2×500 mL) and brine (500 mL), dried with MgSO$_4$, filtered and concentrated under vacuum. The crude product was purified by dry pack column chromatography (25% AcOEt/hexanes) to give M3 (52.2 g, >99%).

Step A-3: To a solution of M3 in THF/MeOH/water (1:1:1) (1050 mL) was added LiOH (22.9 g, 545 mmol, 5 eq). The reaction was stirred overnight at room temperature. Another portion of LiOH (22.9 g, 545 mmol, 5 eq) was then added and the solution agitated for another 5 h. The volatiles were evaporated under vacuum, the resulting residue filtered on a medium flitted glass filter and washed with water (3×100 mL) and MTBE (2×100 mL). The white solid was left to dry in the air for 4 d to give M4 (50 g). To recover additional material from the filtrate, MTBE (100 mL) was added and the phases separated. The aqueous phase was extracted with MTBE (100 mL), saturated with LiCl and extracted again with AcOEt (5×300 mL). The combined organic phase was dried with MgSO$_4$, filtered and evaporated in vacuo to give additional M4 (3 g). The samples of M4 were combined and azeotroped with toluene (3×). The product was dried under high vacuum (oil pump) to give M4 (46.6 g, 92%).

Step A-4: To a solution of M4 (46.6 g, 99.9 mmol, 1.05 eq) and dipeptide MS (32.6 g, 95.1 mmol, 1.0 eq) in THF/CH$_2$Cl$_2$ (1:1) (1000 mL) was added DIPEA (83 mL, 476 mmol, 5 eq) and HATU (39.9 g, 105 mmol, 1.1 eq). The suspension became quite thick and difficult to stir, so THF/CH$_2$Cl$_2$ (1:1) (1000 mL) was added. The reaction was agitated overnight. The solvent was then evaporated and the residue dissolved in AcOEt (2000 mL) and 1 M citrate buffer (300 mL). The phases were separated and the organic phase washed sequentially with 1 M citrate buffer (300 mL), saturated NaHCO$_3$ (2×300 mL) and brine (500 mL). The organic phase was dried with MgSO$_4$, filtered and evaporated to give a residue that was purified on dry pack column chromatography (25%->50%->75% AcOEt/hexanes) to yield M6 (71.1 g, 74.6%).

Step A-5: A solution of M6 (53.2 g, 71 mmol, 1.0 eq) in 95% EtOH (1400 mL) was purged with nitrogen. Palladium catalyst (10% w/w on carbon, 50% wet, 3.02 g, 1.42 mmol, 0.02 eq) was then added and H$_2$ bubbled into the reaction overnight. The reaction mixture was purged with nitrogen, another portion of catalyst (12 g, 5.6 mmol, 0.08 eq) added and H$_2$ bubbled through the mixture for another 5 h. The reaction was then filtered on a Celite® pad and rinsed with 95% EtOH and AcOEt. The solvents were evaporated under vacuum and the residue azeotroped with toluene. The crude product thus obtained was dissolved in CH$_2$Cl$_2$ (500 mL) and TES (25 mL), then TFA (250 mL) added. The solution was agitated for 30 min, evaporated under vacuum and azeotroped with toluene (3×500 mL). The residue was dissolved in THF (1400 mL) under nitrogen and DIPEA (62 mL, 355 mmol, 5 eq) added. The solution was agitated for 5 min and DEPBT (27.6 g, 92.3 mmol, 1.3 eq) then added. The reaction was agitated overnight and evaporated in vacuo. A solution of 1 M Na$_2$CO$_3$ (1000 mL) was added, the mixture agitated 5 min, then AcOEt (400 mL) was added. The phases were separated and the aqueous phase extracted with AcOEt (3×500 mL), The combined organic phase was washed with a solution of 1 M Na$_2$CO$_3$ (250 mL), then brine (2×250 mL), dried with MgSO$_4$, filtered and evaporated under vacuum to provide 801 (17.5 g, 45.5%, 30% overall yield).

B. Standard Procedure for the Synthesis of Compound 807

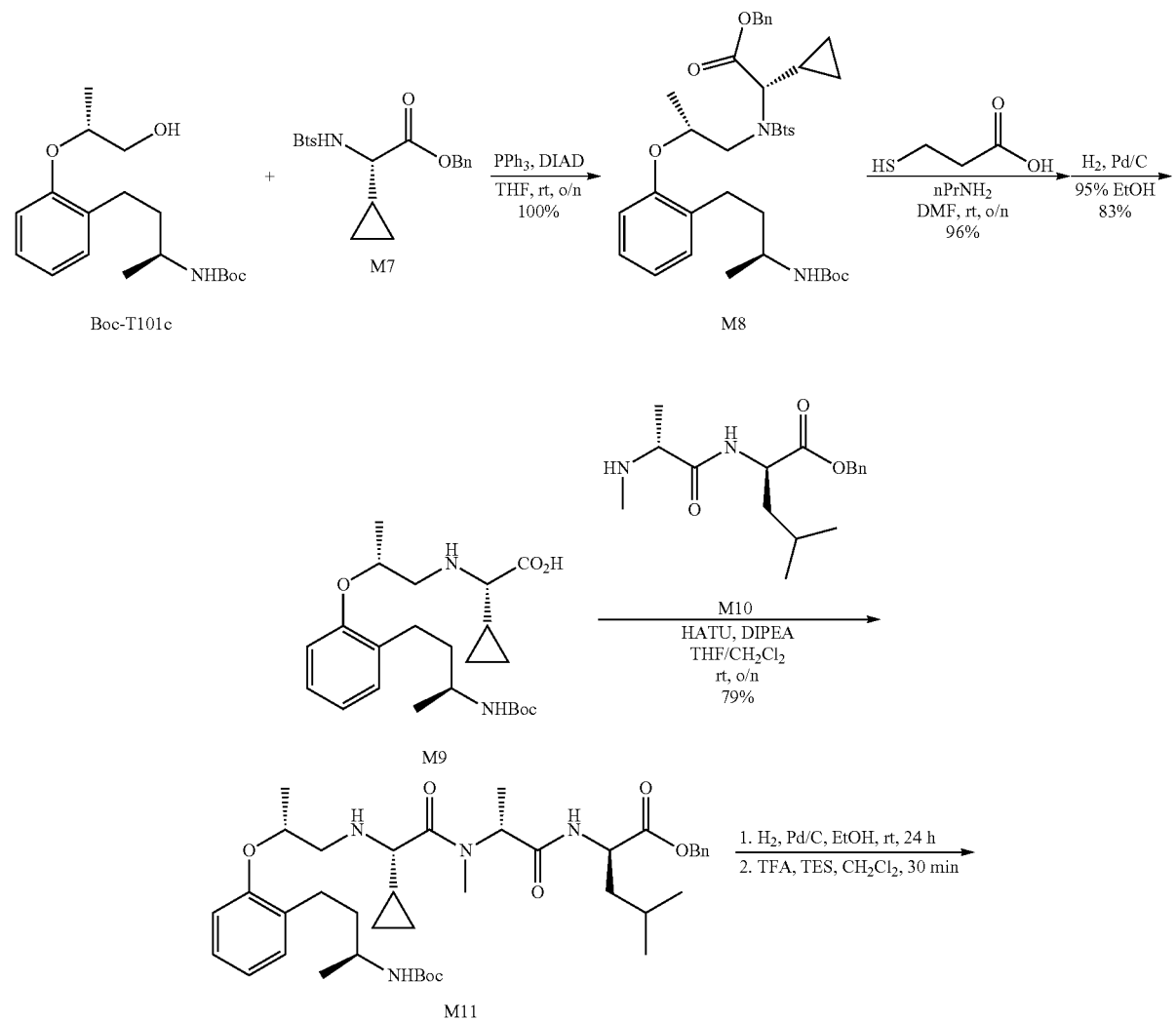

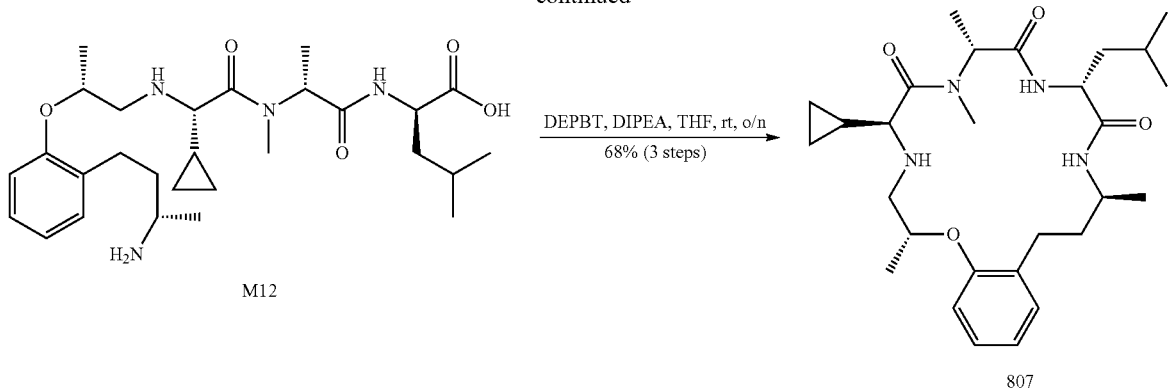

Utilizing a similar reaction sequence as described for compound 801, compound 807 was assembled from T101c, the protected cyclopropylglycine derivative (M7) and the protected dipeptide (MIO) in an overall yield of 45%.

$^1$H NMR (CD$_3$CN, 300 MHz): δ 0.24-0.46 (m), 0.88 (d, J=6.1 Hz), 0.93 (d, J=6.3 Hz), 0.91-1.00 (m), 1.06 (d, =6.6 Hz), 1.16 (d, J=6.0 Hz), 1.47 (d, J=7.5 Hz), 1.41-1.52 (m), 1.52-1.61 (m), 1.68-1.87 (m), 2.16 (dt, J=4.2, 12.5 Hz), 2.61-2.78 (ddd, J=5.6, 11.2, 19.7 Hz), 2.89 (dt, J=4.4, 12.6 Hz), 3.14 (s), 3.55 (d, J=6.4 Hz), 4.00 (m), 4.08-4.19 (m), 4.25 (q, J=7.5 Hz), 4.51-4.62 (m), 6.36 (d, J=7.4 Hz), 6.83 (dt. J=1.0, 7.4 Hz), 6.91 (d, J=8.0 Hz), 7.09-7.16 (m), 7.29 (d. J=8.9 Hz)

$^{13}$C NMR (CD$_3$CN, 75 MHz): δ 1.3, 2.7, 14.4, 14.9, 17.7, 21.5, 22.0, 23.4, 25.6, 29.4, 33.5, 39.2, 41.3, 46.7, 53.8, 55.9, 59.0, 60.1, 73.4, 113.2, 121.3, 127.9, 131.4, 132.8, 155.8, 172.3, 172.5, 177.7

The overall yields for representative other compounds of the invention made using the general approach described for 801 and 807 are presented in the following table.

Additional Representative Macrocycle Yields

| Compound | Overall Yield |
|---|---|
| 808 | 38.2% |
| 809 | 36.3% |
| 810 | 42.5% |
| 820 | 5.6% |
| 825 | 56.5% |
| 826 | 27.5% |
| 1003 | 7.8% |
| 1005 | 15.1% |
| 1006 | 4.2% |
| 1007 | 5.6% |
| 1010 | 43.5% |
| 1011 | 52.6% |
| 1017 | 35.3% |
| 1018 | 38.5% |
| 1033 | 25.0% |
| 1034 | 9.6% |
| 1055 | 19.9% |
| 1069 | 9.9% |
| 1072 | 10.5% |
| 1084 | 28.9% |
| 1087 | 38.1% |
| 1088 | 17.2% |
| 1089 | 24.4% |
| 1098 | 20.3% |
| 1106 | 49.1% |
| 1107 | 65.5% |
| 1118 | 33.0% |

C. Standard. Procedure for the Synthesis of Compound 877

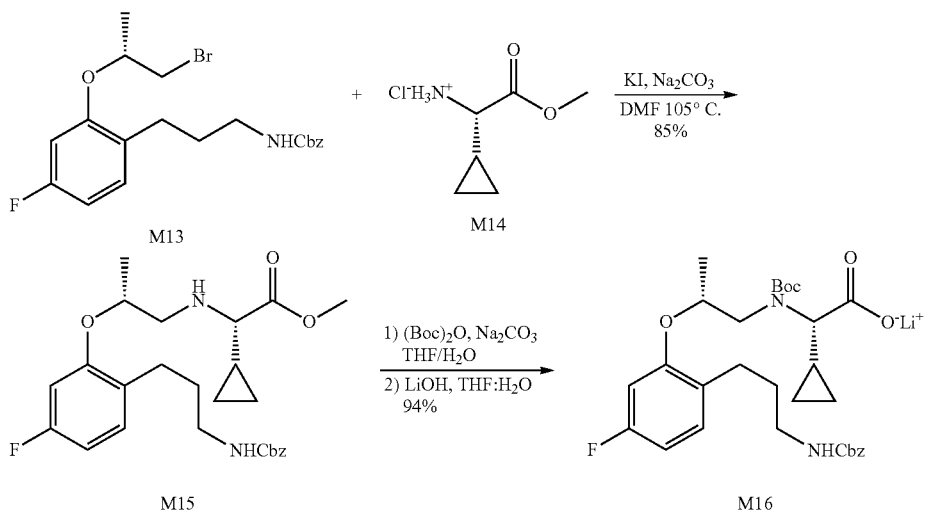

-continued

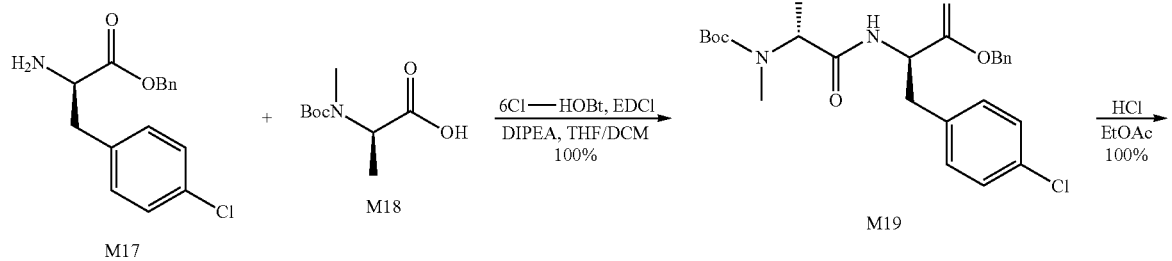

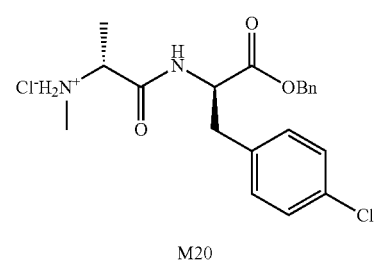

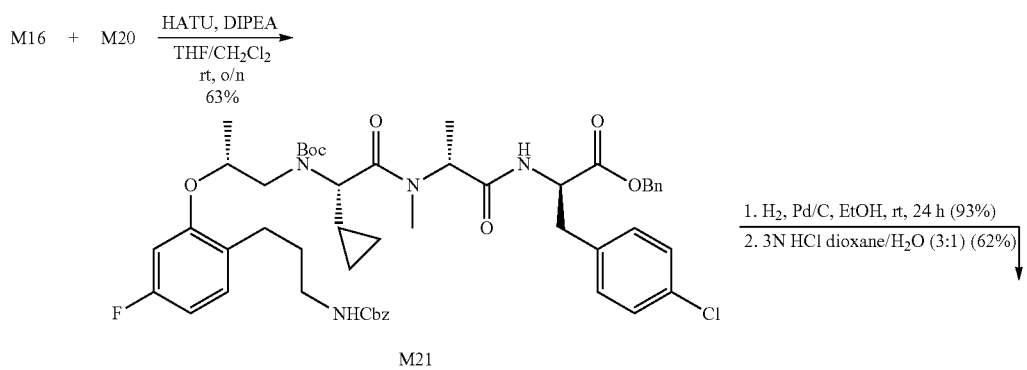

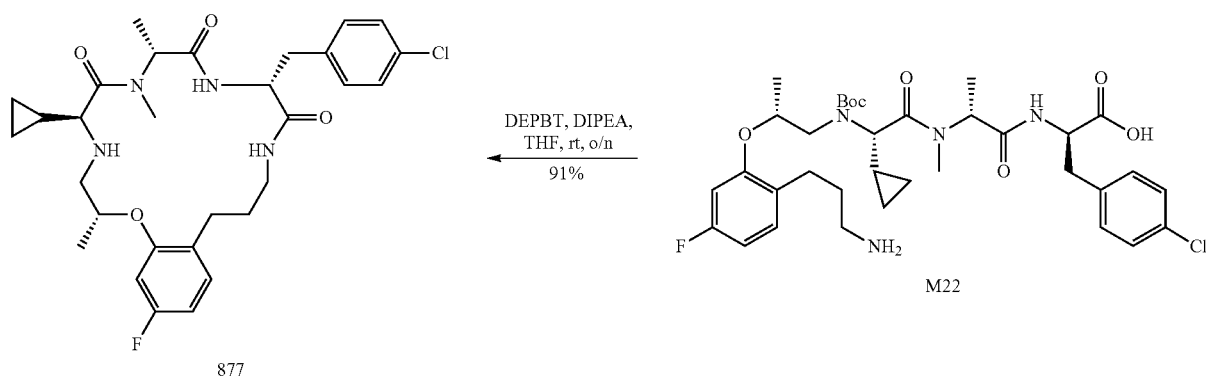

A slightly modified reaction sequence to that described for compounds 801 and 807 can also be employed to assemble the macrocyclic framework. In this approach, the initial alkylation as done via an SN2 displacement rather than a Mitsunobu retraction. This is illustrated for the synthesis of compound 877 from the bromide derived from tether Boc-T75a (M13), cyclopropylglycine methyl ester (M14) and the protected dipeptide (M20) in an overall yield of 35%.

D. Standard Procedure for the Synthesis of Compound 934

A similar reaction sequence to that described for compound 877 was applied to provide compound 934 in 5-10% overall yield starting from the tosylate of Cbz-T9, H-Ile- OMe, Cbz-N-MeSer(OAc)—OH (Hughes, A. B. et. al. *J. Org. Chem.* 2003, 68, 2652-2667) and H-(D)Phe-OMe.

E. Standard Procedure for the Synthesis of Compound 1114

A similar reaction sequence to that described for compound 877 was applied to provide compound 1114 in 16% overall yield starting from the tosylate of Cbz-T9, H-Cpg-OMe, Boc-(D)NMeAla-OH, and H-Tle-OBn.

The foregoing is illustrative of the present invention, and is not to be construed as limiting thereof. The invention is defined by the following claims, with equivalents of the claims to be included therein.

What is claimed is:

1. A method of treating a gastrointestinal disorder comprising administering to a subject in need thereof an effective amount of a compound having the following structure:

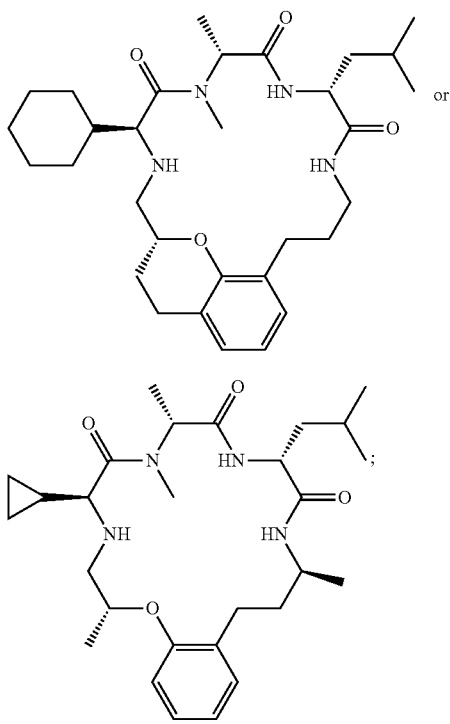

or an optical isomer, enantiomer or diastereomer thereof.

2. The method of claim 1, wherein the compound is the following:

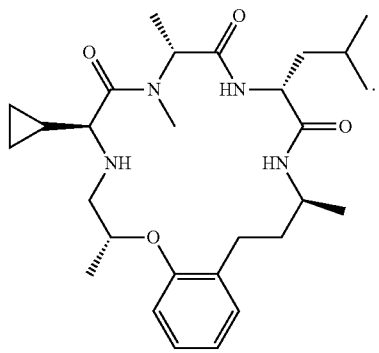

3. The method of claim 1, wherein the gastrointestinal disorder is characterized by gastrointestinal dysmotility.

4. The method of claim 1, wherein the gastrointestinal disorder is postoperative ileus, gastroparesis, opioid-induced bowel dysfunction, chronic intestinal pseudo-obstruction, acute colonic pseudo-obstruction (Ogilvie's syndrome), short bowel syndrome, emesis, constipation-predominant irritable bowel syndrome (IBS), chronic constipation, cancer-associated dyspepsia syndrome, delayed gastric emptying, gastrointestinal dysfunction or delayed gastric emptying in patients with Parkinson's disease, gastrointestinal dysfunction or delayed gastric emptying in myotonic muscular dystrophy, gastrointestinal dysfunction or delayed gastric emptying in patients with scerloderma, gastroesophageal reflux disease (GERD), gastric ulcers or Crohn's disease.

5. The method of claim 4, wherein the gastroparesis is diabetic gastroparesis or postsurgical gastroparesis syndrome.

6. The method of claim 1, wherein the compound is administered orally.

7. The method of claim 1, wherein the compound is administered parenterally.

8. The method of claim 1, wherein the subject is a mammal.

9. The method of claim 1, wherein the subject is a human.

10. The method of claim 1, wherein the subject is a horse.

11. The method of claim 1, wherein the compound is co-administered with an additional agent useful for stimulating gastrointestinal motility.

* * * * *